United States Patent
Bayer et al.

(10) Patent No.: US 11,591,608 B2
(45) Date of Patent: Feb. 28, 2023

(54) PROGRAMMABLE EPIGENETIC CONTROL OF GENE EXPRESSION IN PLANTS

(71) Applicant: Sound Agriculture Company, Emeryville, CA (US)

(72) Inventors: Travis Bayer, Emeryville, CA (US); Kevin L. Schneider, Emeryville, CA (US); Aden Kinne, Emeryville, CA (US); Jennifer Adele Samson, Emeryville, CA (US); Itxaso Garay, Emeryville, CA (US)

(73) Assignee: SOUND AGRICULTURE COMPANY, Emeryville, CA (US)

( * ) Notice: Subject to any disclaimer, the term of this patent is extended or adjusted under 35 U.S.C. 154(b) by 0 days.

(21) Appl. No.: 17/476,097

(22) Filed: Sep. 15, 2021

(65) Prior Publication Data
US 2022/0025389 A1 Jan. 27, 2022

Related U.S. Application Data

(63) Continuation of application No. PCT/US2020/023391, filed on Mar. 18, 2020.

(60) Provisional application No. 62/820,172, filed on Mar. 18, 2019.

(51) Int. Cl.
*C12N 15/82* (2006.01)

(52) U.S. Cl.
CPC ....... *C12N 15/8218* (2013.01); *C12N 15/825* (2013.01); *C12N 15/8262* (2013.01); *C12N 15/8297* (2013.01); *C12N 15/8298* (2013.01)

(58) Field of Classification Search
None
See application file for complete search history.

(56) References Cited

U.S. PATENT DOCUMENTS

| | | | |
|---|---|---|---|
| 9,288,952 B2 | 3/2016 | Sisson | |
| 10,813,311 B2 | 10/2020 | Kramer | |
| 2005/0026160 A1 | 2/2005 | Allerson et al. | |
| 2019/0024086 A1 | 1/2019 | Lande et al. | |
| 2019/0055555 A1* | 2/2019 | Hauser | C12N 15/113 |

FOREIGN PATENT DOCUMENTS

| | | |
|---|---|---|
| WO | 2012018754 A2 | 2/2012 |
| WO | 2014106837 A2 | 7/2014 |
| WO | 2014106838 A2 | 7/2014 |
| WO | 2020191072 A1 | 9/2020 |

OTHER PUBLICATIONS

Chi et al. Reduced polyphenol oxidase gene expression and enzymatic browning in potato (Solanum tuberosum L.) with artificial microRNAs. BMC Plant Biology. 14(62): 1-18. (Year: 2014).*
Wang et al. "Mutual regulation of microRNAs and DNA methylation in human cancers". Epigenetics. 12(3)187-197 (Year: 2017).*
Yu et al. "Methylation as a Crucial Step in Plant microRNA Biogenesis". Science. 307(5711)932-935. (Year: 2005).*
Finnegan et al. "DNA Methylation in Plants". Annu Rev Plant Physiol Plant Mol Biol. 49: 223-49. (Year: 1998).*
Horesh et al. "A rapid method for detection of putative RNAi target genes in genomic data". Bioinformatics. vol. 19, Supplement 2: pp. ii73-ii80. (Year: 2003).*
Bhagwat et al. "An in vivo Transient Expression System Can Be Applied for Rapid and Effective Selection of Artificial MicroRNA Constructs for Plant Stable Genetic Transformation". Journal of Genetics and Genomics. 40(5):261-270. (Year: 2013).*
Marienssen et al. "DNA Methylation and Epigenetic Inheritance in Plants and Filamentous Fungi". Science. 293(5532):1070-1074. (Year: 2001).*
Yoshizumi et al. "Selective Gene Delivery for Integrating Exogenous DNA into Plastid and Mitochondrial Genomes Using Peptide-DNA Complexes". Biomacromolecules. 19: 1582-1591. (Year: 2018).*
Application No. PCT/US2020/023391, International Search Report and Written Opinion, dated Jul. 6, 2021, 10 pages.
Lennox et al., Chemical Modification and Design of Anti-miRNA Oligonucleotides, Gene Therapy, vol. 18, Jul. 14, 2011, pp. 1111-1120.
Smalheiser et al., Mammalian Argonaute-DNA Binding?, Biology Direct, vol. 9, No. 27, Dec. 2014, pp. 1-11.
Xie et al., siRNA-Directed DNA Methylation in Plants, Current Genomics, vol. 16, No. 1, Feb. 2015, pp. 23-31.
Gebala et al., "Quantitative Studies of an RNA Duplex Electrostatics by Ion Counting", Biophysical Journal 117, Sep. 17, 2019, pp. 1116-1124.
Hermann et al., "RNA bulges as architectural and recognition motifs", Structure, vol. 8, No. 3, 2000, pp. R47-R54.
Ma et al., "Angiosperms Are Unique among Land Plant Lineages in the Occurrence of Key Genes in the RNA-Directed DNA Methylation (RdDM) Pathway", Genome Biol. Evol. 7(9), Sep. 2, 2015, pp. 2648-2662.
Richmond et al., "The structure of DNA in the nucleosome core", Nature, vol. 423, May 8, 2003, pp. 145-150.
Tanaka et al., "A'-form RNA double helix in the single crystal structure of r(UGAGCUUCGGCUC)", Nucleic Acids Research, vol. 27, No. 4, 1999, pp. 949-955.
Zhang et al., "Dynamics and function of DNA methylation in plants", Nature Reviews: Molecular Cell Biology, vol. 19, Aug. 2018, pp. 489-506.
Application No. PCT/US2022/073384, International Search Report and Written Opinion, dated Oct. 14, 2022, 15 pages.

(Continued)

*Primary Examiner* — Cathy Kingdon Worley
*Assistant Examiner* — David R Byrnes
(74) *Attorney, Agent, or Firm* — Kilpatrick Townsend & Stockton LLP

(57) ABSTRACT

Disclosed herein are artificially synthesized nucleic acid constructs to guide an epigenetic modification for at least partially silencing or activating a target gene in an organism such as a plant or seed, and formulations thereof. Also disclosed are methods of applying such nucleic acid constructs to the plant or to the seed. Also disclosed are engineered seeds and plants obtained by the epigenetic modification.

15 Claims, 11 Drawing Sheets
Specification includes a Sequence Listing.

(56) References Cited

OTHER PUBLICATIONS

"Solanum Lycopersicum Chromosome Ch07, Complete Genome", NCBI, GenBank: HG975519.1., Nov. 17, 2015, 1 page.
Ecker, "Epigenetic Trigger for Tomato Ripening", Nature Biotechnology, vol. 31, No. 2, Feb. 2013, pp. 1-4.
Liu et al., "SIGRAS4 Accelerates Fruit Ripening by Regulating Ethylene Biosynthesis Genes and SIMADS1 in Tomato", Horticulture Research., vol. 8, No. 3, Jan. 1, 2021, pp. 1-11.
Zhang et al., "The SIFSR Gene Controls Fruit Shelf-Life in Tomato", Journal of Experimental Botany, vol. 69, No. 12, Apr. 4, 2018, pp. 2897-2909.
Application No. EP20773409.6, Extended European Search Report, dated Nov. 17, 2022, 6 pages.

\* cited by examiner

SEQ ID NO: 289/290

CGCGGTAGGTGGGAGGTTTTTGAmA
TCAAAAACCTCCCACCTACGCGmU

TpCpApApApApApCpCpTpCpCpApCpCpTpApCpCpGpCpGpmU
CpGpCpGpGpTpApGpGpTpGpGpGpApGpGpTpTpTpTpTpGpApmA

Example of 100% backbone modified (fN = 2'Fluoro, mN = 2'O-Methyl, s = phosphorothioate)

mUsmCsfApmApfApmApfApmCpfCpmApfCpmCpfUpmApfCpmCpfGpmCsmGsmU
fCsfGsmCpfGpmGpfUpmApfGpmGpfUpmGpfApmGpfGpmUpfUpmUpfGsmAsmA

Example of PS linkage placement (s = PS)

TsCpApApApApApCpCpTpCpCpApCpCpTpApCpCpGpCpGsmU
CsGpCpGpGpTpApGpGpTpGpGpGpApGpGpTpTpTpTpTpGsApmA

TsCsApApApApApCpCpTpCpCpApCpCpTpApCpCpGpCsGsmU
CsGsCpGpGpTpApGpGpTpGpGpGpApGpGpTpTpTpTpTpGsAsmA

TsCsApApApApApCpCpTpCpCpApCpCpTpApCpCsGsCsGsmU
CsGsCsGpGpTpApGpGpTpGpGpGpApGpGpTpTpTpTsGsAsmA

FIG. 11

PROGRAMMABLE EPIGENETIC CONTROL OF GENE EXPRESSION IN PLANTS

CROSS-REFERENCE

The present application is a continuation of PCT/US2020/023391, filed Mar. 18, 2020, which claims the benefit of U.S. Provisional Application Ser. No. 62/820,172, filed Mar. 18, 2019, both of which are hereby incorporated by reference in their entirety.

The official copy of the sequence listing is submitted electronically via EFS-Web as an ASCII formatted sequence listing with a file named SequenceListing_107621-1267525, created on Oct. 5, 2021, and having a size of 173 KB. The sequence listing contained in this ASCII formatted document is part of the specification and is herein incorporated by reference in its entirety.

BRIEF SUMMARY

In some aspects, disclosed herein is a nucleic acid construct, e.g., a polynucleotide. In some instances, the present disclosure provides an artificial nucleic acid construct, wherein the artificial nucleic acid construct comprises: (a) a ribose modified at a 2' or 3' position, or a deoxyribose modified at a 2' or 3' position, or a combination thereof; and (b) a terminal end overhang, wherein: the artificial nucleic acid construct is double stranded; at least one strand of the artificial nucleic acid construct independently comprises a length from at least: about 10 to about 30 nucleotides or nucleosides or a combination thereof, and when contacted with an organism, at least a portion of the artificial nucleic acid construct is configured to facilitate: i) an epigenetic modification of at least one base of a nucleotide or nucleoside in a nucleic acid sequence of the organism, ii) a silencing of a target mRNA sequence that is at least partially complementary to the at least one strand of the artificial nucleic acid construct, iii) a cleavage of the target mRNA sequence, or iv) any combination of i), ii), or iii). In some instances, the artificial nucleic acid construct comprises no epigenetic modification on any purine or pyrimidine base of a nucleotide or nucleoside. In some instances, the artificial nucleic acid construct facilitates the epigenetic modification through a system that at least in part comprises a DNA methyltransferase, a biologically active fragment thereof, or a derivative thereof. In some instances, the artificial nucleic acid construct facilitates the epigenetic modification through a system that at least in part comprises a DNA acetyltransferase, a biologically active fragment thereof, or a derivative thereof. In some instances, the system comprises at least a portion of at least one component of an RNA directed DNA methylation pathway. In some instances, the at least one component comprises a protein or a portion thereof. In some instances, the protein or portion thereof is an enzyme or a portion thereof. In some instances, the artificial nucleic acid construct is capable of facilitating the epigenetic modification in the absence of a CRISPR, a CRISPR-associated protein (Cas), a biologically active fragment thereof, a derivative thereof, a fusion protein thereof, or any combination thereof. In some instances, the artificial nucleic acid construct is capable of facilitating the epigenetic modification in the absence of a Cas that comprises Cas1, Cas2, Cas3, Cas4, Cas5, Cas6, Cas7, Cas8, Cas9, or any combination thereof. In some instances, at least about 80% of sugars of the artificial nucleic acid construct, based on a total number of the sugars, each independently comprises a deoxyribose, modified deoxyribose, or a combination thereof. In some instances, less than about 20% of sugars of the artificial nucleic acid construct, based on a total number of the sugars, each independently comprises a ribose, a modified ribose, or a combination thereof. In some instances, the artificial nucleic acid construct is at least partially encoded by an RNA or DNA: nucleotide or nucleoside, or a combination thereof. In some instances, at least about 80% of the nucleotides, nucleosides, or a combination thereof of the artificial nucleic acid construct are DNAs. In some instances, a terminal nucleotide or terminal nucleoside of the artificial nucleic acid construct comprises an RNA: nucleotide or nucleoside, or a combination thereof. In some instances, multiple nucleotides in the nucleic acid sequence have the same epigenetic modification. In some instances, at least 10-12 nucleotides in the nucleic acid sequence have the same epigenetic modification. In some instances, the nucleic acid sequence comprises at least about 100 contiguous nucleotides. In some instances, the nucleic acid sequence comprises a CpG island. In some instances, the modified ribose or the modified deoxyribose is at a terminal nucleotide or nucleoside of the artificial nucleic acid construct. In some instances, the modified ribose or the modified deoxyribose comprises a 2'-O—R group. In some instances, R group is selected from the group consisting of: an alkyl, an aryl, a haloalkyl, an amino, a methyl, acetyl, and a halo. In some instances, the R group is the methyl. In some instances, the artificial nucleic acid construct further comprises a modification in at least one of a purine or pyrimidine base. In some instances, the modification comprises a plurality of modifications. In some instances, the modification increases stability of the artificial nucleic acid construct. In some instances, the modification increases uptake of the artificial nucleic acid construct by the organism. In some instances, the modification is substantially positioned at a 3' end of the artificial nucleic acid construct. In some instances, the modification is substantially positioned at a 5' end of the artificial nucleic acid construct. In some instances, the modification comprises a methyl group, a methoxy group, an ester group, a fluoro group, a phosphorthioate backbone, or any combination thereof. In some instances, the terminal end overhang is a 3' end overhang. In some instances, the artificial nucleic acid construct comprises two 3' end overhangs. In some instances, at least one strand of the artificial nucleic acid construct independently comprises a length from about 20 to about 30 nucleotides or nucleosides or a combination thereof. In some instances, the artificial nucleic acid construct comprises at least one deoxyribonucleic acid. In some instances, the artificial nucleic acid construct comprises at least one ribonucleic acid. In some instances, the artificial nucleic acid construct comprises at least one strand that is not phosphorylated at its 5' terminus. In some instances, the organism comprises a plant, a seed, a fruit, a leaf, a stalk, a root, a flower, an archaeon, a bacterium, a fungus, a virus, a virus-like particle, a protist, an alga, a nematode, a portion of any of these, or any combination thereof. In some instances, the artificial nucleic acid construct comprises at least about: 80%, 85%, 90%, 95%, or 98%; or about 100% sequence identity or at least 10 contiguous bases of one or more of SEQ ID NOs: 1-62. In some instances, the artificial nucleic acid construct comprises at least about: 80%, 85%, 90%, 95%, or 98%; or about 100% sequence identity or at least 10 contiguous bases of one or more of SEQ ID NOs: 63-194. In some instances, the artificial nucleic acid construct comprises at least about: 80%, 85%, 90%, 95%, or 98%; or about 100% sequence identity or at least 10 contiguous bases of one or more of SEQ ID NOs: 195-404. In some instances, the artificial nucleic acid construct comprises at least about: 80%, 85%, 90%, 95%, or 98%; or about 100% sequence identity or at least 10 contiguous bases of one or more of SEQ ID NOs: 405-584. In some instances, the artificial nucleic acid construct comprises at least about: 80%, 85%, 90%, 95%, or 98%; or about 100% sequence identity or at least 10 contiguous bases of one or more of SEQ ID NOs: 585-684. In some instances, the artificial nucleic acid construct comprises a peptide nucleic acid, a morpholino, a locked nucleic acid, a glycol nucleic acid, a threose nucleic acid, or any combination thereof positioned in the backbone of the artificial nucleic acid construct. In some instances, the epigenetic modification is comprised in a polynucleotide sequence at least partially encoding one or more proteins of Nuclear RNA polymerase D1 (NRPD1), NRPE1, NRPD2/NRPE2, NRPD4/NRPE4, NRPE5, NRPE9B, NRPB1, RNA-Dependent RNA Polymerase 2 (RDR2), DICER-Like 3 (DCL3), HUA Enhancer 1 (HEN1), Argonaute 4 (AGO4), AGO6, AGO9, Classy 1 (CLSY1), Defective in RNA-Directed DNA Methylation 1 (DRD1), Defective in Meristem Silencing 3 (DMS3), RNA-Directed DNA Methylation 1 (RDM1), KOW Domain-Containing Transcription Factor 1 (KTF1), Involved in De Novo 2 (IDN2), IDN2 Paralogue1 (IDP1), IDP2, DMS4, Domains Rearranged Methyltransferase 2 (DRM2), SUVH2, SUVH9, SUVR2, Microrchidia 1 (MORC1), MORC6, Sawadee homeodomain homologue 1 (SHH1), Histone Deacetylase 6 (HDA6), Jumonji 14 (JMJ14), Lysine-specific Histone Demethylase 1 (LDL1), LDL2, Ubiquitin-specific Protease 26 (UBP26), Needed For RDR2-Independent DNA Methylation (NERD), Chromomethylase 2 (CMT2), CMT3, Methyltransferase 1 (MET1), SUVH4, Decreased DNA Methylation 1 (DDM1), a biologically active fragment thereof, a regulatory element associated therewith, an intron associated therewith, or any combination thereof. In some instances, the epigenetic modification is catalyzed by an enzyme or a catalytically or biologically active fragment thereof. In some instances, the enzyme or catalytically or biologically active fragment thereof is endogenous to the organism. In some instances, the enzyme or catalytically or biologically active fragment thereof comprises a TET family enzyme or a catalytically or biologically active fragment thereof. In some instances, the enzyme or catalytically or biologically active fragment thereof comprises a methyltransferase or a catalytically or biologically active fragment thereof. In some instances, the methyltransferase comprises a chromomethyltransferase (CMT), a domain rearranged methyltransferase (DRM), or a combination thereof. In some instances, the epigenetic modification adds a chemical group to the at least one base. In some instances, the epigenetic modification adds a methyl group to the at least one base, and wherein the methyl group is oxidized to a methoxy, formyl, or carboxyl group, or a carboxylic acid. In some instances, the at least one base is a cytosine. In some instances, the epigenetic modification comprises a methyl group, a hydroxymethyl group, a formyl group, a carboxyl group, or any combination thereof. In some instances, the epigenetic modification comprises the methyl group. In some instances, the nucleic acid sequence comprises a transcription regulatory region. In some instances, a strand of the double stranded artificial nucleic acid construct comprises at least about: 80%, 85%, 90%, 95%, or 98%; or about 100% sequence identity to a portion of a transcription regulatory region. In some instances, the transcription regulatory region comprises at least about 30% guanine cytosine (GC) content.

In some aspects, the present disclosure provides a plurality of artificial nucleic acid constructs disclosed herein (double stranded or single stranded), for example at least about: 2-100, 2-90, 2-80, 2-70, 2-60, 2-50, 2-40, 2-30, 2-24, 2-12, 4-100, 4-90, 4-80, 4-70, 4-60, 4-50, 4-40, 4-30, 4-24, 4-12, 6-100, 6-90, 6-80, 6-70, 6-60, 6-50, 6-40, 6-30, 6-24, 6-12, 8-100, 8-90, 8-80, 8-70, 8-60, 8-50, 8-40, 8-30, 8-24, 8-12, 10-100, 10-90, 10-80, 10-70, 10-60, 10-50, 10-40, 10-30, 10-24, or 10-12 of the artificial nucleic acid constructs herein. In some instances, at least about 10% to about 100% of the number of the artificial nucleic acid constructs are different in the plurality. In some instances, each artificial nucleic acid construct in the plurality is different.

In some aspects, the present disclosure provides a method for making the artificial nucleic acid construct disclosed herein, comprising adding to the artificial nucleic acid construct a nucleotide or nucleoside comprising a ribose modified at a 2' or 3' position, or a deoxyribose modified at a 2' or 3' position, or a combination thereof.

In some aspects, the present disclosure provides a method for making the artificial nucleic acid constructs disclosed herein, comprising modifying a ribose, deoxyribose, or a combination thereof at the 2' or 3' position in the artificial nucleic acid construct.

In some aspects, the present disclosure provides a method for making the plurality of artificial nucleic acid constructs, comprising mixing two or more of the artificial nucleic acid constructs disclosed herein.

In some aspects, the present disclosure provides an isolated cell comprising the artificial nucleic acid construct disclosed herein or a plurality thereof. In some instances, the cell is a eukaryotic cell.

In some aspects, the present disclosure provides a plant, seed, solution, microorganism, fertilizer, or soil comprising the artificial nucleic acid construct disclosed herein or a plurality thereof.

In some aspects, the present disclosure provides a composition comprising: (a) an artificial nucleic acid construct disclosed herein and (b) an enzyme or a catalytically or biologically active fragment thereof that performs an epigenetic modification of at least one base in a nucleic acid sequence of an organism.

In some aspects, the present disclosure provides a composition comprising: a vector comprising one or more artificial nucleic acid constructs herein or a plurality thereof.

In some aspects, the present disclosure provides a kit comprising: (a) an artificial nucleic acid construct, a plurality thereof, or a composition thereof as disclosed herein; and (b) a container comprising a soil, a fertilizer, a seed, a plant, a liquid, or any combination thereof.

In some aspects, the present disclosure provides a formulation comprising: (a) an artificial nucleic acid construct, a plurality thereof, or a composition thereof as disclosed herein; and (b) an excipient. In some instances, the excipient is an agriculturally acceptable excipient. In some instances, the formulation further comprises a fertilizer or a soil.

In some aspects, the present disclosure provides a method of making a formulation, comprising contacting an artificial nucleic acid construct, a plurality thereof, or a composition thereof as disclosed herein with an excipient to form the formulation.

In some aspects, the present disclosure provides an engineered plant or seed comprising a heritable modification that at least partially silences or activates at least one gene of the engineered plant or seed, wherein the heritable modification comprises a methylated base in a transcription regulatory region of the at least one gene, and wherein the heritable modification does not comprise a transgene, optionally comprising the artificial nucleic acid construct or a plurality thereof. In some instances, two genes are silenced. In some instances, the at least one methylated base is not naturally methylated in the nucleic acid sequence. In some instances, the transcription regulatory region comprises at least one selected from the group consisting of: a transcription start site, a TATA box, and an upstream activating sequence. In some instances, the methylated base comprises a plurality of methylated bases.

In some aspects, the present disclosure provides a plurality of engineered plants or seeds comprising variable gene expressions that at least partially silence or activate at least one gene of the engineered plants or seeds, optionally comprising the artificial nucleic acid construct or a plurality thereof disclosed herein. In some instances, the engineered plants or seeds comprise at least one modified base in at least one gene therein, which is not naturally methylated in the gene. In some instances, the base is modified with an alkyl, an aryl, a haloalkyl, an amino, a methyl, acetyl, a halo, or a combination thereof. In some instances, the engineered plants or seeds comprise at least one methylated base in at least one gene therein. In some instances, the plurality comprises at least about: 10-20, 20-50, 50-100, 100-1000, 100-900, 100-800, 100-700, 100-600, 100-500, 100-400, 100-300, 100-240, 100-120, or 1000-10000 of engineered plants or seeds.

In some aspects, the present disclosure provides a method, comprising applying a substance to an agricultural object, wherein the agricultural object comprises a seed, a plant, a constituent of a plant, or any combination thereof, and wherein the substance comprises the artificial nucleic acid construct or a plurality thereof disclosed herein. In some instances, the method at least partially silencing or activating a gene in the agricultural object. In some instances, the gene is at least partially silenced for at least one or two reproduction cycles. In some instances, the applying results in one or more of the following: (a) preventing or reducing or delaying an enzymatic browning of the agricultural object; (b) increasing a growth rate, a yield, or a lifespan of the agricultural object; (c) decreasing a growth rate, a yield, or a lifespan of the agricultural object; (d) increasing a pest resistance, a salt tolerance, a heat tolerance, a heavy metal tolerance, a disease tolerance, or a drought resistance of the agricultural object; (e) increasing or at least partially decreasing an amount or a production of a molecule made by the agricultural object; (f) altering a color of at least a portion of the agricultural object; (g) increasing or at least partially decreasing a flowering rate of the agricultural object; (h) increasing a volume or a weight of the agricultural object; (i) improving a flavor or a texture of an edible product of the agricultural object; (j) increasing a shelf life of the agriculture product; (k) decreasing the number and size of seeds of the agriculture product; and (j) increasing a nutritional content of the agricultural object; when the agricultural object is compared to a comparable agricultural object without application of the substance comprising the artificial nucleic acid construct. In some instances, the agricultural object is a plant embryo. In some instances, the agricultural object is selected from the group consisting of: soybean, corn, rice, tomato, alfalfa, wheat, potato, and green algae. In some instances, the contacting decreases the growth rate, the yield, or the lifespan of a weed. In some instances, the contacting increases the growth rate, the yield, or the lifespan of the agricultural object, and wherein the molecule is a psychoactive substance. In some instances, the psychoactive substance comprises a tetrahydrocannabinol. In some instances, the substance is a liquid, soil, microorganism, fertilizer, or herbicide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative instances, in which the principles of the disclosure are utilized, and the accompanying drawings of which:

FIG. 6A illustrates that in a wild type plant, shoots grow in the opposite direction of the force of gravity (gravitropism). FIG. 6B illustrates that LZY1-CATS plants show a loss of gravitropism compared to wild type plants. FIG. 6C illustrates that in a wild type plant, shoots grow in the opposite direction of the force of gravity (gravitropism). FIG. 6D illustrates that LZY1-CATS plants show a loss of gravitropism compared to wild type plants.

FIG. 7A illustrates that a CATS-treated potato shows a slower enzymatic browning as compared to an untreated control potato. FIG. 7B depicts RT-PCT analysis of PPO mRNA levels in CATS-treated potato plants. CATS plants have reduced levels of the mRNA transcript, as compared to the control mRNA in untreated plants (FIG. 7C).

FIG. 11 depicts exemplary CATS oligonucleotides with modified backbones comprising phosphorothioate modifications, 2'O-Methyl modifications, 2'-Fluoro modifications, or any combination thereof.

DETAILED DESCRIPTION

Introduction

Figure 1:
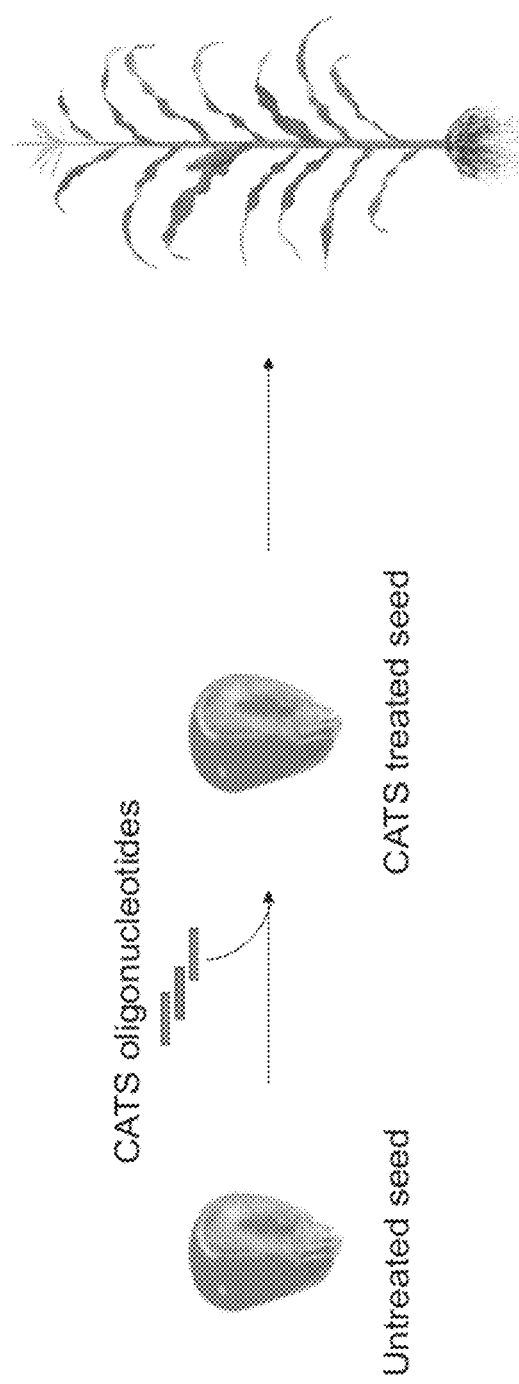
FIG. 1 depicts schematically treatment of an untreated seed with a plurality of CATS oligonucleotides.
Figure 2:
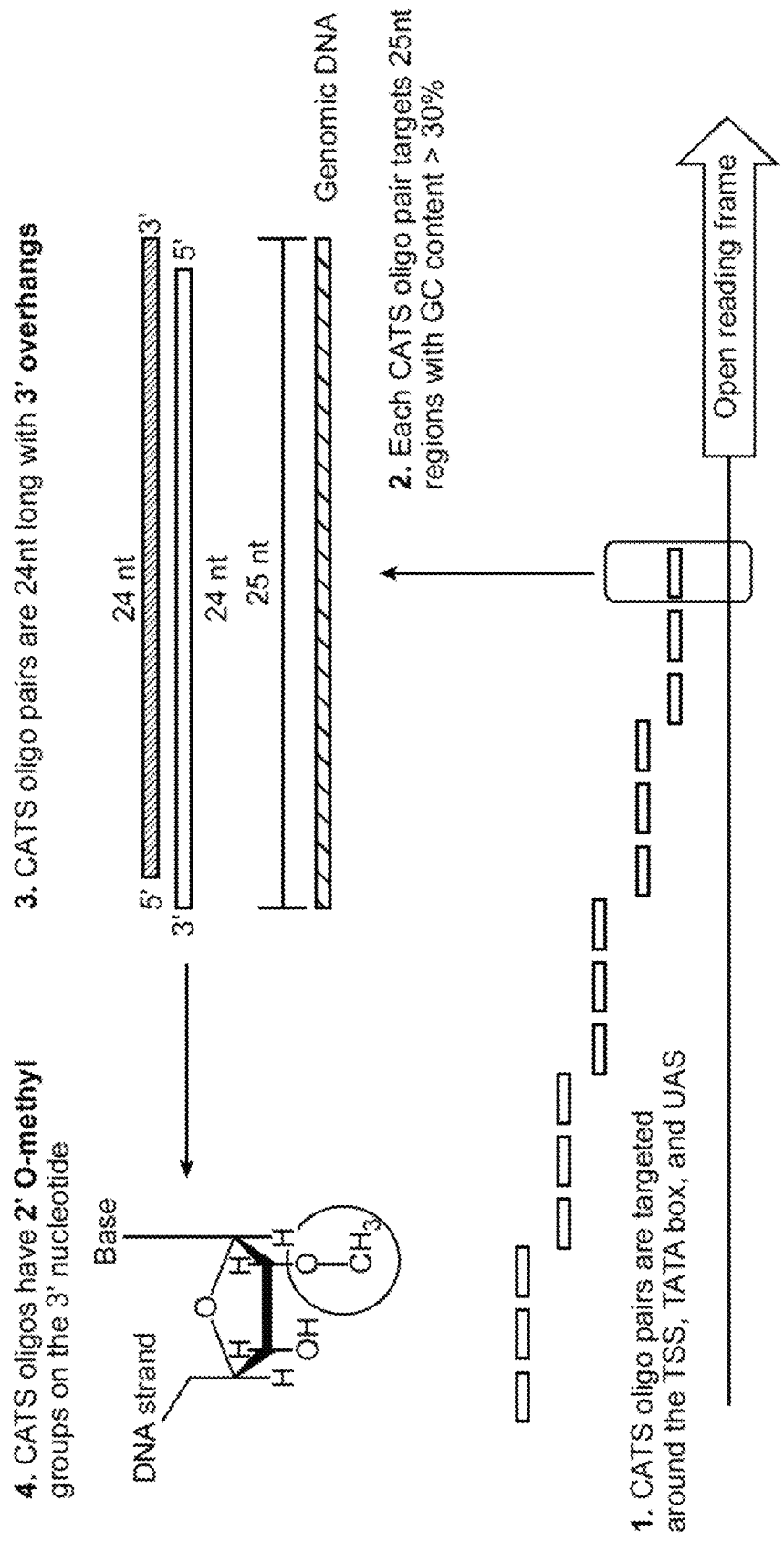
FIG. 2 depicts a non-limiting example of the design of a CATS oligonucleotide.

Disclosed herein are molecular techniques for at least partially silencing or activating specific target genes in plants to elicit desired phenotypes with commercial value. In some instances, this technology is referred to as Coat Applied Transcriptional Silencing (CATS) and uses specifically engineered DNA oligonucleotides constructs to induce nitrogenous base modification (e.g., cytosine methylation) and epigenetic silencing of target genes. The methods disclosed herein allow the specific and multiplex manipulation of plant gene expression, with design and build workflow of days, compared to the months or years necessary for transgenic approaches.

An engineered DNA oligonucleotide described herein can be prepared to mimic a nucleic acid sequence present in an RNA interference pathway. In some cases, an RNA interference pathway can be a pathway naturally present in an organism (e.g. a plant, a fungus, a bacterium, or an animal). For example, an engineered DNA oligonucleotide can be prepared to mimic a nucleic acid sequence present in a *Drosophila melanogaster, Caenorhabditis elegans,* or *Arabidopsis thaliana* RNA interference pathway. An exemplary RNA interference pathway can include an *Arabidopsis thaliana* RNA interference pathway. In the exemplary *Arabidopsis thaliana* RNA interference pathway, a first RNA nucleic acid is prepared through transcription using a polymerase IV enzyme. The first RNA nucleic acid transcribed from polymerase IV can be single stranded, or can be converted into a double stranded RNA nucleic acid. A resulting double stranded nucleic acid can be processed by a dicer enzyme (for instance, a Dicer-Like 3 (DCL3) enzyme) to produce smaller double stranded RNA nucleic acid fragments. Such RNA nucleic acid fragments can be methylated on a 2' or 3' hydroxyl group present on a ribose sugar present on the RNA nucleic acid fragments by a HUA Enhancer 1 (HEN1) enzyme or biological equivalent thereof. The methylated double-stranded RNA strand can be processed by an Argonaute 4 (AGO4) enzyme or biological equivalent thereof to produce a single stranded, methylated RNA nucleic acid. In some cases, the methylated RNA nucleic acid can modulate an expression of a gene (including a level of mRNA encoded by a gene or a polypeptide encoded by an mRNA) in an organism through multiple pathways. For instance, a methylated RNA nucleic acid can bind directly to an mRNA sequence encoding the polypeptide, thus acting as a silencing RNA nucleic acid. Further, a methylated RNA nucleic acid can recruit enzymes, such as AGO4, capable of inducing a cleavage of the mRNA when the methylated RNA nucleic acid associates with the mRNA sequence. Further, a methylated mRNA nucleic acid can associate with a DNA methylating enzyme, such as Domains Rearranged Methyltransferase 2 (DRM2), to catalyze a de novo methylation of genomic DNA encoding the mRNA sequence. In some cases, a methylated RNA nucleic acid can modulate an expression of a gene in an organism through any one, any 2, or all of 3 of these actions.

Accordingly, an engineered oligonucleotide can be engineered to mimic a nucleic acid present in an RNA interference pathway. For example, an engineered oligonucleotide can be engineered to mimic a methylated RNA nucleic acid, such as an RNA nucleic acid methylated using a HEN1 enzyme. Accordingly, such an engineered oligonucleotide can modulate an expression of a gene (including a level of mRNA encoded by a gene or a polypeptide encoded by an mRNA) in an organism through any combination of the actions referenced above. For example, an engineered oligonucleotide can bind directly to an mRNA sequence encoding the polypeptide, thus acting as a silencing nucleic acid. Further, an engineered oligonucleotide can recruit enzymes, such as AGO4, capable of inducing a cleavage of the mRNA when the engineered oligonucleotide associates with the mRNA sequence. Further, an engineered oligonucleotide can associate with a DNA methylating enzyme, such as Domains Rearranged Methyltransferase 2 (DRM2), to catalyze a de novo methylation of genomic DNA encoding the mRNA sequence. In some cases, an engineered oligonucleotide can modulate an expression of a gene in an organism through any one, any 2, or all of 3 of these actions.

Furthermore, an engineered oligonucleotide can be designed to be at least partially complementary to a desired target mRNA sequence. In some cases, a desired target mRNA sequence can be an mRNA that is a target of a natural methylated RNA nucleic acid in an RNA interference pathway. In some cases, a desired target mRNA can be an mRNA that is separate and distinct from any target of a natural methylated RNA nucleic acid in an RNA interference pathway. Accordingly, highly specific gene regulation can be accomplished by generating engineered oligonucleotides that are capable of associating with a target mRNA nucleic acid of interest.

In some instances, engineered nucleic acid constructs are designed with high sequence homology to a transcription regulatory region upstream of a target gene's open reading frame. In some instances, the nucleic acid constructs can be a double stranded DNA construct having at least one end overhang, such that the DNA construct mimics the double stranded RNA recognized by the plant's endogenous DNA methylation machinery, thereby directing endogenous DNA methylation to the transcription regulatory region. In some instances, methylation of cytosines in a gene's transcription regulatory region at least partially silence the gene.

Use of the nucleic acid constructs described herein has several advantages. The specifically designed oligonucleotides introduce cytosine methylation at a defined region of a plant genome, which can control transcript expression levels. The nucleic acid constructs can be introduced by application to the seed coat or to the growing roots of the plant, enabling rapid construction of plants with tailored gene expression profiles. In some instances, the modified bases (e.g., methylated cytosines) are heritable, enabling generation of parental breeding lines with desired expression profiles. Methylation and altered transcript levels can be propagated through future progeny generations. Additionally, the application of nucleic acid constructs to plants can be multiplexed by application of mixtures of nucleic acid constructs having unique targeting sequences, such that multiple transcription regulatory regions of a gene, and/or multiple gene, may be targeted simultaneously.

Yield drivers can be regulated by epigenetic mechanisms. Examples of yield drivers are hybrid vigor, photosynthesis and seed size. Stress resistance can be regulated by epigenetic mechanisms. Examples of stress resistance are disease resistance, drought tolerance, salt tolerance, heat tolerance and heavy metal stress. The applications of the CATs nucleotides can be broad and potentially encompass many gene regulatory networks that affect phenotype.

For example, constructs as described herein may provide one or more epigenetic modifications to one or more genes of an organism—such as an agricultural product. Introduction of such epigenetic modifications may modify one or more characteristics of the agricultural product. Such characteristics may include one or more of: photosynthesis, heterosis, nutrient efficiency, energy efficiency, seed size, plant biomass, circadian rhythm, flowering time, seed development, root development, disease resistance, drought tolerance, salt tolerance, heat tolerance, heavy metal stress, or any combination thereof. One or more characteristics may comprise flavor, color, texture, shelf-life, seedless varieties, or any combination thereof. An epigenetic modification to a gene may modify a characteristic. An epigenetic modification to a gene may modify a plurality of characteristics. A plurality of epigenetic modifications may modify a characteristic. A plurality of epigenetic modifications may modify a plurality of characteristics.

Additionally, constructs as described herein can be utilized to create diverse pools of organisms such as an agricultural product. Constructs can introduce one or more epigenetic modifications into one or more genes of an organism. Introduction of one or more epigenetic modifications can result in at least partial silencing or at least partial activation of one or more genes. Activation or silencing or a combination thereof of one or more genes in an organism can result in diversifying a species. Introducing epigenetic modifications into one or more genes of an organism can create a diverse pool of progeny. Such downstream applications can include breeding selection, such as selecting for advantageous characteristics.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive instances or aspects are set forth in the accompanying drawings, the claims, and the description herein. Other features, objects, and advantages of the inventive instances or aspects disclosed and contemplated herein can be combined with any other instance or aspect unless explicitly excluded.

The open terms for example "contain," "containing," "include," "including," and the like mean comprising.

The singular forms "a", "an", and "the" are used herein to include plural references unless the context clearly dictates otherwise.

Unless otherwise indicated, some instances herein contemplate numerical ranges. When a numerical range is provided, unless otherwise indicated, the range can include the range endpoints. Unless otherwise indicated, numerical ranges can include all values and subranges therein as if explicitly written out.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

The term "facilitates" herein can refer to i) a machinery that when a construct is introduced to an organism with an appropriate molecular system for an epigenetic modification, it facilitates or enables the organism to use at least a part of the molecular system to epigenetically modify a nucleic acid sequence in the organism, or ii) a silencing of a target mRNA sequence that is at least partially complementary to the at least one strand of the artificial nucleic acid construct, iii) a cleavage of the target mRNA sequence, or iv) any combination of i), ii), or iii).

The term "compounds" can refer to compounds encompassed by generic formulae disclosed herein, any subgenus of those generic formulae, and any specific compounds within those generic or subgeneric formulae. The compounds can be a specific species, a subgenus or larger genus identified either by their chemical structure and/or chemical name. Further, compounds also include substitutions or modifications of any of such species, subgenuses or genuses, which are set forth herein. When the chemical structure and chemical name conflict, the chemical structure can be determinative of the identity of the compound. The compounds can contain one or more chiral centers and/or double bonds and therefore, can exist as stereoisomers, isomers, enantiomers or diastereomers. Accordingly, the chemical structures within the scope of the specification encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the compounds are illustrated, asterisks indicate the point of attachment of the partial structure to the rest of the molecule. Enantiomeric and stereoisomeric mixtures can be resolved into their component enantiomers or stereoisomers using separation techniques or chiral synthesis techniques well known to the skilled artisan. The compounds can include any salt or solvate forms of the compounds. The compounds can include any derivatives of the compounds.

The term "derivative," which can be used interchangeably with the term "analog." Compound A can be a derivative or analog of compound B if 1, 2, 3, 4, or 5 atoms of compound A is replaced by another atom or a functional group (e.g., amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl) to form compound B. The term "derivative" may also refer to a chemical compound that is structurally similar to another but differs slightly in composition (as in the replacement of one atom by an atom of a different element or in the presence of a particular functional group)

The term "solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

The term "salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

Unless otherwise indicated, a chemical structure can refer to any compound having the chemical structure.

Unless otherwise indicated, formulations herein can be powdery, pellets, or beads or be a liquid.

Unless otherwise indicated, formulations herein can contain water in an amount from about 0% to about 15% w/w, for example about: 0-10%, 0-5%, or 0-1% w/w; or less than about: 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90% or 99% w/w, based on the weight of the formulation.

Unless otherwise indicated, whenever there is a stereocenter in a structure disclosed or illustrated herein, the stereocenter can be R or S in each case.

Unless otherwise indicated, whenever there is a symbol

when used as part of a molecular structure herein can refer to a single bond.

The term "amino" can refer to functional groups that contain a basic nitrogen atom with a lone pair. For example, amino can include the radical

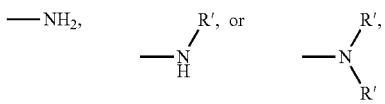

wherein each R' is independently H, halo, alkyl, aryl, heteroalkyl, arylalkyl, heteroaryl, heteroarylalkyl, cycloalkyl, or heterocycloalkyl.

The term "halo" or "halogen" can refer to fluorine, chlorine, bromine or iodine or a radical thereof.

The term "alkyl" can refer to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "aryl" can refer to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain instances, an aryl group comprises from 6 to 20 carbon atoms.

The terms "heteroalkyl, heteroalkanyl, heteroalkenyl, heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, O, S O—O', —S—S—, —O—S—, NR'—, =N—N=, —N=N—, —N=N—NR'—, —PH—, —P(O)$_2$—, —O—P(O)$_2$—, —S(O)—, —S(O)$_2$—, —SnH$_2$— and the like, wherein R' is hydrogen, alkyl, substituted alkyl, cycloalkyl, substituted cycloalkyl, aryl or substituted aryl.

The term "heteroaryl" can refer to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain instances, the heteroaryl group is from 5-20 membered heteroaryl, and in other instances is from 5-10 membered heteroaryl. In certain instances heteroaryl groups are those derived from thiophene, pyrrole, benzothiophene, benzofuran, indole, pyridine, quinoline, imidazole, oxazole and pyrazine.

The term "arylalkyl" can refer to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain instances, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$).

The term "heteroarylalkyl" can refer to an acyclic alkyl group in which one of the hydrogen atoms bonded to a carbon atom, typically a terminal or sp$^a$ carbon atom, is replaced with a heteroaryl group. Where specific alkyl moieties are intended, the nomenclature heteroarylalkanyl, heteroarylalkenyl and/or heteroarylalkynyl is used. In certain instances, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl.

The term "cycloalkyl" can refer to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a certain instance, the cycloalkyl group is ($C_3$-$C_{10}$) cycloalkyl, or in certain instances ($C_3$-$C_6$) cycloalkyl.

The term "heterocycloalkyl" can refer to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Typical heterocycloalkyl groups include, but are not limited to, groups derived from epoxides, imidazolidine, morpholine, piperazine, piperidine, pyrazolidine, pyrrolidine, quinuclidine, and the like.

The term "diastereomeric excess" (DE) can refer to the difference from the relative abundance of two diastereomers. For instance, if there are two diastereomers and their mole or weight percentages are A and B, then DE can be calculated as: DE=[(A−B)/(A+B)]*100%. For example, if a mixture contains 75% of one diastereomer and 25% of the other diastereomer, the diastereomeric excess is 50%. In another example, if a mixture that is 95% of one diastereomer, the diastereomeric excess is 90%.

The term "enantiomeric excess" (EE) can refer to the difference from the relative abundance of two enantiomers. For instance, if there are two enantiomers and their mole or weight percentages are A and B, then EE can be calculated as: EE=[(A−B)/(A+B)]*100%. For example, if a mixture contains 75% of one enantiomer and 25% of the other enantiomer, the enantiomeric excess is 50%. In another example, if a mixture that is 95% of one enantiomer, the enantiomeric excess is 90%.

The term "substituted" can refer to a group in which one or more hydrogen atoms are each independently replaced with the same or different substituent(s). Typical substituents include, but are not limited to halo, alkyl, aryl, heteroalkyl, arylalkyl, heteroaryl, heteroarylalkyl, cycloalkyl, and heterocycloalkyl.

Unless otherwise indicated, "treated" can refer to "contacted." Similarly, "untreated" can refer to "uncontacted."

The term "substantially comparable plant" can refer to a plant of the same species as an earlier referenced plant. For example, a substantially comparable but otherwise uncontacted plant belongs to the same species as a contacted plant. The substantially comparable but otherwise uncontacted plant can have a height of about 80% to 120% of the contacted plant (as measured from the surrounding soil to the highest point of the plant) and/or can have a mass of about 80% to 120% of the contacted plant.

The term "drought" can mean conditions with less than 20 inches, 15 inches, 10 inches, or 5 inches of rainfall within the past 12 months. The term "drought" can also mean conditions with a Palmer Drought Severity Index (PDSI) of less than −1.0. The term "adequately irrigated condition" can mean a condition with more than 20 inches of rainfall within the past 12 months. The term "adequately irrigated condition" can mean a condition with a PDSI of more than −1.0.

The term "plant" can be used interchangeably with the term "crop" and can include, but is not limited to any crop, cultivated plant, fungus, or alga that may be harvested for food, clothing, livestock fodder, biofuel, medicine, or other uses. For example, plants include field and greenhouse crops, including but not limited to broad acre crops, fruits and vegetables, perennial tree crops, and ornamentals. Plants include, but are not limited to sugarcane, pumpkin, maize (corn), wheat, rice, cassava, soybeans, hay, potatoes, cotton, tomato, alfalfa, and green algae. Plants also include, but are not limited to any vegetable, such as cabbage, turnip, carrot, parsnip, beetroot, lettuce, beans, broad beans, peas, potato, eggplant, tomato, cucumber, pumpkin, squash, onion, garlic, leek, pepper, spinach, yam, sweet potato, and cassava. In some instances, the plant can also include a fruit, a leaf, a stalk, a root, a flower, a plant embryo, or any combination thereof Nucleic Acid Constructs Disclosed herein are nucleic acid constructs for at least partially silencing or activating a gene in an organism, wherein the nucleic acid construct is configured to guide endogenous modification (e.g., methylation) of at least one base of the gene in the organism. In some instances, the nucleic acid construct can be single-stranded or double-stranded.

In some instances, the nucleic acid construct can be an artificial double-stranded nucleic acid construct comprising 1) a modified ribose or a modified deoxyribose or a combination thereof and 2) a terminal end overhang, wherein, when the nucleic acid construct associates with a nucleic acid sequence of an organism, an enzyme performs an epigenetic modification of at least one base in the nucleic acid sequence of the organism. In some instances, the modified ribose or the modified deoxyribose is comprised in a terminal nucleotide of the nucleic acid construct. In some instances, the nucleic acid construct associates with an argonaut protein that associates with the nucleic acid sequence.

In some instances, the nucleic acid construct can comprise deoxyribonucleic acid (DNA), ribonucleic acid (RNA), or a combination thereof. In some instances, the nucleic acid construct can comprise at least one deoxyribonucleic acid. In some instances, the nucleic acid construct can comprise at least about: 2, 3, 4, 5, 6, 7, 8, 9, 10, 15, 20, 25, 30, 35, 40, 45, 50, 55, 60, 65, 70, 75, 80, 85, or 100 deoxyribonucleic acids. In some instances, the nucleic acid construct can comprise at least one ribonucleic acid. In some instances, the nucleic acid construct can comprise at least about: 2, 3, 4, 5, 6, 7, 8, 9, 10, 15, 20, 25, 30, 35, 40, 45, 50, 55, 60, 65, 70, 75, 80, 85, or 100 ribonucleic acids.

In some instances, the base of the gene may be a cytosine. In some instances, the base of the gene may be an adenine, a guanine, or a thymine.

In some instances, the nucleic acid construct may be a double stranded DNA construct. In some instances, the double stranded DNA construct may comprise two polynucleotide strands of the same length. In some instances, the double stranded DNA construct may comprise two polynucleotide strands of a different length. In some instances, the double stranded DNA construct may comprise at least one end overhang. In some instances, an end overhang may comprise a single nucleotide. In some instances, an end overhang may comprise at least about: 2, 3, 4, 5, 6, 7, 8, 9, or 10 nucleotides. In some instances, the double stranded DNA construct may comprise an end overhang at each end of the DNA construct. In some instances, the double stranded DNA construct may comprise an end overhang at each end of the DNA construct, wherein the end overhangs are of the same length. In some instances, the double stranded DNA construct may comprise a one-nucleotide end overhang at each end of the DNA construct. In some instances, the double stranded DNA construct may comprise a 3'-end overhang. In some instances, the double stranded DNA construct may comprise a 5'-end overhang. In some instances, the double stranded DNA construct may comprise a one-nucleotide 3'-end overhang at each end of the DNA construct.

In some instances, the nucleic acid construct may comprise at least one modified sugar, for example modified at the 2' position and/or the 3' position. Numbering of a nucleotide sugar should be understood to follow normal conventions of positional numbering in the art. Specifically, carbon numbering in nucleotide sugar is as illustrated by ribose sugar shown below:

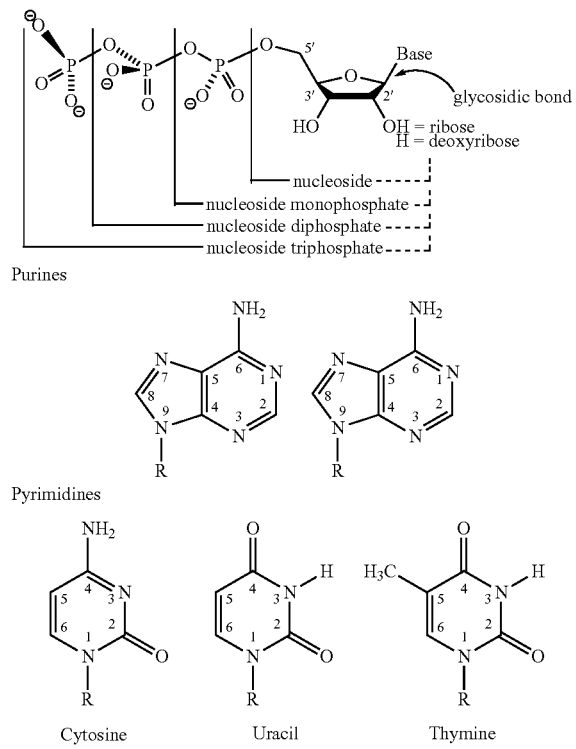

In some instances, the modified sugar may comprise a 2'-R, 2'-O—R, 3'-R, or 3'-O—R group. In some instances, the R group may be selected from the group consisting of alkyl, aryl, haloalkyl, amino, and halogen. In some instances, the R group can be a fluro-(F). In some instances, the R group can be methoxyethyl. In some instances, the R group can be methyl. In some instances, R can be —(C═O)n-R1, or the ribose modification comprises the structure represented by:

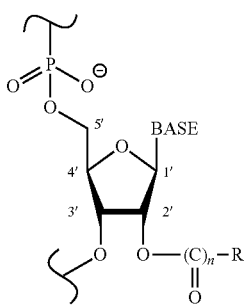

In some instances, R1 can be alkyl, alkenyl, alkynyl aryl, substituted alkyl, substituted alkenyl, substituted alkynyl, or a substituted aryl.

In some instances, the modified sugar may be comprised in a terminal nucleotide of at least one strand of the nucleic acid construct. In some instances, the modified sugar may be comprised in a 3'-terminal nucleotide of at least one strand of the nucleic acid construct. In some instances, the nucleic acid construct may be a double stranded DNA construct, wherein each strand of the DNA construct comprises at least one modified sugar. In some instances, the nucleic acid construct may be a double stranded DNA construct, wherein each strand of the DNA construct comprises at least one modified sugar in the strand's 3'-terminal nucleotide.

In some cases, the sugar can be a derivative of ribose. In some instances, the sugar can be arabinose. In some instances, the sugar may be 2'-deoxy-2'-fluoro-arabino (FANA). In some instances, the sugar may be a derivative of hexose (e.g. HNA; hexose nucleic acid). In some instances, the sugar may be a derivative of threose (e.g. TNA; threose nucleic acid). In some instances, the sugar may be replaced with a morpholino group and the backbone composed of phosphoramidate linkages (e.g. PMO; Phosphorodiamidate Morpholino Oligomer) In some instances, the sugar may be a bridged sugar (e.g. BNA; bridged nucleic acid). In some instances, the bridging carbon between the 2' and 4' positions may be a methylene group (e.g. LNA; locked nucleic acid). In some instances, the bridging carbon between the 2' and 4' positions may be an ethyl group. In some instances, the 2',4'-constrained ethyl sugar derivative may be in the S stereochemical configuration (e.g. (S)-cET). In some instances, the sugar can be acyclic. In some instances, sugar may be a derivative or ribose lacking the 2' and 3'-bond (e.g. UNA; unlocked nucleic acid). In some instances, the sugar may be a derivative of threoninol (e.g aTNA; threoninol nucleic acid). In some instances, the sugar may be a derivative of serinol (e.g. SNA; serinol nucleic acid). In some instances, the sugar may be a derivative of glycol (e.g. GNA; glycol nucleic acid).

In some cases, the sugars within each strand are linked 3' to 5' by a bridging phosphodiester linkage. In some instances one oxygen within the phosphodiester linkage may be replaced with a sulfur forming a phosphorthioate. In some instances, two oxygens within phosphodiester linkage are replaced with sulfur forming a phosphorodithioate linkage. In some instances, the 3'-5' phosphodiester contains an additional ester group on a non-bridging oxygen. In some instances the sugar bridging phosphate may be a phosphotriester. In some instances, the phosphotriester may be stable. In some instances, the phosphotriester may be bioreversible.

In some cases, a nucleic acid disclosed herein is associated with or encapsulated within a liposome. In some instances, the liposome may be comprised of a cationic peptide (e.g. DOTAP). In some instances, the liposome may be comprised of an ionizable lipid (e.g. DLinDMA or KC2-DMA).

In some cases, a nucleic acid disclosed herein may be associated with or encapsulated within a nano or microparticle. In some instances, nano or microparticle may be comprised of poly lactic-co-glycolic acid (PLGA). In some instances, the nucleic acid may be attached to a nanoparticle. In some instances the nanoparticle may be a liposome. In some instances the nanoparticle may be a micelle. In some instances the nanoparticle comprises silica. In some instances the nanoparticle comprises a mineral or mineral derivative. In some instances, the nucleic acid may be conjugated to a nanoparticle comprised gold. In some instances the nanoparticle may be a quantum dot. In some instances, the nucleic acid may be conjugated to a nanoparticle comprised of DNA or other nucleic acids. In some instances, the nucleic acid may be attached to a microparticle. In some instances the microparticle may comprise silica. In some instances the microparticle may comprise clay.

In some cases, one or more nucleic acid sequences may be directly conjugated to a ligand or other moiety to enhance uptake, transport, cytoplasmic or nuclear delivery. In some instances, the ligand may be attached to a 5' end of the nucleic acid duplex. In some instances, the ligand may be attached to a 3' end of the nucleic acid duplex. In some instances, the ligand may be attached to both the 5' end and the 3' end of the nucleic acid duplex. In some instances, the ligand may be attached to a position within the nucleic acid duplex. In some instances, the ligand may be attached to the non-Watson-Crick face of one of the nucleobases. In some instances, the ligand may be attached to the 5-position of uracil. In some instances, the ligand is attached to multiple positions on the nucleic acid. In some instances, more than one ligand may be attached. In some instances, the multiple copies of the same ligand are attached. In some instances, multiple different ligands are attached.

In some instances, the ligand may be a sugar or polysaccharide. In some instances, the ligand may be GalNAc. In some instances, the ligand may be two GalNAc moieties attached to a single position on the nucleic acid. In some instances, the ligand may be three GalNAc moieties attached to a single position on the nucleic acid. In some instances, the ligand may be more than three GalNAc moieties attached to a single position on the nucleic acid. In some instances, the ligand may be chitin or a derivative thereof. In some instances, the ligand may be mannose or a derivative thereof. In some instances, the ligand may be sialic acid or a derivative thereof.

In some instances, a nucleic acid disclosed herein may be conjugated to a peptide or derivative thereof. In some instances, the peptide may enhance nucleic acid uptake. In some instances, the peptide may enhance endosomal escape. In some instances, the peptide may enhance both uptake and endosomal escape. In some instances, the peptide may enhance delivery to vascular tissue and long-distance transport. In some instances, the peptide may be a cationic. In some instances, the peptide may be a derivative of a viral protein. In some instances, the ligand may be an arginine rich peptide (e.g. TAT). In some instances, the peptide may be histidine rich peptide (e.g. endoporter). In some instances, the peptide may be a lytic peptide (e.g. melittin). In some instances, the peptide may be a masked peptide that may be activated upon exposure to acidic conditions. In some instances, the peptide may be pH sensitive. In some instances, the peptide may be a derivative of a bacterial protein. In some instances, the peptide may be a derivative of flagellin. In some instances, the peptide may be a derivative of EF-Tu.

In some cases, a nucleic acid disclosed herein may be conjugated to a sterol or sterol derivative. In some instances, the nucleic acid may be conjugated to cholesterol or a cholesterol derivative. In some instances the nucleic acid may be conjugated to a lipid. In some instances the nucleic acid may be conjugated to a single chain lipid. In some instances the nucleic acid may be conjugated to a single chain lipid that contains from 1 to 22 carbons. In some instances the nucleic acid may be conjugated to a single chain lipid that is saturated. In some instances the nucleic acid may be comprised of at least one unsaturated position. In some instances the nucleic acid may be conjugated to a diacyl lipid. In some instances the nucleic acid may be conjugated to diacyl lipid that contains from 1 to 22 carbons. In some instances the nucleic acid may be conjugated to a diacyl lipid that is saturated. In some instances the nucleic acid comprises at least one unsaturated position. In some instances, the nucleic acid may be conjugated to a vitamin or vitamin derivative. In some instances, the nucleic acid may be conjugated to tocopherol.

In some instances, the nucleic acid construct comprises at least about: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base pairs. In some instances, the nucleic acid construct comprises at least about: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base pairs. In some instances, the nucleic acid construct comprises from 2 to about 100 base pairs. In some instances, the nucleic acid construct comprises from about 10 to about 50 base pairs. In some instances, the nucleic acid construct comprises from about 10 to about 40 base pairs. In some instances, the nucleic acid construct comprises from about 10 to about 30 base pairs. In some instances, the nucleic acid construct comprises from about 20 to about 30 base pairs. In some instances, the nucleic acid construct comprises from about (4, 6, 8, or 10) to about 24 base pairs, e.g., about 10 to about 24 base pairs. In some instances, the nucleic acid construct comprises 23 base pairs. In some instances, the nucleic acid construct comprises 24 base pairs.

In some instances, the nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to a transcription regulatory region of the gene.

In some instances, the transcription regulatory region comprises at least about 10%, 15%, 20%, 25%, 30%, 35%, 40%, 45%, 50%, 55%, 60%, 65%, 70%, 75%, 80%, 85%, or 90% guanine-cytosine content (G-C content). In some instances, the nucleic acid construct comprises at least one nucleotide strand having at least about 10%, 15%, 20%, 25%, 30%, 35%, 40%, 45%, 50%, 55%, 60%, 65%, 70%, 75%, 80%, 85%, or 90% G-C content.

In some instances, the nucleic acid construct comprises at least one polynucleotide strand that may not be phosphorylated at a terminal nucleotide of the polynucleotide strand. In some instances, the nucleic acid construct comprises at least one polynucleotide strand that may not be phosphorylated at a 5'-terminal nucleotide of the polynucleotide strand. In some instances, the nucleic acid construct comprises at least one polynucleotide strand that may not be phosphorylated at a 3'-terminal nucleotide of the polynucleotide strand. In some instances, the nucleic acid construct may be a double stranded nucleic acid construct that comprises two polynucleotide strands, wherein each of the polynucleotide strands may not be phosphorylated at a 5'-terminal nucleotide of the polynucleotide strand. In some instances, the nucleic acid construct may be a double stranded DNA construct that comprises two polynucleotide strands, wherein each of the polynucleotide strands may not be phosphorylated at a 3'-terminal nucleotide of the polynucleotide strand.

In some instances, the gene is at least partially silenced for at least one reproduction cycle. At least partial gene silencing should be understood to mean that the gene is transcribed at a level that is decreased relative to the unmodified gene. In some instances, the unmodified gene is a wild type gene. Measurement of gene transcription may be done by any of methods commonly known in the art, such as measure of mRNA transcript levels. In some instances, the gene is at least partially silenced for at least about: 2, 3, 4, 5, 6, 7, 8, 9, 10, 15, 20, or 30 reproduction cycles. In some instances, the gene may be at least about: 5%, 10%, 15%, 20%, 25%, 30%, 35%, 40%, 45%, 50%, 55%, 60%, 65%, 70%, 75%, 80%, 85%, 90%, 95%, 99%, or 100% silenced, as determined by measurement of a corresponding mRNA transcript level of the gene.

In some instances, disclosed herein is a nucleic acid construct configured to recruit an endogenous epigenetic modifying enzyme or fragment thereof to a portion of said nucleic acid sequence that is targeted for epigenetic modification. "Endogenous" should be understood to mean naturally occurring within the organism that contains the gene. Thus, an "endogenous" epigenetic modifying enzyme should be understood to mean a modifying enzyme that is naturally present in the organism that contains the gene.

In some instances, the nucleic acid construct may comprise a nucleic acid sequence having 50%, 55%, 60%, 65%, 70%, 75%, 80%, 85%, 90%, 95%, 96%, 97%, 98%, 99%, 99.5%, 99.9%, or 100% sequence identity to a nucleic acid sequence of any one SEQ ID NOs: 1-664. In some instances, the nucleic acid construct may comprise a nucleic acid sequence having a nucleic acid sequence of any one SEQ ID NOs: 1-664.

In some cases, an enzyme or fragment thereof may catalyze a transfer of a methyl group to at least one base of a nucleic acid sequence, such as a portion of a gene or a transcription regulatory region of a gene. In some cases, an enzyme or fragment thereof may comprise a methyltransferase. In some cases, an enzyme or fragment thereof may comprise a methyltransferase (MET), a chromomethyltransferase (CMT), a domain rearranged methyltransferase (DRM), any catalytically active fragment thereof, or any combination thereof. In some cases, enzyme may comprise Dnmt3a, Dnmt3b, Dnmt3L, DRM1, DRM2, NtDRM1, Zmet3, Fmu, Dnmt1, MET1, DIM2, DRM2, CMT1, CMT3, any catalytically active fragment thereof, or any combination thereof. A CMT enzyme may comprise OsCMT3, ZCMT3, OsCMT1, NtCMT1, CMT3, any catalytically active fragment thereof or any combination thereof. A MET enzyme may comprise NtMET1, OsMET1-2, ZMET1, OsMET1-1, MET1, any catalytically active fragment thereof, or any combination thereof. A DRM enzyme may comprise OsDRM3, OsDRM2, OsDRM1a, OsDRM1b, ZMET3, NtDRM1, DRM1, DRM2, any catalytically active fragment thereof, or any combination thereof. A DNMT2 enzyme may comprise OsDNMT2, ZMET4, OsCMT2, any catalytically active fragment thereof, or any combination thereof. A nucleic acid sequence may be contacted with any of the forgoing enzymes or fragments thereof thereby yielding an epigenetic modification of at least one base in a nucleic acid sequence (such as a gene of interest). Compositions as described herein, including nucleic acid constructs, may guide endogenous enzymes or fragments thereof to a base of interest in a nucleic acid sequence and thereby direct the contact of the enzyme or fragment thereof with the base of interest such that the enzyme or fragment thereof performs epigenetic modification of the base of interest.

Methods as described herein may comprise methylating one or more bases of a nucleic acid sequence (such as a portion of a gene or a transcription regulatory region of a gene). Methods as described herein may comprise oxidizing one or more bases of a nucleic acid sequence, such as a portion of a gene or a transcription regulatory region of a gene. Methods as described herein may comprise epigenetically modifying at least one base of a nucleic acid sequence, said epigenetically modification being heritable to a plant progeny.

In some cases, an enzyme or fragment thereof may catalyze a change in an epigenetic modification of at least one base of a nucleic acid sequence (such as a portion of a gene or a transcription regulatory region of a gene). A change in an epigenetic modification may include a conversion of a methylated base to a hydroxymethylated base, a carboxylated base, a formylated base, or a combination of any of these. In some cases, an enzyme may comprise a dioxygenase. In some cases, an enzyme may comprise a ten-eleven translocation (TET) family enzyme. In some cases, an enzyme may comprise TET1, TET2, TET3, COX finger protein 4 ($CXXC_4$), any catalytically active fragment thereof, or any combination thereof.

An epigenetic modification may occur at any base, such as a cytosine, a thymine, a uracil, an adenine, a guanine, or any combination thereof. The epigenetic modification may be a heritable epigenetic modification, such as an epigenetic modification passed to at least one progeny of an organism. The epigenetic modification may be an engineered epigenetic modification, such as an epigenetic modification that is not non-naturally occurring at a particular base in a nucleic acid sequence of a native organism but one that is introduced into the organism or into an ancestor of an organism using a method as described herein. An organism may comprise a heritable epigenetic modification that may have been previously introduced into a parent organism or an ancestor organism that is retained for at least one reproduction cycle.

In some cases, an epigenetic modification may comprise an oxidation or a reduction. A nucleic acid sequence may comprise one or more epigenetically modified bases. An epigenetically modified base may comprise any base, such as a cytosine, a uracil, a thymine, adenine, or a guanine. An epigenetically modified base may comprise a methylated base, a hydroxymethylated base, a formylated base, or a carboxylic acid containing base or a salt thereof. An epigenetically modified base may comprise a 5-methylated base, such as a 5-methylated cytosine (5-mC). An epigenetically modified base may comprise a 5-hydroxymethylated base, such as a 5-hydroxymethylated cytosine (5-hmC). An epigenetically modified base may comprise a 5-formylated base, such as a 5-formylated cytosine (5-fC). An epigenetically modified base may comprise a 5-carboxylated base or a salt thereof, such as a 5-carboxylated cytosine (5-caC).

A construct may comprise one or more modifications, such as a chemical modification. A construct may comprise about: 1, 2, 3, 4, 5, 6, 7, 8, 9, 10, 11, 12, 13, 14, 15, 16, 17, 18, 19, 20, 25, 30, 35 modifications or more. A construct may comprise from about 1 to about 10 modifications. A construct may comprise from about 1 to about 20 modifications. A construct may comprise from about 5 to about 20 modifications. A modification may be added to a construct to enhance stability of the construct, such as when delivered in vivo. A modification may be added to a construct to enhance update of the construct, such as when delivered in vivo. A portion of bases of a construct may comprise a modification, such as about 10%, 20%, 30%, 40%, 50%, 60%, 70%, 80%, 90% of bases or more. A modification may comprise addition of a methyl group, a fluoro group, a phosphorthioate backbone, or any combination thereof.

A construct may be double stranded. A double stranded constructs may comprise a length of from about 10 basepairs (bp) to about 100 bp. Constructs may comprise a length of from about 10 bp to about 20 bps. Constructs may comprise a length of from about 10 bp to about 30 bps. Constructs may comprise a length of from about 10 bp to about 40 bps. Constructs may comprise a length of from about 10 bp to about 50 bps. Constructs may comprise a length of from about 10 bp to about 60 bps. Constructs may comprise a length of from about 10 bp to about 70 bps. Constructs may comprise a length of from about 10 bp to about 80 bps. Constructs may comprise a length of from about 10 bp to about 90 bps. Constructs may comprise a length of from about 15 bp to about 40 bp. Constructs may comprise a length of from about 15 bp to about 35 bp. Constructs may comprise a length of from about 15 bp to about 60 bp. Constructs may comprise a length of from about 5 bp to about 30 bp. Constructs may comprise a length of from about 5 bp to about 25 bps.

Detection of Epigenetic Modification

In some aspects, an epigenetic modification disclosed herein such as DNA methylation can be detected. In some instances, the modification, e.g., methylated nucleotide, may be detected by bisulfite sequencing. Bisulfite treatment may convert a cytosine base to uracil and leave methylated cytosines unconverted. Bisulfite treatment may be applied to a portion of a sample and leave a second portion of the sample untreated. Bisulfite treatment may be performed on a sample prior to sequencing or after sequencing. Bisulfite treatment may be utilized alone or in combination with additional techniques to determine a presence, a pattern or a level of epigenetic modification in a nucleic acid sequence, such as a presence, a pattern or a level of methylation in a sequence. Bisulfite sequencing may determine a presence, a pattern, or a level of an epigenetic modification in a nucleic acid sequence. Bisulfite-free sequencing may determine a presence, a pattern, or a level of an epigenetic modification in a nucleic acid sequence. A bisulfite treated sequence may be compared to a comparable sequence having not been treated with bisulfite to determine a presence, a pattern, or a level of epigenetic modification in a nucleic acid sequence.

Sequencing (such as bisulfite-free sequencing) may be utilized alone or in combination with additional techniques to determine a presence, a pattern or a level of epigenetic modification in a nucleic acid sequence, such as a presence, a pattern or a level of methylation in a sequence. Sequencing (such as bisulfite-free sequencing) may determine a presence, a pattern, or a level of an epigenetic modification in a nucleic acid sequence. Sequencing may determine a presence, a pattern, or a level of an epigenetic modification in a nucleic acid sequence. A treated sequence (such as a sequence having a label added to an epigenetic modification) may be compared to a comparable sequence having not been treated to determine a presence, a pattern, or a level of epigenetic modification in a nucleic acid sequence.

The term "sequencing" as used herein, may comprise bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore DNA sequencing, shot gun sequencing, RNA sequencing, Enigma sequencing, or any combination thereof.

In some cases, a method may comprise sequencing. The sequencing may include bisulfite sequencing or bisulfite-free sequencing.

In some instances, the methods may include storing the sample for a time such as seconds, minutes, hours, days, weeks, months, years or longer after the sample is obtained and before the sample is analyzed. In some cases, the sample obtained from a subject is subdivided prior to the step of storage or further analysis such that different portions of the sample are subject to different downstream methods or processes including but not limited to any combination of methods described herein, storage, bisulfite treatment, amplification, sequencing, labeling, cytological analysis, adequacy tests, nucleic acid extraction, molecular profiling or a combination thereof.

In some cases, a portion of the sample may be stored while another portion of said sample is further manipulated. Such manipulations may include but are not limited to any method as described herein; bisulfite treatment; sequencing; amplification; labeling; molecular profiling; cytological staining; nucleic acid (RNA or DNA) extraction, detection, or quantification; gene expression product (RNA or Protein) extraction, detection, or quantification; fixation; and examination.

In some instances, a methylated nucleotide may be detected by nanopore sequencing. Nanopores may be used to sequence, a sample, a small portion (such as one full gene or a portion of one gene), a substantial portion (such as multiple genes or multiple chromosomes), or the entire genomic sequence of an individual. Nanopore sequencing technology may be commercially available or under development from Sequenom (San Diego, Calif.), Illumina (San Diego, Calif.), Oxford Nanopore Technologies LTD (Kidlington, United Kingdom), and Agilent Laboratories (Santa Clara, Calif.). Nanopore sequencing methods and apparatus are have been described in the art and for example are provided in U.S. Pat. No. 5,795,782, herein incorporated by reference in its entirety.

Nanopore sequencing can use electrophoresis to transport a sample through a pore. A nanopore system may contain an electrolytic solution such that when a constant electric field is applied, an electric current can be observed in the system. The magnitude of the electric current density across a nanopore surface may depend on the nanopore's dimensions and the composition of the sample that is occupying the nanopore. During nanopore sequencing, when a sample approaches and or goes through the nanopore, the samples cause characteristic changes in electric current density across nanopore surfaces, these characteristic changes in the electric current enables identification of the sample. Nanopores used herein may be solid-state nanopores, protein nanopores, or hybrid nanopores comprising protein nanopores or organic nanotubes such as carbon or graphene nanotubes, configured in a solid-state membrane, or like framework. In some instances, nanopore sequencing can be biological, a solid state nanopore or a hybrid biological/solid state nanopore.

In some instances, a biological nanopore can comprise transmembrane proteins that may be embedded in lipid membranes. In some instances, a nanopore described herein may comprise alpha hemolysin. In some instances, a nanopore described herein may comprise *Mycobacterium smegmatis* porin.

Solid state nanopores do not incorporate proteins into their systems. Instead, solid state nanopore technology uses various metal or metal alloy substrates with nanometer sized pores that allow samples to pass through. Solid state nanopores may be fabricated in a variety of materials including but not limited to, silicon nitride ($Si_3N_4$), silicon dioxide ($SiO_2$), and the like. In some instances, nanopore sequencing may comprise use of tunneling current, wherein a measurement of electron tunneling through bases as sample (ssDNA) translocates through the nanopore is obtained. In some instances, a nanopore system can have solid state pores with single walled carbon nanotubes across the diameter of the pore. In some instances, nanoelectrodes may be used on a nanopore system described herein. In some instances, fluorescence can be used with nanopores, for example solid state nanopores and fluorescence. For example, in such a system the fluorescence sequencing method converts each base of a sample into a characteristic representation of multiple nucleotides which bind to a fluorescent probe strand-forming dsDNA (were the sample comprises DNA). Where a two-color system is used, each base is identified by two separate fluorescence, and will therefore be converted into two specific sequences. Probes may consist of a fluorophore and quencher at the start and end of each sequence, respectively. Each fluorophore may be extinguished by the quencher at the end of the preceding sequence. When the dsDNA is translocating through a solid state nanopore, the probe strand may be stripped off, and the upstream fluorophore will fluoresce.

In some instances, a 1-100 nm channel or aperture may be formed through a solid substrate, usually a planar substrate, such as a membrane, through which an analyte, such as single stranded DNA, is induced to translocate. In other instances, a 2-50 nm channel or aperture is formed through a substrate; and in still other instances, a 2-30 nm, or a 2-20 nm, or a 3-30 nm, or a 3-20 nm, or a 3-10 nm channel or aperture if formed through a substrate.

In some instances, nanopores used in connection with the methods and devices useful herein are provided in the form of arrays, such as an array of clusters of nanopores, which may be disposed regularly on a planar surface. In some instances, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical detection system employed.

Sequence Identity

The terms "homologous," "homology," or "percent homology" as used herein refer to the degree of sequence similarity between an amino acid or nucleotide sequence and a reference sequence. As used herein, the term "homology" can be used interchangeably with the term "identity." In some instances, the degree of sequence similarity herein can be at least about 60%, at least about 65%, at least about 70%, at least about 75%, at least about 80%, at least about 85%, at least about 90%, or at least about 95%, or about 100%. In some instances, percent sequence homology can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application. In some instances, percent homology of sequences can be determined using Smith-Waterman homology search algorithm. Smith & Waterman (1981) Adv. Appl. Math. 2: 482-489.

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues. Most sequence comparison method over longer sequences are designed to produce optimal alignments that take into consideration possible insertions and deletions without penalizing unduly the overall homology score. This is achieved by inserting "gaps" in the sequence alignment to try to maximize local homology. These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is a commonly used gap scoring system. High gap penalties will of course produce optimized alignments with fewer gaps. Most alignment programs allow the gap penalties to be modified. Typically the default values are used when using such software for sequence comparisons. Calculation of maximum % homology therefore firstly requires the production of an optimal alignment, taking into consideration gap penalties. Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. In some instances, an alignment is determined by the Smith-Waterman homology search algorithm using an affine gap search with a gap open penalty of 12 a gap extension penalty of 2, and a blocks substitution matrix (BLOSUM) of 62.

Formulations

Also disclosed herein are formulations comprising: one or more nucleic acid constructs, one or more plants or seeds, one or more plant growth regulators, or any salt or solvate thereof, or any combination thereof. The formulation can be as a seed treatment, soil drench, granule formulation, or foliar spray to improve the productivity or alter the phenotype of a wide variety of crops.

Further disclosed herein are formulations comprising one or more nucleic acid construct described herein. The one or more nucleic acid constructs, salts or solvates can at least partially silence a gene a plant or seed. The one or more nucleic acid constructs can alter a phenotype of a gene in a plant or seed.

The formulation comprising one or more nucleic acid constructs, plants, or seeds can further comprise one or more strigolactones, salts, or solvates. The formulation can further comprise one or more plant growth regulators (PGRs), salts or solvates. The formulation can further comprise one or more inhibitors of abscisic acid (ABA) biosynthesis, or any salt or solvate thereof. The formulation can further comprise one or more strigolactones, salts, or solvates and one or more plant growth regulators (PGRs), salts, or solvates. The formulation can further comprise one or more strigolactones, salts, or solvates and one or more inhibitors of abscisic acid (ABA) biosynthesis, or any salt or solvate thereof. The formulation can further comprise one or more plant growth regulators (PGRs), salts, or solvates and one or more inhibitors of abscisic acid (ABA) biosynthesis, or any salt or solvate thereof.

In some cases, the formulations disclosed herein may further comprise one or more additives to facilitate nucleic acid delivery. In some instances, the additive may be a low or high molecular weight polyamine. In some instances, the additive may be polyethylenimine (PEI). In some instances, the additive may be a polyamidoamine (PAMAM) dendrimer. In some instances, the peptide may be a derivative of a viral protein. In some instances, the additive may be a cationic peptide. In some instances, the additive may be an arginine rich peptide (e.g. TAT). In some instances, the additive may be histidine rich peptide (e.g. endoporter). In some instances, the additive may be a lytic peptide (e.g. melittin).

The formulations may comprise at least about 0.1% (w/w) of an nucleic acid construct, plant, or seed, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nucleic acid construct, plant, or seed.

The formulations may comprise less than about 95% (w/w) of an nucleic acid construct, plant, or seed, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the nucleic acid construct, plant, or seed.

The formulations may comprise about 0.1%-100% (w/w) of a nucleic acid construct, plant, or seed, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the nucleic acid construct, plant, or seed.

Plant Growth Regulators (PGRs)

The formulation can comprise one or more plant growth regulators (PGRs), salts, or solvates. PGRs can be numerous chemical substances that can influence the growth and/or differentiation of plant cells, tissues, or organs. Plant growth regulators can function as chemical messengers for intercellular communication. PGRs can include auxins, gibberellins, cytokinins, abscisic acid (ABA) and ethylene, brassinosteroids, and polyamines. They can work together coordinating the growth and/or development of cells. PGRs can elicit hydraulic enhancement of a plant. PGRs can increase the harvest yield of a plant. Auxins can comprise indole-3-acetic acid (IAA) or its derivative or chemical analog.

The formulation comprising one or more plant growth regulators (PGRs), salts, or solvates can further comprise one or more nucleic acid constructs or modified plants or seeds. The formulation comprising one or more plant growth regulators (PGRs), salts, or solvates can further comprise one or more strigolactones, salts, or solvates. The formulation comprising one or more plant growth regulators (PGRs), salts, or solvates can further comprise one or more inhibitors of abscisic acid (ABA) biosynthesis, or any salt or solvate thereof. The formulation comprising one or more plant growth regulators (PGRs), salts, or solvates can further comprise one or more nucleic acid constructs and one or more strigolactones, salts, or solvates. The formulation comprising one or more plant growth regulators (PGRs), salts, or solvates can further comprise one or more nucleic acid constructs and one or more inhibitors of abscisic acid (ABA) biosynthesis, or any salt or solvate thereof. The formulation comprising one or more plant growth regulators (PGRs), salts, or solvates can further comprise one or more strigolactones, salts, or solvates and one or more inhibitors of abscisic acid (ABA) biosynthesis, or any salt or solvate thereof.

The formulations may comprise at least about 0.1% (w/w) of a plant growth regulator (PGR), salt, or solvate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the PGR, salt, or solvate.

The formulations may comprise less than about 95% (w/w) of a PGR, salt, or solvate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the PGR, salt, or solvate.

The formulations may comprise about 0.1%-100% (w/w) of a PGR, salt, or solvate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the PGR, salt, or solvate.

Auxins (e.g., IAA)

The formulations may comprise at least about 0.1% (w/w) of an auxin (e.g., IAA), for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the auxin (e.g., IAA).

The formulations may comprise less than about 95% (w/w) of an auxin (e.g., IAA), for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the auxin (e.g., IAA).

The formulations may comprise about 0.1%-100% (w/w) of an auxin (e.g., IAA), for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the auxin (e.g., IAA).

Gibberellins

The formulations may comprise one or more gibberellins, such as GA1, GA3, GA4, GA7, GA0, ent-gibberellane, ent-kaurene, their derivatives and chemical analogs. The formulations may comprise at least about 0.1% (w/w) of a gibberellin, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the gibberellin.

The formulations may comprise less than about 95% (w/w) of a gibberellin, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the gibberellin.

The formulations may comprise about 0.1%-100% (w/w) of a gibberellin, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the gibberellin.

Cytokinins

The formulations may comprise one or more cytokinins, such as kinetin, zeatin, 6-benzylaminopurine, diphenylurea, thidiazuron, their derivatives and chemical analogs. The formulations may comprise at least about 0.1% (w/w) of a cytokinin, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the cytokinin.

The formulations may comprise less than about 95% (w/w) of a cytokinin, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the cytokinin.

The formulations may comprise about 0.1%-100% (w/w) of a cytokinin, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the cytokinin.

Excipients

The formulations disclosed herein may further comprise one or more excipients. The one or more excipients can be one or more pesticides, one or more stabilizers, one or more additives, one or more carriers, one or more dispersants, one or more fertilizer, or any combination thereof. In one example, one or more excipients comprise acetone.

The formulations disclosed herein may further comprise one or more pesticides. The pesticide may be a biopesticide. A biopesticide may be a form of a pesticide that can be based on microorganisms or natural products. A biopesticide may include naturally occurring substances that control pests (biochemical pesticides), microorganisms that control pests (microbial pesticides), and pesticidal substances produced by plants containing added genetic material (plant-incorporated protectants) or PIPs. Examples of biopesticides can include, but are not limited to, gluocosinolate, chitosan, spinosad, alkaloids, terpenoids, phenolics, pyrethroids, rotenoids, nicotinoids, strychnine, scilliroside, canola oil and baking soda. The pesticide may be an organophosphate pesticide, carbamate pesticide, organochlorine insecticide, pyrethroid pesticide, sulfonylurea pesticides, or a combination thereof. The pesticide may be a herbicide, algicide, avidicide, bactericide, fungicide, insecticide, miticide, molluscicide, nematicide, rodenticide, virucide, or a combination thereof.

The formulations may further comprise one or more stabilizers and/or other additives. The stabilizers and/or additives can include, but are not limited to, penetration agents, adhesives, anticaking agents, dyes, dispersants, wetting agents, emulsifying agents, defoamers, antimicrobials, antifreeze, pigments, colorants, buffers, and carriers. The formulations may further comprise surfactants and/or adjuvants.

The formulations may further comprise one or more carriers. Examples of carriers include, but are not limited to, solid carriers, sponges, textiles, and synthetic materials. The synthetic material may be a porous synthetic material. Additional carriers can include organic carriers, such as waxes, linolin, paraffin, dextrose granules, sucrose granules and maltose-dextrose granules. Alternatively, the carrier can be an anorganic carrier such as natural clays, kaolin, pyrophyllite, bentonite, alumina, montmorillonite, kieselguhr, chalk, diatomaceous earths, calcium phosphates, calcium and magnesium carbonates, sulphur, lime, flours or talc. The formulation may be adsorbed into the carrier. The carrier may be characterized by enabling release of the compound, salt, solvate, or formulation.

The formulations may further comprise one or more dispersants. The dispersant may be a negatively charged anion dispersant. The dispersant may be a nonionic dispersant.

The formulations may further comprise fertilizer. The fertilizer may be a chemical fertilizer. The fertilizer may be an organic fertilizer. The fertilizer may be an inorganic fertilizer. The fertilizer may be a granulated or powdered fertilizer. The fertilizer may be a liquid fertilizer. The fertilizer may be a slow-release fertilizer.

The formulations disclosed herein may be formulated as a dry sprayable formulation. Examples of dry sprayable formulations can include, but are not limited to, wettable powders and water dispersible granules. Wettable powders may comprise nucleic acid constructs that have been microionized to powder form. Wettable powders may be applied as suspended particles after dispersion into water. Water dispersible granules may consist of granules that are applied after disintegration or dispersion in water. The water dispersible granules may comprise particles within the range of 0.2 to 4 mm. Water dispersible granules may be formed by agglomeration, spray drying, or extrusion techniques.

The formulations may be formulated as a liquid sprayable formulation. Examples of liquid sprayable formulations can include, but are not limited to, soluble concentrates, suspension concentrates, emulsifiable concentrates, microemulsions, oil dispersions, and microencapsulated particles. Suspension concentrates may comprise a stable suspension of the compound, salt, solvate, or formulation in a fluid usually intended for dilution with water before use. Emulsifiable concentrates may comprise a compound, salt, solvate, or formulation with an emulsifying agent in a water insoluble organic solvate which will form an emulsion when added to water. Microemulsions may comprise a compound, salt, solvate, or formulation with an emulsifying agent in a water insoluble organic solvate which will form a solution/emulsion when added to water.

The formulations may be formulated as a dry spreadable granule formulation. The dry spreadable granule formulation may comprise soil applied granule on inert or fertilizer carriers.

The formulations may be formulated as a seed treatment or seed dressing.

The formulations may be formulated for rapid release. The formulations may be formulated for slow release.

Methods

Also disclosed herein are methods of at least partially silencing a gene in an organism, e.g., plant or seed. The methods can comprise contacting the organism with the nucleic acid constructs disclosed herein, e.g., contacting the organism such as a seed, with a solution of nucleic acid constructs, or directly administering the nucleic acid constructs to the organism such as a leaf of a plant.

The nucleic acid constructs, plants, seeds, and formulations disclosed herein may be used in agriculture. The nucleic acid constructs, plants, seeds, and formulations may be used to promote plant growth. The nucleic acid constructs and formulations disclosed herein may be used for enhancing shoot stability in plants. The nucleic acid constructs, plants, seeds, and formulations may be used for increasing transport capacity in plants. The nucleic acid constructs, plants, seeds, and formulations may be used for increasing drought tolerance of a plant.

Further disclosed herein are methods of improving agriculture comprising applying a formulation comprising a nucleic acid construct to a plant or seed, thereby improving agriculture. Improving agriculture may comprise promoting plant growth. Improving agriculture may comprise enhancing shoot stability in plants. Improving agriculture may comprise increasing transport capacity in plants. Improving agriculture may comprise increasing drought tolerance. Improving agriculture may comprise reducing an application of one or more pesticides. Improving agriculture may comprise terminating application of one or more pesticides. Improving agriculture may comprise reducing watering amounts applied to the plants. Improving agriculture may comprise reducing watering frequency to the plants. Improving agriculture may comprise controlling phytopathogenic fungi. Improving agriculture may comprise controlling unwanted plant growth. Improving agriculture may comprise controlling unwanted insect or mite infestation. Improving agriculture may comprise regulating growth of the plant. Improving agriculture may comprise promoting or stimulating activity in one or more fungi.

Further disclosed herein are methods of controlling phytopathogenic fungi and/or unwanted plant growth and/or unwanted insect or mite infestation and/or for regulating the growth of plants. The methods may comprise use of a formulation comprising a nucleic acid construct disclosed herein to act on the respective pests, their habitat or the plants to be protected from the respective pest, to the soil and/or to unwanted plants and/or the crop plants and/or their habitat.

The nucleic acid constructs described herein may increase plant growth by at least about 5%. The nucleic acid constructs may increase plant growth by at least about 10%. The nucleic acid constructs may increase plant growth by at least about 15%. The nucleic acid constructs may increase plant growth by at least about 20%. The nucleic acid constructs may increase plant growth by at least about 25%. The nucleic acid constructs may increase plant growth by at least about 30%. The nucleic acid constructs may increase plant growth by at least about 50%. The nucleic acid constructs may increase plant growth by at least about 60%, 70%, 80%, 90%, 95%, 100% or more.

The nucleic acid constructs may increase plant growth by at least about 1.5, 2, 3, 4, 5, 6, 7, 8, 9, 10, 11, 12, 13, 14, 15, 16, 17, 18, 19, 20, 25, 30, 40, 50-fold or more. The nucleic acid constructs may increase plant growth by at least about 1.5-fold or more. The nucleic acid constructs may increase plant growth by at least about 2-fold or more. The nucleic acid constructs may increase plant growth by at least about 3-fold or more. The nucleic acid constructs may increase plant growth by at least about 5-fold or more. The nucleic acid constructs may increase plant growth by at least about 10-fold or more. Plant growth may comprise secondary plant growth.

The nucleic acid constructs may enhance shoot growth by at least about 5%. The nucleic acid constructs may enhance shoot growth by at least about 10%. The nucleic acid constructs may enhance shoot growth by at least about 15%. The nucleic acid constructs may enhance shoot growth by at least about 20%. The nucleic acid constructs may enhance shoot growth by at least about 25%. The nucleic acid constructs may enhance shoot growth by at least about 30%. The nucleic acid constructs may enhance shoot growth by at least about 50%. The nucleic acid constructs may enhance shoot growth by at least about 60%, 70%, 80%, 90%, 95%, 100% or more. The nucleic acid constructs may enhance shoot growth by at least about 1.5, 2, 3, 4, 5, 6, 7, 8, 9, 10, 11, 12, 13, 14, 15, 16, 17, 18, 19, 20, 25, 30, 40, 50-fold or more.

The nucleic acid constructs may enhance shoot growth by at least about 1.5-fold or more. The nucleic acid constructs may enhance shoot growth by at least about 2-fold or more. The nucleic acid constructs may enhance shoot growth by at least about 3-fold or more. The nucleic acid constructs may enhance shoot growth by at least about 5-fold or more. The nucleic acid constructs may enhance shoot growth by at least about 10-fold or more.

The nucleic acid constructs may increase transport capacity in plants by at least about 5%. The nucleic acid constructs may increase transport capacity in plants by at least about 10%. The nucleic acid constructs may increase transport capacity in plants by at least about 15%. The nucleic acid constructs may increase transport capacity in plants by at least about 20%. The nucleic acid constructs may increase transport capacity in plants by at least about 25%. The nucleic acid constructs may increase transport capacity in plants by at least about 30%. The nucleic acid constructs may increase transport capacity in plants by at least about 50%. The nucleic acid constructs may increase transport capacity in plants by at least about 60%, 70%, 80%, 90%, 95%, 100% or more.

The nucleic acid constructs may increase transport capacity in plants by at least about 1.5, 2, 3, 4, 5, 6, 7, 8, 9, 10, 11, 12, 13, 14, 15, 16, 17, 18, 19, 20, 25, 30, 40, 50-fold or more. The nucleic acid constructs may increase transport capacity in plants by at least about 1.5-fold or more. The nucleic acid constructs may increase transport capacity in plants by at least about 2-fold or more. The nucleic acid constructs may increase transport capacity in plants by at least about 3-fold or more. The nucleic acid constructs may increase transport capacity in plants by at least about 5-fold or more. The nucleic acid constructs may increase transport capacity in plants by at least about 10-fold or more.

The nucleic acid constructs may increase drought tolerance in plants by at least about 5%. The nucleic acid constructs may increase drought tolerance in plants by at least about 10%. The nucleic acid constructs may increase drought tolerance in plants by at least about 15%. The nucleic acid constructs may increase drought tolerance in plants by at least about 20%. The nucleic acid constructs may increase drought tolerance in plants by at least about 25%. The nucleic acid constructs may increase drought tolerance in plants by at least about 30%. The nucleic acid constructs may increase drought tolerance in plants by at least about 50%. The nucleic acid constructs may increase drought tolerance in plants by at least about 60%, 70%, 80%, 90%, 95%, 100% or more.

The nucleic acid constructs may increase drought tolerance in plants by at least about 1.5, 2, 3, 4, 5, 6, 7, 8, 9, 10, 11, 12, 13, 14, 15, 16, 17, 18, 19, 20, 25, 30, 40, 50-fold or more. The nucleic acid constructs may increase drought tolerance in plants by at least about 1.5-fold or more. The nucleic acid constructs may increase drought tolerance in plants by at least about 2-fold or more. The nucleic acid constructs may increase drought tolerance in plants by at least about 3-fold or more. The nucleic acid constructs may increase drought tolerance in plants by at least about 5-fold or more. The nucleic acid constructs may increase drought tolerance in plants by at least about 10-fold or more.

The nucleic acid constructs may reduce the application of one or more pesticides. Reducing the application of one or more pesticides may comprise reducing an amount of the one or more pesticides that are applied to the plant. The amount of the one or more pesticides applied to the plant may be reduced by at least about 1%, 5%, 10%, 15%, 20%, 25%, 30%, 35%, 40%, 50%, 60%, 70%, 80%, 90%, 95%, or 100%. The amount of the one or more pesticides applied to the plant may be reduced by at least about 10%. The amount of the one or more pesticides applied to the plant may be reduced by at least about 20%. The amount of the one or more pesticides applied to the plant may be reduced by at least about 30%. The amount of the one or more pesticides applied to the plant may be reduced by at least about 50%.

Alternatively, or additionally, reducing the application of the one or more pesticides may comprise reducing a frequency of which the one or more pesticides are applied to the plant. The frequency of which the one or more pesticides are applied to the plant may be reduced by at least about 1%, 5%, 10%, 15%, 20%, 25%, 30%, 35%, 40%, 50%, 60%, 70%, 80%, 90%, 95%, or 100%. The frequency of which the one or more pesticides are applied to the plant may be reduced by at least about 10%. The frequency of which the one or more pesticides are applied to the plant may be reduced by at least about 20%. The frequency of which the one or more pesticides are applied to the plant may be reduced by at least about 30%. The frequency of which the one or more pesticides are applied to the plant may be reduced by at least about 40%. The frequency of which the one or more pesticides are applied to the plant may be reduced by at least about 50%.

Use of the nucleic acid constructs may allow a reduction in the amount of water applied to the plants. The amount of the water applied to the plant may be reduced by at least about 1%, 5%, 10%, 15%, 20%, 25%, 30%, 35%, 40%, 50%, 60%, 70%, 80%, 90%, 95%, or 100%. The amount of the water applied to the plant may be reduced by at least about 10%. The amount of the water applied to the plant may be reduced by at least about 20%. The amount of the water applied to the plant may be reduced by at least about 30%. The amount of the water applied to the plant may be reduced by at least about 50%.

Use of the nucleic acid constructs may allow a reduction in the frequency of which the water is applied to the plant. The frequency of which the water is applied to the plant may be reduced by at least about 1%, 5%, 10%, 15%, 20%, 25%, 30%, 35%, 40%, 50%, 60%, 70%, 80%, 90%, 95%, or 100%. The frequency of which the water is applied to the plant may be reduced by at least about 10%. The frequency of which the water is applied to the plant may be reduced by at least about 20%. The frequency of which the water is applied to the plant may be reduced by at least about 30%. The frequency of which the water is applied to the plant may be reduced by at least about 40%. The frequency of which the water is applied to the plant may be reduced by at least about 50%.

The compound, salt, solvate, formulation disclosed herein may be used to control phytopathogenic fungi. Improving agriculture may comprise controlling unwanted plant growth. Controlling unwanted plant growth may comprise stimulating germination activity of the unwanted plant. The unwanted plant may be a parasitic plant. The unwanted plant may be a root parasitic plant. Examples of parasitic plants can include, but are not limited to, witchweeds (*Striga* spp.), broomrapes (*Orobanche* spp, *Phehpanche* spp), *Alectra*, dodders, and mistletoes. The unwanted plant may belong to the family Orobanchaceae. The unwanted plant may be witchweed. Examples of unwanted plants can include but are not limited to bindweed, poison sumac, Japanese knotweed, crabgrass, dandelion, plantain plant, ragweed plant, ground ivy, stinging nettle, creeping thistle, poison ivy, bittersweet, tansy, wisteria, ajuga, sweet autumn clematis, barberry, lantana, butterfly bush, common privet, kudzu or English ivy. The unwanted plant may be *Orobanche* spp. The compound, salt, solvate, or formulation may be applied directly to the unwanted plant. The compound, salt, solvate, or formulation may be applied indirectly to the unwanted plant.

The nucleic acid construct or formulation disclosed herein may be used to control unwanted insect or mite infestation. Examples of insects and mites can include, but are not limited to spiders, gnats, mealybugs, whiteflies, predator mites, spider mites and aphids.

The nucleic acid construct or formulation disclosed herein may be used to regulate growth of the plant. Regulating plant growth may comprise regulating plant breeding. Regulating plant growth may comprise inhibiting shoot branching. Regulating plant growth may comprise regulating one or more plant products. Regulating plant growth may comprise inhibiting root development.

The nucleic acid construct or formulation disclosed herein may be used to promote or stimulate activity in fungi. The compound, salt, solvate, or formulation may stimulate hyphal branching activity of one or more fungi. The compound, salt, solvate, or formulation may induce spore germination of one or more fungi. The one or more fungi may be arbuscular mycorrhizal (AM) fungi.

Further disclosed herein are methods of preserving or extending the life of a plant. Generally, the method may comprise contacting the plant with a nucleic acid construct or formulation disclosed herein.

The nucleic acid construct or formulation may be used to preserve or extend the life of a cut plant. The cut plant may be a flower. The cut plant may be a tree. The cut plant may be bush or shrub. The cut plant may be a vegetable. The compound, salt, solvate, or formulation may be used to preserve or extend the life of an uncut plant. The uncut plant may be a flower. The uncut plant may be a tree. The uncut plant may be bush or shrub. The uncut plant may be a vegetable. The compound, salt, solvate, or formulation may be used to preserve or extend the life of a potted plant. The potted plant may be a flower. The potted plant may be a tree. The potted plant may be bush or shrub. The potted plant may be a vegetable.

The nucleic acid construct or formulation may be used to preserve or extend the life of a flower. Examples of flowers can include, but are not limited to, lilies, daisies, roses, marigolds, Angel's trumpet, phlox, vinca, snapdragons, toadflax, orchids, ferns, black-eyed Susans, blood flowers, blue lobelias, morning glories, poppies, calendulas, geraniums, impatiens, lantanas, larkspurs, calla lilies, hyacinths, azaleas, pointsettias, and begonias.

The nucleic acid construct or formulation may be used to preserve or extend the life of a bush or shrub. Examples of bushes and shrubs can include, but are not limited to, forsynthia, fuchsia, hibiscus, currant, lilac, rose, hydrangea, willow, magnolia, thyme, snowberry, dogwood and holly.

The nucleic acid construct or formulation may be used to preserve or extend the life of a tree. Examples of trees can include, but are not limited to, cypress, poinsettia, palm, fir, pine, spruce, cedar, oak, mulberry, chestnut, hawthorn, poplar, and maple. The tree may be a fir tree. The fir tree may be a Douglas, Balsam or Fraser fir tree. The tree may be a pine tree. The pine tree may be a Scotch or White pine tree. The tree may be a spruce tree. The spruce tree may be a White, Norway or Blue spruce tree. The tree may be a cedar tree. The cedar tree may be a Deodara or Eastern red cedar. The tree may be a cypress tree. The cypress tree may be an Arizona or Leland cypress tree.

The plant may be contacted with a nucleic acid construct or formulation disclosed herein, thereby extending or preserving the life of the plant. Contacting the plant with the nucleic acid construct or formulation may comprise administering the nucleic acid construct or formulation as a spray. Contacting the plant with the nucleic acid construct or formulation may comprise injecting the nucleic acid into the plant. Contacting the plant with the nucleic acid construct or formulation may comprise adding the plant growth material to the irrigation water of the plant. Contacting the plant with the nucleic acid construct or formulation may comprise applying the nucleic acid construct or formulation to the habitat of the plant. Contacting the plant with the nucleic acid construct or formulation may comprise adding the nucleic acid construct or formulation to a plant container (e.g., vase) and placing the plant in the plant container. Contacting the plant with the nucleic acid construct or formulation may comprise adding the nucleic acid construct or formulation to soil.

The life of the plant may be extended by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The life of the plant may be extended by at least about 20% as compared to an untreated plant. The life of the plant may be extended by at least about 30% as compared to an untreated plant. The life of the plant may be extended by at least about 40% as compared to an untreated plant. The life of the plant may be extended by at least about 50% as compared to an untreated plant. The life of the plant may be extended by at least about 55% as compared to an untreated plant. The life of the plant may be extended by at least about 60% as compared to an untreated plant. The life of the plant may be extended by at least about 65% as compared to an untreated plant. The life of the plant may be extended by at least about 70% as compared to an untreated plant. The life of the plant may be extended by at least about 75% as compared to an untreated plant. The life of the plant may be extended by at least about 80% as compared to an untreated plant. The life of the plant can be determined by measuring the growth time between initial planting of a seed of the plant to the death of the plant.

The life of the plant may be extended by at least about 6, 12, 24, 30, 36, 42, 48, 54, 60, 66, 72, 78, 84, 90, 96, 102, 108, 114, or 120 hours as compared to an untreated plant. The life of the plant may be extended by at least about 24 hours as compared to an untreated plant. The life of the plant may be extended by at least about 36 hours as compared to an untreated plant. The life of the plant may be extended by at least about 48 hours as compared to an untreated plant. The life of the plant may be extended by at least about 72 hours as compared to an untreated plant. The life of the plant may be extended by at least about 96 hours as compared to an untreated plant.

The life of the plant may be extended by at least about 1, 1.5, 2, 2.5, 3, 3.5, 4, 4.5, 5, 5.5, 6, 6.5, or 7 days as compared to an untreated plant. The life of the plant may be extended by at least about 8, 9, 10, 11, 12, 13, 14, 15, 16, 17, 18, 19, or 20 days as compared to an untreated plant. The life of the plant may be extended by at least about 1 day as compared to an untreated plant. The life of the plant may be extended by at least about 2 days as compared to an untreated plant. The life of the plant may be extended by at least about 2.5 days as compared to an untreated plant. The life of the plant may be extended by at least about 3 days as compared to an untreated plant. The life of the plant may be extended by at least about 3.5 days as compared to an untreated plant. The life of the plant may be extended by at least about 4 days as compared to an untreated plant. The life of the plant may be extended by at least about 4.5 days as compared to an untreated plant.

The life of the plant may be extended by at least about 1, 1.5, 2, 2.5, 3, 3.5, 4, 4.5, 5, 5.5, 6, 6.5, or 7 weeks as compared to an untreated plant. The life of the plant may be extended by at least about 8, 9, 10, 11, 12, 13, 14, 15, 16, 17, 18, 19, or 20 weeks as compared to an untreated plant. The life of the plant may be extended by at least about 1, 1.5, 2, 2.5, 3, 3.5, 4, 4.5, 5, 5.5, 6, 6.5, or 7 months as compared to an untreated plant. The life of the plant may be extended by at least about 8, 9, 10, 11, 12, 13, 14, 15, 16, 17, 18, 19, or 20 months as compared to an untreated plant.

Preserving or extending the life of the plant may comprise reducing wilting of the plant. Reducing wilting of the plant may comprise reducing flower or leaf rolling of the plant. The wilting of the plant may be reduced by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The wilting of the plant may be reduced by at least about 10% as compared to an untreated plant. The wilting of the plant may be reduced by at least about 30% as compared to an untreated plant. The wilting of the plant may be reduced by at least about 50% as compared to an untreated plant. The wilting of the plant may be reduced by at least about 70% as compared to an untreated plant. The wilting of the plant may be reduced by at least about 80% as compared to an untreated plant.

A sign of plant stress may include wilting of the plant. For example, stressed plants may have rolled leaves or petals. The plant growth materials disclosed herein may promote the life of the plant by reducing the wilting of the plant. Reducing the wilting of the plant may comprise delaying the wilting of the plant as compared to an untreated plant. For example, an untreated cut plant may show signs of wilting within 36 hours of being cut, however, a cut plant treated with a plant growth material may have delayed wilting. The wilting of the plant may be delayed by at least about 2, 3, 4, 5, 6, 7, 8, 9, 10, 11, 12, 13, 14, 15, 16, 17, 18, 19, 20, 21, 22, 23, or 24 hours as compared to an untreated plant. The wilting of the plant may be delayed by at least about 12 hours as compared to an untreated plant. The wilting of the plant may be delayed by at least about 24 hours as compared to an untreated plant. The wilting of the plant may be delayed by at least about 36 hours as compared to an untreated plant. The wilting of the plant may be delayed by at least about 48 hours as compared to an untreated plant.

An additional sign of plant stress may include reduced turgidity. Turgidity may refer to pressure caused by the osmotic flow of water from an area of low solute concentration outside of the cell into the cell cell's vacuole. Turgidity may be used by plants to maintain rigidity. Often, healthy plants are turgid, whereas, unhealthy plants are less turgid. Preserving or extending the life of the plant may comprise prolonging or maintaining the turgidity of the plant. The turgidity of the plant may be greater than the turgidity of an untreated plant. The turgidity of the plant may be at least about 1%, 5%, 10%, 15%, 20%, 25%, 30%, 35%, 40%, 45%, 50%, 55%, 60%, 65%, 70%, 75%, 80%, 85%, 90%, 95%, or 97% greater than the turgidity of an untreated plant. The turgidity of the plant may be at least about 10% greater than the turgidity of an untreated plant. The turgidity of the plant may be at least about 15% greater than the turgidity of an untreated plant. The turgidity of the plant may be at least about 25% greater than the turgidity of an untreated plant. The turgidity of the plant may be at least about 35% greater than the turgidity of an untreated plant. The turgidity of the plant may be at least about 45% greater than the turgidity of an untreated plant. The turgidity of the plant may be at least about 60% greater than the turgidity of an untreated plant. The turgidity of the plant may be at least about 75% greater than the turgidity of an untreated plant.

A stressed plant may also show a reduction in the turgid state. The turgid state may refer to a period of time in which the plant maintains its rigidity. The rigidity of the plant may refer to the rigidity of the stem of the plant. For example, as cut plants die, the stem of the plant may be less rigid, thereby causing the cut plant to fall over or bend. A stressed plant may be unable to hold itself upright. Preserving or extending the life of the plant may comprise prolonging the turgid state of the plant. The turgid state of the plant may be increased by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The turgid state of the plant may be increased by at least about 20% as compared to an untreated plant. The turgid state of the plant may be increased by at least about 30% as compared to an untreated plant. The turgid state of the plant may be increased by at least about 40% as compared to an untreated plant. The turgid state of the plant may be increased by at least about 50% as compared to an untreated plant.

The turgid state of the plant may be increased by at least about 2, 3, 4, 5, 6, 7, 8, 9, 10, 11, 12, 13, 14, 15, 16, 17, 18, 19, 20, 21, 22, 23, or 24 hours as compared to an untreated plant. The turgid state of the plant may be increased by at least about 6 hours as compared to an untreated plant. The turgid state of the plant may be increased by at least about 12 hours as compared to an untreated plant. The turgid state of the plant may be increased by at least about 24 hours as compared to an untreated plant.

A stressed plant may lose leaves or petals. Contacting a plant with a plant growth material may reduce or delay the loss of one or more petals or leaves of the plant. For example, an untreated plant may lose 50% of its leaves or petals, whereas a treated plant may lose 10-25% of its leaves or petals. The loss of the one or more petals of the plant may be reduced by least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to the loss of the one or more petals of an untreated plant. The loss of the one or more petals of the plant may be reduced by least about 10% as compared to the loss of the one or more petals of an untreated plant. The loss of the one or more petals of the plant may be reduced by least about 20% as compared to the loss of the one or more petals of an untreated plant. The loss of the one or more petals of the plant may be reduced by least about 35% as compared to the loss of the one or more petals of an untreated plant. The loss of the one or more petals of the plant may be reduced by least about 50% as compared to the loss of the one or more petals of an untreated plant. The loss of the one or more petals of the plant may be reduced by least about 60% as compared to the loss of the one or more petals of an untreated plant. The loss of the one or more petals of the plant may be reduced by least about 70% as compared to the loss of the one or more petals of an untreated plant.

The loss of the one or more petals of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of one or more petals of an untreated plant. The loss of the one or more petals of the plant may be delayed by at least about 25, 30, 35, 40, 45, 50, 55, 60, 65, 70, 75, 80, 85, 90, 95 or 100 hours as compared to the loss of one or more petals of an untreated plant. The loss of the one or more petals of the plant may be delayed by at least about 6 hours as compared to the loss of one or more petals of an untreated plant. The loss of the one or more petals of the plant may be delayed by at least about 12 hours as compared to the loss of one or more petals of an untreated plant. The loss of the one or more petals of the plant may be delayed by at least about 18 hours as compared to the loss of one or more petals of an untreated plant. The loss of the one or more petals of the plant may be delayed by at least about 36 hours as compared to the loss of one or more petals of an untreated plant. The loss of the one or more petals of the plant may be delayed by at least about 48 hours as compared to the loss of one or more petals of an untreated plant. The loss of the one or more petals of the plant may be delayed by at least about 60 hours as compared to the loss of one or more petals of an untreated plant. The loss of the one or more petals of the plant may be delayed by at least about 72 hours as compared to the loss of one or more petals of an untreated plant. The loss of the one or more petals of the plant may be delayed by at least about 96 hours as compared to the loss of one or more petals of an untreated plant.

A stressed plant may show signs of discoloration. The stressed plant may appear brownish. Alternatively, or additionally, the stressed plant shows a reduction in the appearance of green leaves. The chlorophyll content of the stressed plant may also be reduced. Preserving or extending the life of the plant may comprise maintaining the chlorophyll content of the plant. For example, a reduction in the chlorophyll content of an untreated plant may appear within 48 hours of being cut. However, a reduction in the chlorophyll content of a treated plant may appear after 60 hours of being cut. The chlorophyll content of the plant may be maintained for at least about 2, 3, 4, 5, 6, 7, 8, 9, 10, 11, 12, 13, 14, 15, 16, 17, 18, 19, 20, 21, 22, 23, or 24 hours. The chlorophyll content of the plant may be maintained for at least about 6 hours. The chlorophyll content of the plant may be maintained for at least about 12 hours. The chlorophyll content of the plant may be maintained for at least about 24 hours. Discoloration such as leaf firing (premature yellowing) may occur as a result of poor nutrient availability, and can be an indicator of poor plant health. For, example, leaf firing may be a result of nitrogen deficiency.

Preserving or extending the life of the plant may comprise reducing or delaying the loss of the chlorophyll content of the plant. The chlorophyll content of the plant may be greater than the chlorophyll content of an untreated plant. The chlorophyll content of the plant may be at least about 1%, 5%, 10%, 15%, 20%, 25%, 30%, 35%, 40%, 45%, or 50% greater than the content of an untreated plant. The chlorophyll content of the plant may be at least about 55%, 60%, 65%, 70%, 75%, 80%, 85%, 90%, 95% or 97% greater than the content of an untreated plant. The chlorophyll content of the plant may be at least about 20% greater than the content of an untreated plant. The chlorophyll content of the plant may be at least about 30% greater than the content of an untreated plant. The chlorophyll content of the plant may be at least about 40% greater than the content of an untreated plant. The chlorophyll content of the plant may be at least about 50% greater than the content of an untreated plant. The chlorophyll content of the plant may be at least about 60% greater than the content of an untreated plant. The chlorophyll content of the plant may be at least about 1.5, 2, 2.5, 3, 3.5, 4, 4.5, 5, 5.5, 6, 6.5, 7, 8, 9, or 10-fold greater than the content of an untreated plant. The chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold greater than the content of an untreated plant. The chlorophyll content of the plant may be at least about 2-fold greater than the content of an untreated plant. The chlorophyll content of the plant may be at least about 3-fold greater than the content of an untreated plant. The chlorophyll content of the plant may be at least about 4-fold greater than the content of an untreated plant. The chlorophyll content of the plant may be at least about 5-fold greater than the content of an untreated plant. The chlorophyll content of the plant may be at least about 10-fold greater than the content of an untreated plant.

The loss of the chlorophyll content of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of the chlorophyll content of an untreated plant. The loss of the chlorophyll content of the plant may be delayed by at least about 30, 35, 40, 45, 50, 55, 60, 65, 70, 75, 80, 85, 90, 95, or 100 hours as compared to the loss of the chlorophyll content of an untreated plant. The loss of the chlorophyll content of the plant may be delayed by at least about 6 hours as compared to the loss of the chlorophyll content of an untreated plant. The loss of the chlorophyll content of the plant may be delayed by at least about 12 hours as compared to the loss of the chlorophyll content of an untreated plant. The loss of the chlorophyll content of the plant may be delayed by at least about 24 hours as compared to the loss of the chlorophyll content of an untreated plant. The loss of the chlorophyll content of the plant may be delayed by at least about 36 hours as compared to the loss of the chlorophyll content of an untreated plant. The loss of the chlorophyll content of the plant may be delayed by at least about 48 hours as compared to the loss of the chlorophyll content of an untreated plant. The loss of the chlorophyll content of the plant may be delayed by at least about 60 hours as compared to the loss of the chlorophyll content of an untreated plant. The loss of the chlorophyll content of the plant may be delayed by at least about 72 hours as compared to the loss of the chlorophyll content of an untreated plant.

The loss of the chlorophyll content of the plant may be less than the loss of the chlorophyll content of an untreated plant. The loss of the chlorophyll content of the plant may be at least about 1%, 5%, 10%, 15%, 20%, 25%, 30%, 35%, 40%, 45%, 50%, 55%, or 60% less than the loss of the chlorophyll content of an untreated plant. The loss of the chlorophyll content of the plant may be at least about 65%, 70%, 72%, 75%, 77%, 80%, 85%, 90%, 92%, 95%, or 97% less than the loss of the chlorophyll content of an untreated plant. The loss of the chlorophyll content of the plant may be at least about 5% less than the loss of the chlorophyll content of an untreated plant. The loss of the chlorophyll content of the plant may be at least about 10% less than the loss of the chlorophyll content of an untreated plant. The loss of the chlorophyll content of the plant may be at least about 20% less than the loss of the chlorophyll content of an untreated plant. The loss of the chlorophyll content of the plant may be at least about 30% less than the loss of the chlorophyll content of an untreated plant. The loss of the chlorophyll content of the plant may be at least about 40% less than the loss of the chlorophyll content of an untreated plant. The loss of the chlorophyll content of the plant may be at least about 50% less than the loss of the chlorophyll content of an untreated plant. The loss of the chlorophyll content of the plant may be at least about 60% less than the loss of the chlorophyll content of an untreated plant.

The loss of the chlorophyll content of the plant may be at least about 1.5, 2, 2.5, 3, 3.5, 4, 4.5, 5, 5.5, 6, 6.5, 7, 7.5, 8, 8.5, 9, 9.5, or 10-fold less than the loss of the chlorophyll content of an untreated plant. The loss of the chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold less than the loss of the chlorophyll content of an untreated plant. The loss of the chlorophyll content of the plant may be at least about 2-fold less than the loss of the chlorophyll content of an untreated plant. The loss of the chlorophyll content of the plant may be at least about 3-fold less than the loss of the chlorophyll content of an untreated plant. The loss of the chlorophyll content of the plant may be at least about 5-fold less than the loss of the chlorophyll content of an untreated plant. The loss of the chlorophyll content of the plant may be at least about 10-fold less than the loss of the chlorophyll content of an untreated plant.

The nucleic acid construct or formulation may be applied directly to the plant. The nucleic acid construct or formulation may be applied to one or more parts of the plant. The one or more parts of the plant may comprise a terminal bud, flower, lateral bud, leaf blade, leaf axil, node, internode, petiole, primary root, lateral root, root hair, root cap, or a combination thereof. The formulations may be applied to the leaf blade of the plant. The formulations may be applied to the root of the plant.

Alternatively, or additionally, the nucleic acid construct or formulation can be applied to a soil. The formulation may be applied to an area around the plant. The area around the plant may comprise soil. The area around the plant may comprise an adjacent plant. The formulation may be applied to a soil before placing a plant or seed in the soil. The formulation may be applied to bacterial consortium present in the soil. The formulation may be applied with additional bacteria to supplement the natural bacterial consortium in the soil.

The nucleic acid construct or formulation may be applied to a plant that is susceptible to a parasitic weed. Examples of plants include, but are not limited to, corn, rice, sorghum, millets, and sugar cane. The plant may be corn. The plant may be tobacco. The plant may be rice.

The nucleic acid construct or formulation may improve taste or texture of an edible product of the plant. In non-limiting examples, the targeted gene may be control sugar and/or starch biosynthesis or storage. The targeted gene may control tannin biosynthesis. The targeted gene may control anthocyanin biosynthesis. The target gene may control metabolite biosynthesis.

The nucleic acid construct may improve nutritional content of the plant, for example, by increasing or decreasing sugar, starch, protein, and/or fat content of an edible product of the plant, enhancing the accumulation of vitamins and/or minerals in the plant. The targeted gene may control sugar biosynthesis, carbohydrate biosynthesis and/or storage, protein biosynthesis and/or degradation, and/or secondary metabolite biosynthesis.

The nucleic acid construct may increase the shelf life of an edible product of the plant, for example by decreasing ethylene biosynthesis in the plant. The targeted gene may control ethylene biosynthesis.

The nucleic acid construct or formulation may be applied as a seed coating. The nucleic acid construct or formulation may be applied as a seed treatment. The nucleic acid construct or formulation may be applied as a seed dressing. The nucleic acid construct or formulation may be applied as a spray. The nucleic acid construct or formulation may be applied as a foliar spray. The nucleic acid construct or formulation may be applied as a powder. The powder may be a wettable powder.

In some instances, the measurements described herein can be made at a temperature of about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 31, 32, 33, 34, 35, 36, 37, 38, 39, or 40° C.

Kits

Also provided are kits that find use in practicing the subject methods, as mentioned above. A kit can include one or more of the compositions described herein. A kit can include at least nucleic acid construct. A kit can include at least one engineered plant or seed.

A kit can include one or more reagents for performing administration of nucleic acid constructs to plants or seeds (e.g., polynucleotides, buffers, cations, etc.), and the like. Additional reagents that are desired in the protocol to be practiced with the kit components may be present. Such additional reagents include, but are not limited to, one or more of the following an enzyme or combination of enzymes such as a polymerase, reverse transcriptase, nickase, restriction endonuclease, uracil-DNA glycosylase enzyme, enzyme that methylates or demethylates DNA, endonuclease, ligase, etc.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, such as printed information on a suitable medium or substrate (e.g., a piece or pieces of paper on which the information is printed), in the packaging of the kit, in a package insert, etc. Yet another means would be a computer readable medium (e.g., diskette, CD, etc.), on which the information has been recorded. Yet another means that may be present is a website address which may be used via the internet to access the information at a removed site.

Communicating Results

The present disclosure provides the communication of assay results or diagnoses or both to technicians, physicians or subjects, for example. In certain instances, computers will be used to communicate results of the methods herein to interested parties, e.g., customers, technicians, physicians and their subjects, etc. In some instances, the methods can be performed, or results analyzed in a country or jurisdiction which differs from the country or jurisdiction to which the results are communicated. In some instances, a result may be communicated to the subject as soon as possible after the diagnosis is obtained. The results may be sent to a subject by email or communicated to the subject by phone. A computer may be used to communicate the result by email or phone. In certain instances, the message containing result may be generated and delivered automatically to the subject using a combination of computer hardware and software which will be familiar to artisans skilled in telecommunications. In certain instances or some of the method steps, including the preparation of plants and seeds, and communicating of assay results, may be carried out in diverse (e.g., foreign) jurisdictions.

The section headings used herein are for organizational purposes only and are not to be construed as limiting the subject matter described.

It is to be understood that the methods and compositions described herein are not limited to the particular methodology, protocols, cell lines, constructs, and reagents described herein and as such may vary. It is also to be understood that the terminology used herein is for the purpose of describing particular instances only, and is not intended to limit the scope of the methods and compositions described herein, which will be limited only by the appended claims. While preferred instances of the present disclosure have been shown and described herein, it will be obvious to those skilled in the art that such instances are provided by way of example only. Numerous variations, changes, and substitutions will now occur to those skilled in the art without departing from the disclosure. It should be understood that various alternatives to the instances of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any instance can be combined with any other instance. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

EXAMPLES

Example 1—Preparation of CATS Oligonucleotide Nucleic Acid Construct Solutions

Oligonucleotides were custom synthesized. 96 well oligo plates were obtained; one plate for each locu of interest. Pooled stocks for each oligo plate were made by taking 20 uL of a 400 uM stock from each well of that plate and combining these in a 2 mL tube. Afterwards, each pooled sock was combined in a 12 mL sterile falcon tube, mixed by pipetting, and briefly centrifuged to collect all contents. This pooled oligo mix was then pipetted into two eight-well PCT strip tubes and spun down. Tubes were placed in a PTC-200 Thermal cycler at 95 degrees for 1 minute to denature contents, and then cooled at room temperature for 10 minutes. Contents of strip tubes were again combined in a fresh sterile 12 mL falcon tube, mixed by pipetting and centrifuged briefly to collect contents. Applications of serial dilution of this full-strength oligo mix were applied to plants. Representative sequences of oligonucleotides are shown in SEQ ID NOs 1-664.

Example 2—Application of CATS Nucleotides to Plants and Seeds

Vacuum Treatment Method in Corn

Five 20 mL clear glass scintillation vials were obtained, and six B73 Maize seeds were place in each vial, lying flat. Seeds in vials 1~4 received 900 uL of an oligo treatment (full strength, 1/10, 1/100, and 1/1000, respectively) and seeds in vial 5 received 900 uL of water. After incubating for 20 minutes, caps were removed from all five vials, which were then placed in an airtight chamber and vacuumed 18 hours at 400 mbar. After 18 hours, vials were removed from the vacuum and each seed was planted in 100 $mm^2$ plastic pot filled with moistened Sunshine Mix No. 4. Seeds were left to germinate under next light Veg 8 LED panels set to long day conditions.

Germination and Outgrowth in Solution Method

Five 20 mL clear glass scintillation vials were obtained, and six B73 Maize seeds were placed in each vial, lying flat. Seeds in vials 1~4 received 900 uL of an oligo treatment (full strength, 1/10, 1/100, and 1/1000, respectively) and seeds in vial 5 received 900 uL of water. Vials were placed in the dark with caps on and seeds were left to germinate, for 4 days. Once epicotyls had emerged, vials were removed from dark, embryos were removed from treatment solutions, and each was planted in 100 $mm^2$ plastic pot filled with moistened Sunshine Mix No. 4.

Syringe Infiltration Method

CATS oligonucleotide solutions described above can be administered directly to plant tissue by syringe in order to locally deliver the oligonucleotides to a particular location on the plant.

Example 3—Targeting the Phytoene Desaturase (PDS1) in Maize

CATS oligonucleotides were constructed in to target the phytoene desaturase, an enzyme involved in the synthesis of carotenoids in plants. Mutations or knockouts of this gene result in albino phenotypes.

Figure 3:
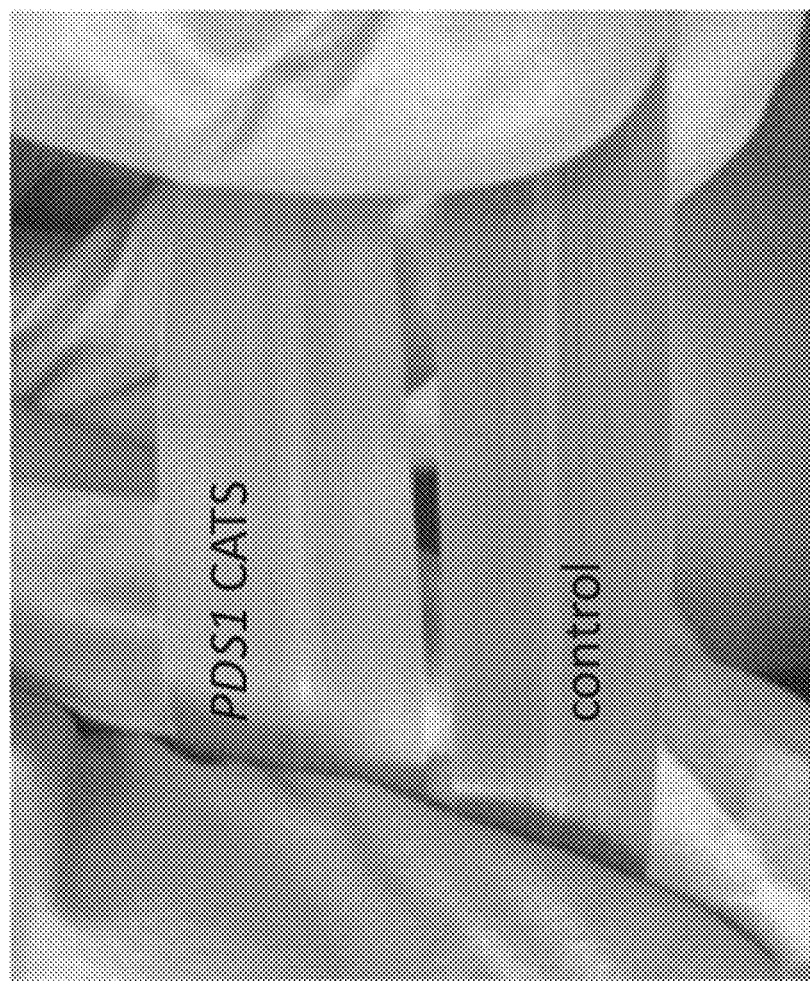
FIG. 3 depicts the result of silencing a PDS1 gene in maize by treatment with CATS oligonucleotides. PDS1-CATS plants show a pale green leaf phenotype (upper leaf), as compared to a control maize plant (lower leaf).

A total of 62 oligonucleotides (31 oligonucleotide pairs, shown in SEQ ID NOs:1-62) were synthesized targeting transcription regulatory regions upstream of PDS1 gene open reading frame in a maize plant. The mixture of oligonucleotides was applied to maize seeds, and seedlings grown from the seeds. PDS1-CATS plants showed pale green leaf phenotype compared to the uncontacted control plants (FIG. 3).

Figure 4:
FIG. 4 depicts the results of silencing a PDS1 gene in maize plants by treatment with CATS oligonucleotides using an infiltration administration method.

Administration of CATS oligonucleotides directly to a maize leaf by syringe infiltration results in local loss of pigmentation (FIG. 4).

Confirmation of DNA Methylation by Bisulfite Sequencing

Figure 5:
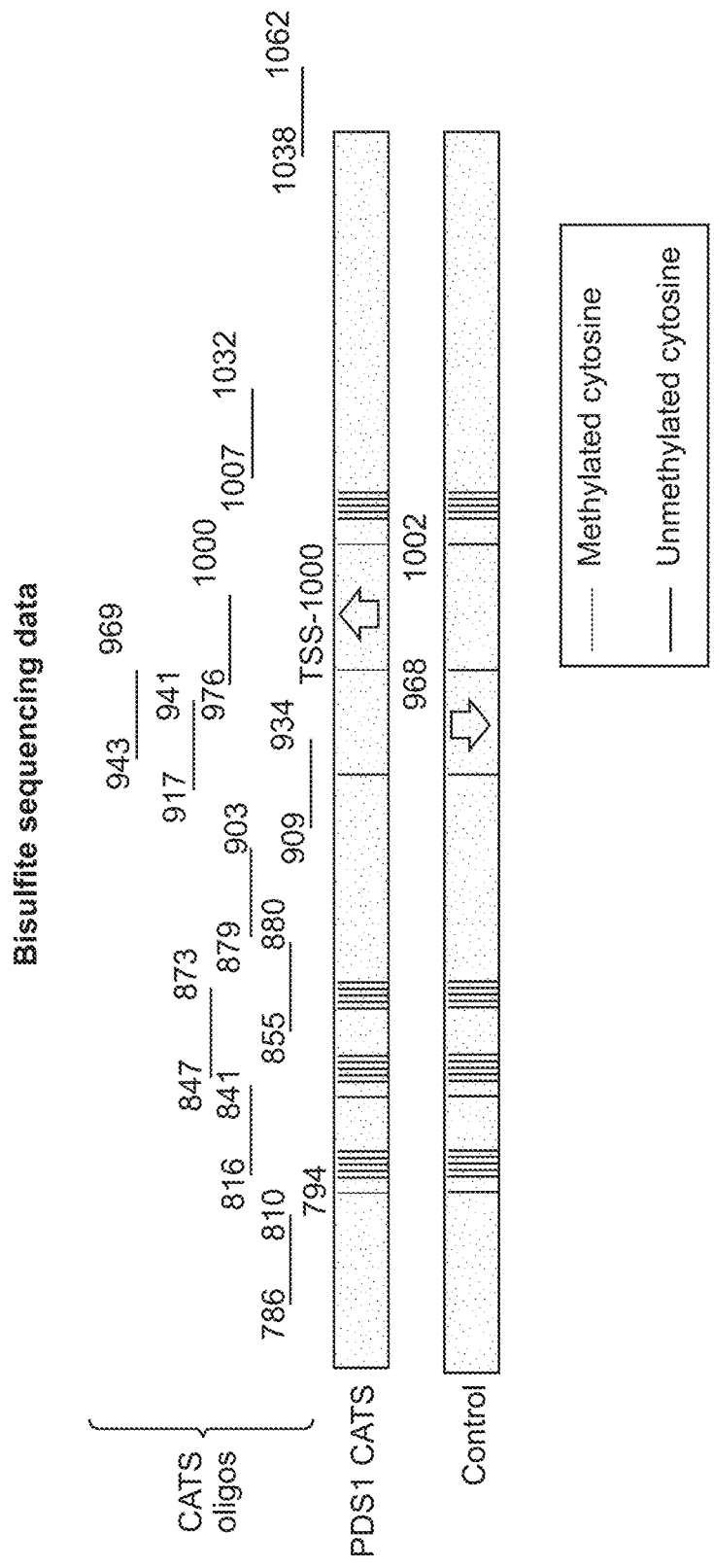
FIG. 5 depicts bisulfate sequencing analysis of a PDS1 gene in CATS-treated maize plants. Treatment with CATS oligonucleotides results in methylated cytosines upstream of the PDS1 open reading frame.

Leaf tissue from sterile scissors were cut and placed in a chilled (LN2) closed cap tube with one medium glass bead. Leaf tissue was bead beated for 1:30 at 1800 RPN. DNA was extracted using the PureLink Plant Total DNA extraction kit. A total of 20 μL of DNA from the extraction was used with Zymo Research Corp Easy DNA Methylation kit. Human standards were used to confirm the kit was working. Primers were designed using MethPrimer2 (http://www.urogene.org/cgi-bin/methprimer2/MethPrimer.cgi) and allowing degeneracy in the primers if necessary. Bi-sulfite treated DNA from the kit was used to perform a PCR reaction using 12.5 μL Zymotaq, 1 μL primer-F, 1 μL primer-R, 4 μL BS treated DNA and 7.5 μL water. The first set of BS-PCR primers were amplified at 50° C. and cover GC islands. Amplicons were sequence cloned to confirm. Initial analysis of the sequenced data indicates that some of the cytosines were methylated (FIG. 5).

Example 4—Targeting the LZY1 Gravitropism Regulator in Maize

The plant regulator Lazy1 (LZY1) is known to control the plant's shoot gravitropism. In wildtype plants, shoots grow in the opposite direction of gravity and respond to changes in orientation by bending to maintain this directionality. In contrast, mutants in LZY1 expression do not respond to changes in orientation. CATS oligos were designed to target the LZY1 regulator. A total of 132 oligonucleotides (67 oligonucleotide pairs, shown in SEQ ID NOs: 63-194) were synthesized targeting transcription regulatory regions upstream of LZY1 gene open reading frame in a maize plant. The mixture of oligonucleotides was applied to maize seeds, and seedlings grown from the seeds.

Figure 6B:
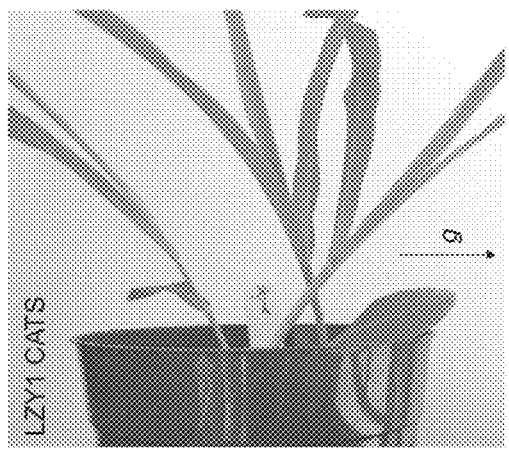
FIGS. 6A-6D depict the result of silencing a LZY1 gene in maize by treatment with CATS oligonucleotides.
Figure 6D:
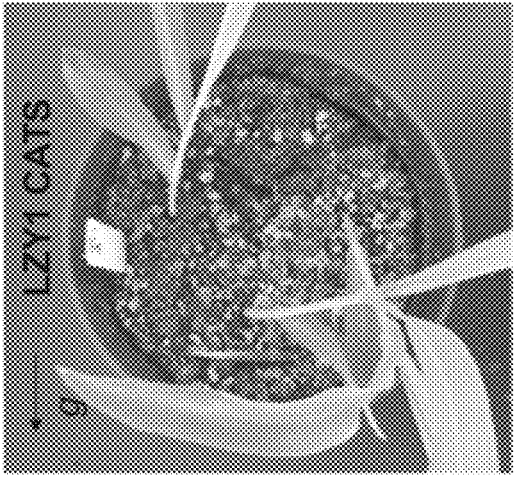
Figure 6A:
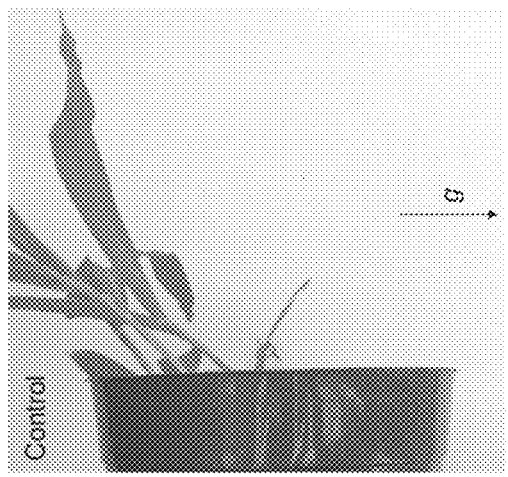
Figure 6C:
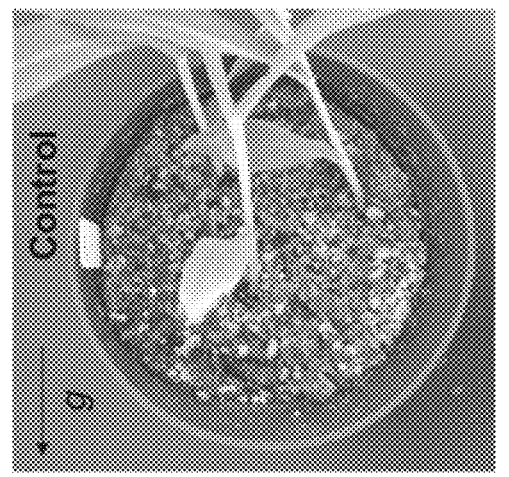

As shown in FIGS. 6B and 6D, CATS::LZY1 seedlings display reduced or absent gravitropism when turned on their side, as compared to unmodified plants (FIGS. 6A and 6C), where the control plants display a strong gravitropic response.

Example 5—Targeting Polyphenol Oxidases in Potato

Figure 7A:
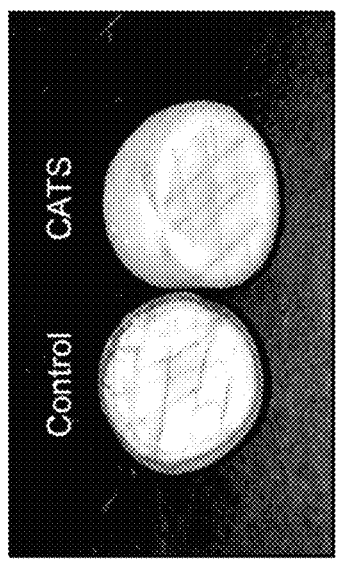
FIGS. 7A-7C depict the result of silencing a polyphenol oxidase (PPO) gene in potato plants.
Figure 7C:
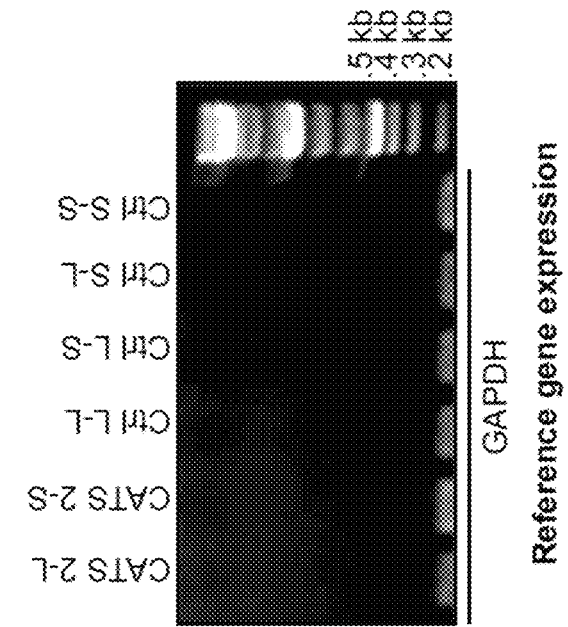
Figure 7B:
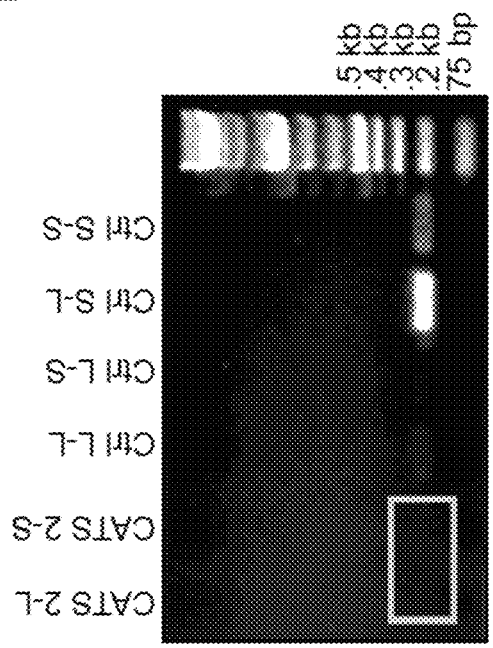

The polyphenol enzyme oxidase (PPO) enzymes in plants are responsible for the enzymatic browning phenotype that occurs after cutting or wounding of the plant. Non-browning crops are desirable from a consumer acceptance and food waste perspective. To achieve non-browning potatoes, CATS oligos were designed to simultaneously target the 7 PPO alleles in potato (*Solanum tuberosum*). A total of 210 individual oligos (105 oligo pairs, shown in SEQ ID NOs: 195-404) were applied to seed potatoes using the 'outgrowth in solution' method above. Plants were grown in greenhouse conditions and tubers were harvested approximately 3 months after planting. RT-PCT analysis of PPO mRNA levels indicated that CATS plants had reduced levels of the transcript (FIG. 7B), and phenotype analysis shows that tubers from CATS plants had greatly reduced enzymatic browning when cut, as compared to the potatoes of unmodified control plants (FIG. 7A).

Example 6—Creation of Short Stature Corn

Figure 8:
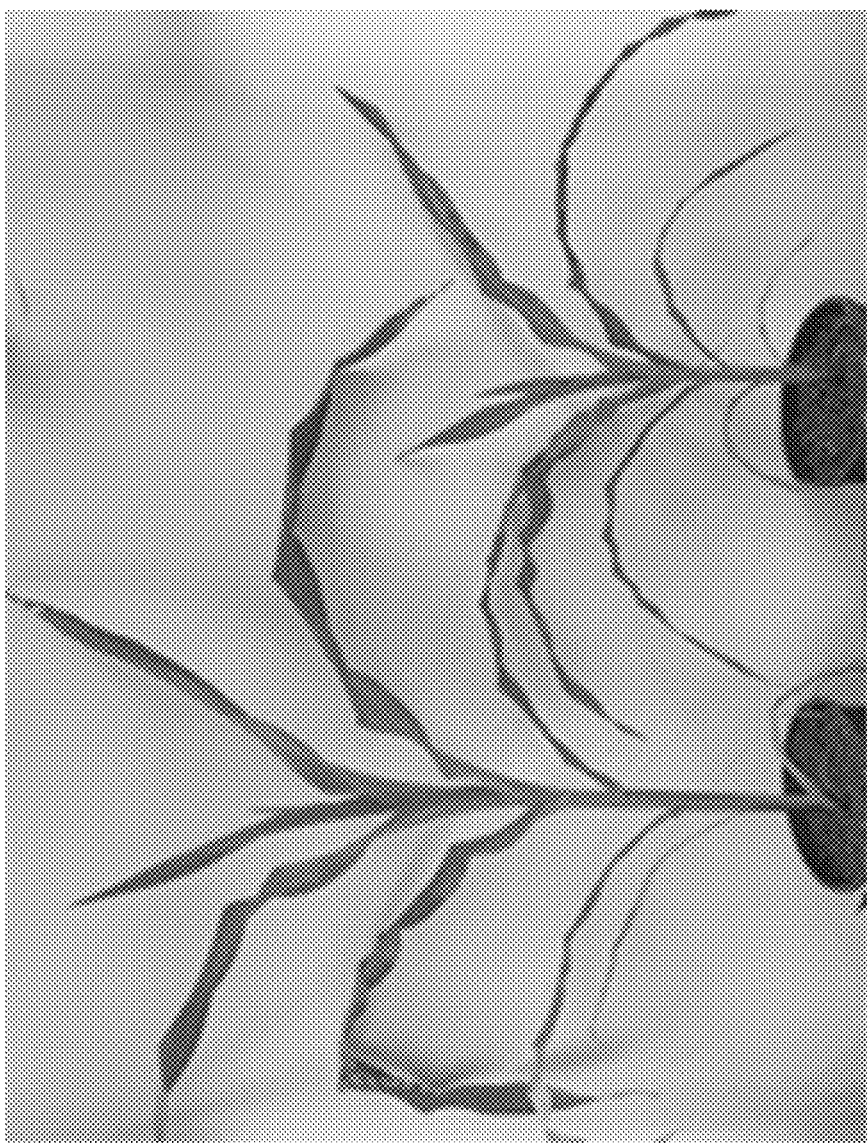
FIG. 8 depicts the result of silencing BWF1 and BR2 genes in maize. Treatment with CATS oligonucleotides targeting BWF1 and BR2 results in shorter maize plants compared to an untreated control plant.

CATS oligos were designed to target genes involved in the biosynthesis of brassinosteroids and involved in the gibberellin-brassinosteroid balance (BWF1 and BR2). A total of 180 individual oligos (90 oligo pairs, shown in SEQ ID NOs: 405-584) were applied to maize seeds. Plants grown from contacted seeds were shorter than control plants not contacted with the CATS oligos (FIG. 8).

Example 7—Targeting the Old Gold Gene in a Population of Tomato Plants

Oligo Treatment and Plant Growth Conditions

Oligos were designed to target the microTom genome (~500 bp upstream and downstream of the Old Gold translation start site, shown in SEQ ID NOs: 585-684) with non-overlapping oligos across this ~1 kb region. Complementary oligos were annealed by incubating at 95° C. for 10 mins with gradual cooling to room temperature, then annealed oligo pairs were pooled for each treatment. Seeds were incubated with 900 ul of oligos at 250 μM concentration (0.5×TE buffer) either targeting Old Gold (treated) or with random oligos as a control (untreated). Seeds were incubated at room temperature in the dark for 3 days before planting in Sunshine Mix soil #4 and grown under 16 hr photoperiods until two true leaves had established (~2 weeks). 50-100 mg of true leaf tissue was harvested from each sample that emerged and frozen in liquid nitrogen before being stored at −80 for later analysis.

RNA Isolation

Total RNA isolation from the starting material was collected using the PureLink Pro 96 total RNA Purification Kit (ThermoFisher Scientific) according to the manufacturer's instructions. Total RNA was eluted in RNase free water. Samples with tissue that were unable to be isolated were discarded. Total RNA was quantified using the Quant-iT™ RNA Assay Kit, broad range, (ThermoFisher Scientific) using fluorescence on the SpectraMax iD3 plate reader. Quantified total RNA was diluted to 1 ng using RNase free water. RNA lower than 1 ng/uL were discarded. After isolation and quantification were complete, there were population sizes of 40 samples of 1 KB treatment; 45 samples of 2.5 KB; 44 samples of RO (random oligonucleotides) control; and 11 samples of Water control.

Quantitative Real-Time PCR Conditions

RT-qPCR was carried out in a 96-well optical plate using Quantstudios 6 Flex Real-Time PCR Systems (Applied Biosystems). Reactions were performed using Luna Universal One-Step RT-qPCR Kit, which uses Luna WarmStart Reverse Transcriptase and SYBR Green I (New England Biolabs); 10 μM of each primer; RNase free water; and 1 μL of diluted RNA (1 ng/uL) in a final volume of 20 μL. The following thermal cycling conditions were used for all amplifications (following the Luna Universal One-Step RT-qPCR Kit manual): 55° C. for 10 minutes for reverse transcription, 95° C. for 1 minute for denaturation, 40 amplification cycles of 95° C. for 10 seconds and 60° C. for 1 minute, and a melt curve of various stages of 60-95° C. All samples were prepared in technical triplicates and three non template controls of RNase free water for each qPCR plate.

Data Analysis

Figure 10:
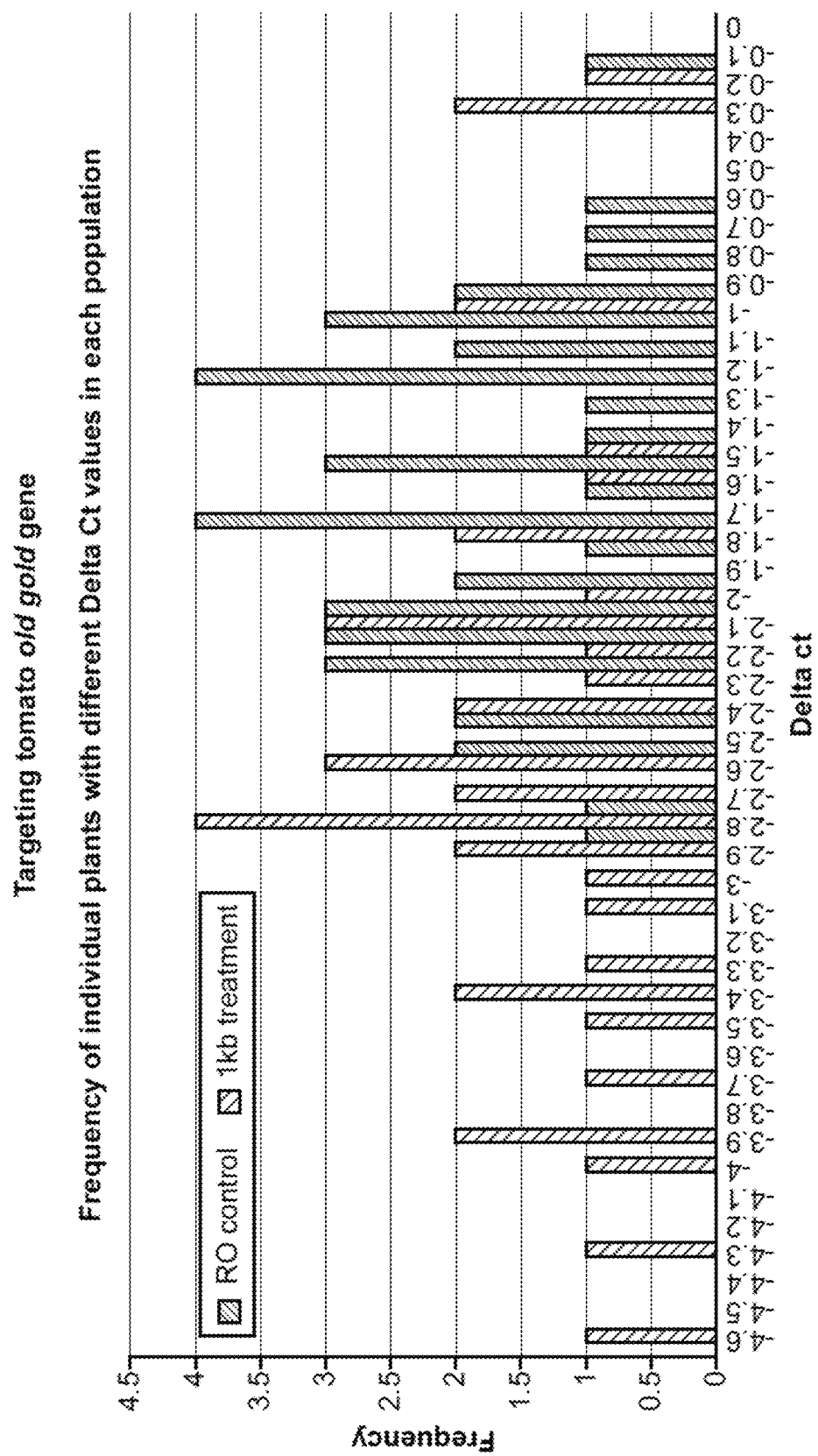
FIG. 10 depicts using CATS oligonucleotides to target the old gold gene in the tomato plant. The 1 kb treatment can decrease the gene expression in individual plants compared to the R0 control.

Threshold cycle (Ct) values were averaged from 3 technical replicates of each sample during RT-qPCR and used to calculate the ΔCt value (Old Gold target—GAPDH housekeeping reference). Changes in gene expression for treated (Old Gold) vs untreated (random oligo) populations are displayed as frequency histograms (FIG. 10). ΔCt values for each sample were rounded to 2 d.p. and sorted into groups with a class width of 0.1, ranging from 0 to −4.5 ΔCt (log 2), with more negative ΔCt values indicating greater down-regulation of Old Gold target gene compared to GAPDH reference gene.

Example 8—Examples of Sequence Modifications for Oligonucleotides

Figure 9:
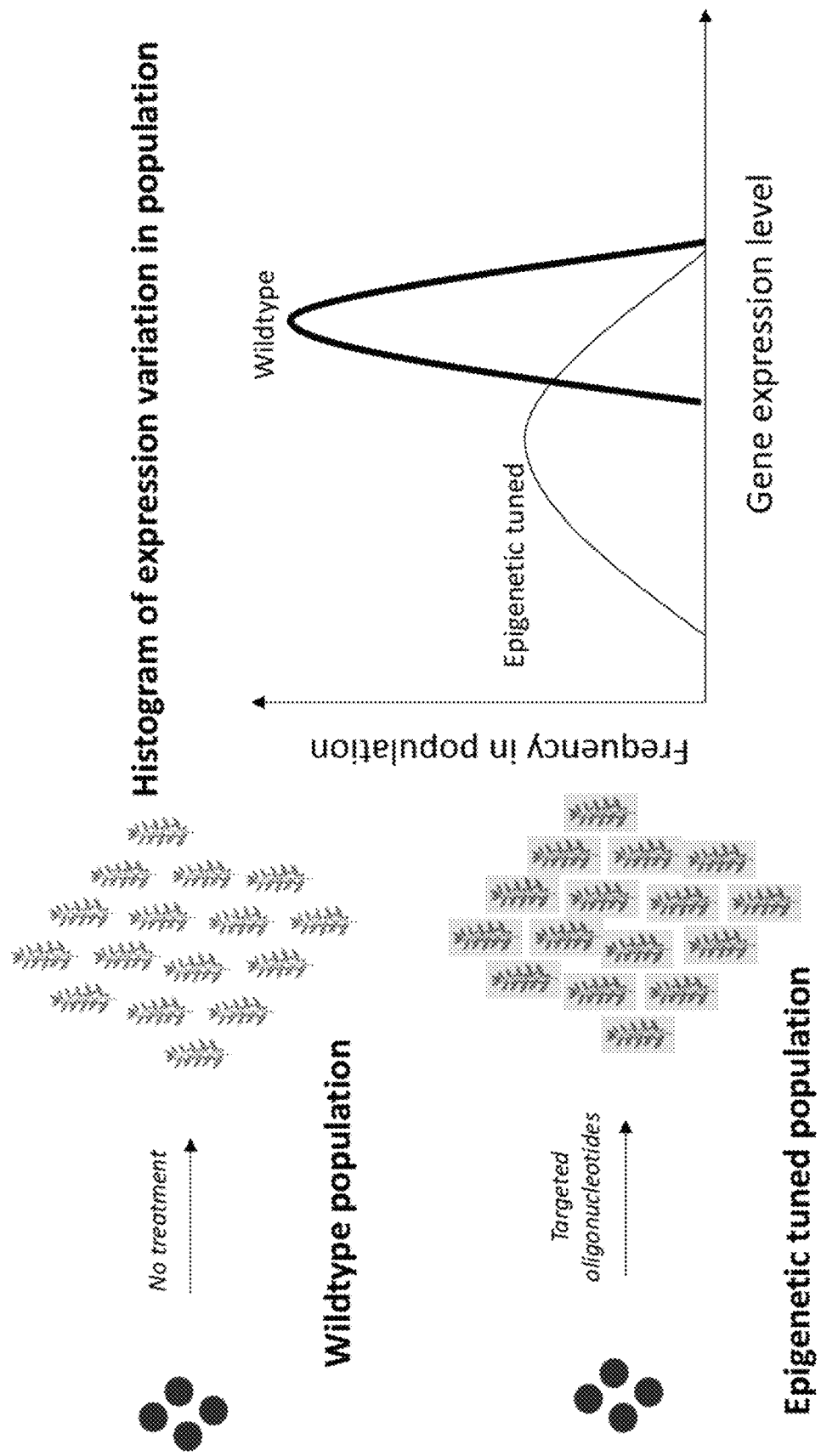
FIG. 9 depicts using epigenetic methods to create variable populations compared to wildtype populations. The population treated with the epigenetic method can have decreased gene expression compared to the wildtype population.

Nucleic acid constructs disclosed herein for example CATs oligonucleotides can have various modifications in individual or multiple locations. These modifications can include but are not limited to phosphorothioate modifications, 2'O-Methyl modifications, 2'Fluoro modifications, or any combination thereof. An example is shown in FIG. 11. An epigenetic modification using constructs herein such as CATs oligonucleotides can create populations with variable gene expression levels (FIG. 9).

| Sequences | |
|---|---|
| CATS oligonucleotide sequences for silencing PDS1 gene (mC = 2'-O-methyl cytosine, mG = 2'-O-methyl guanine, mA = 2'-O-methyl adenine, mT = 2'-O-methylt hymine, mU = 2'-O-methyl uracil) | |
| SEQ ID NO: 1 | TGGCTACTATGTATTGATGTTAAmC |
| SEQ ID NO: 2 | TTAACATCAATACATAGTAGCCAmG |
| SEQ ID NO: 3 | CCATTAAGATGTACTCGCTCTGTmA |
| SEQ ID NO: 4 | ACAGAGCGAGTACATCTTAATGGmA |
| SEQ ID NO: 5 | TAATCATTTTTGTCTGTTATTTTmU |
| SEQ ID NO: 6 | AAAATAACAGACAAAAATGATTAmC |
| SEQ ID NO: 7 | GTCTATATTCAGACAGATGATAAmU |
| SEQ ID NO: 8 | TTATCATCTGTCTGAATATAGACmA |
| SEQ ID NO: 9 | CTAGACACATATACCAAGTAATGmA |
| SEQ ID NO: 10 | CATTACTTGGTATATGTGTCTAGmA |
| SEQ ID NO: 11 | GGATATAGGGAGTATGAACAACTmG |
| SEQ ID NO: 12 | AGTTGTTCATACTCCCTATATCCmU |
| SEQ ID NO: 13 | CAATTAGTTCCGTATTGATAATAmU |
| SEQ ID NO: 14 | TATTATCAATACGGAACTAATTGmU |
| SEQ ID NO: 15 | GGATCGACGTATTTATAATAATAmC |
| SEQ ID NO: 16 | TATTATTATAAATACGTCGATCCmA |
| SEQ ID NO: 17 | TGTTCTATATCTATATTTAATTAmU |
| SEQ ID NO: 18 | TAATTAAATATAGATATAGAACAmG |
| SEQ ID NO: 19 | GCGGAGGTCTCCACTCTTCTCTCmU |
| SEQ ID NO: 20 | GAGAGAAGAGTGGAGACCTCCGCmA |
| SEQ ID NO: 21 | CCATCTTATCATCGCCCACGTACmA |
| SEQ ID NO: 22 | GTACGTGGGCGATGATAAGATGGmA |
| SEQ ID NO: 23 | CCCAATTCCTCGCAACTGGGCTCmC |
| SEQ ID NO: 24 | GAGCCCAGTTGCGAGGAATTGGGmU |
| SEQ ID NO: 25 | CGCCTCCACGACACTGCCCCCCGmC |
| SEQ ID NO: 26 | CGGGGGGCAGTGTCGTGGAGGCGmG |
| SEQ ID NO: 27 | CAAGTCCGCCGCCTCCATTCTTCmA |
| SEQ ID NO: 28 | GAAGAATGGAGGCGGCGGACTTGmA |
| SEQ ID NO: 29 | GTGCGTTGGTGGGTCTGAAACAATmA |
| SEQ ID NO: 30 | ATTGTTTCAGACCCACCAACGCACmA |
| SEQ ID NO: 31 | GTCTCAAAAGGAGGTGAGCTGGGmA |
| SEQ ID NO: 32 | CCCAGCTCACCTCCTTTTGAGACmG |
| SEQ ID NO: 33 | TTTAGCCGACTAATTTTAGATGAmG |
| SEQ ID NO: 34 | TCATCTAAAATTAGTCGGCTAAAmU |
| SEQ ID NO: 35 | TAATCTTTAGTTCCGTGCCCCCGmC |
| SEQ ID NO: 36 | CGGGGGCACGGAACTAAAGATTAmU |
| SEQ ID NO: 37 | TGCAGGCTCACCCCGACGTGCCCmC |
| SEQ ID NO: 38 | GGGCACGTCGGGGTGAGCCTGCAmC |
| SEQ ID NO: 39 | GCCCTCCGCGCGCGATGCCCCCAmU |
| SEQ ID NO: 40 | TGGGGGCATCGCGCGCGGAGGGCmA |
| SEQ ID NO: 41 | CACCGACGCAGAGCTCGCCCATGmC |
| SEQ ID NO: 42 | CATGGGCGAGCTCTGCGTCGGTGmU |
| SEQ ID NO: 43 | CACGTGCCCCGGCGGCGTCGCGAmU |
| SEQ ID NO: 44 | TCGCGACGCCGCCGGGGCACGTGmC |
| SEQ ID NO: 45 | TATCCCCGCCGTCGCGCGCCTACmG |
| SEQ ID NO: 46 | GTAGGCGCGCGACGGCGGGGATAmC |
| SEQ ID NO: 47 | GTACCTGGAGCAGAAGCGATTTCmG |
| SEQ ID NO: 48 | GAAATCGCTTCTGCTCCAGGTACmA |
| SEQ ID NO: 49 | TGCCGAGGAGCTCACCGCTGTGAmA |
| SEQ ID NO: 50 | TCACAGCGGTGAGCTCCTCGGCAmA |
| SEQ ID NO: 51 | TAGTCCCGTCCCCTCCAGGTCCTmG |
| SEQ ID NO: 52 | AGGACCTGGAGGGGACGGGACTAmA |
| SEQ ID NO: 53 | AATTCACTTGTGTATTCCCCCGAmA |
| SEQ ID NO: 54 | TCGGGGAATACACAAGTGAATTmG |
| SEQ ID NO: 55 | GAGACAGTCTGCACGGCTCCTATmC |
| SEQ ID NO: 56 | ATAGGAGCCGTGCAGACTGTCTCmG |
| SEQ ID NO: 57 | GCATGTACCCAATACCCTGTTTTmG |
| SEQ ID NO: 58 | AAAACAGGGTATTGGGTACATGCmU |
| SEQ ID NO: 59 | TGACCTTGGGTACTATTATAGCAmC |
| SEQ ID NO: 60 | TGCTATAATAGTACCCAAGGTCAmA |
| SEQ ID NO: 61 | TTTCAGTTCGAGTGTTAGACCCTmG |

| | Sequences |
|---|---|
| SEQ ID NO: 62 | AGGGTCTAACACTCGAACTGAAAmC |

CATS oligonucleotide sequences for silencing LZY1 gene (mC = 2'-O-methyl cytosine, mG = 2'-O-methyl guanine, mA = 2'-O-methyl adenine, mT = 2'-O-methyl thymine, mU = 2'-O-methyl uracil)

| | Sequences |
|---|---|
| SEQ ID NO: 63 | CTTTTTGGAATTCTTCTGACCAGmG |
| SEQ ID NO: 64 | CTGGTCAGAAGAATTCCAAAAAGmA |
| SEQ ID NO: 65 | CAAGAAAATTAAGGATATATAGCmG |
| SEQ ID NO: 66 | GCTATATATCCTTAATTTTCTTGmG |
| SEQ ID NO: 67 | TAAGGCATGTCGATAATAAAGACmU |
| SEQ ID NO: 68 | GTCTTTATTATCGACATGCCTTAmG |
| SEQ ID NO: 69 | ATAGGACCGAGCAACTCGGATTCmG |
| SEQ ID NO: 70 | GAATCCGAGTTGCTCGGTCCTATmU |
| SEQ ID NO: 71 | GACTCGGACTTGGACTGTGCAACmU |
| SEQ ID NO: 72 | GTTGCACAGTCCAAGTCCGAGTCmA |
| SEQ ID NO: 73 | AGCCGGGATACTCAAAATCGAAAmU |
| SEQ ID NO: 74 | TTTCGATTTTGAGTATCCCGGCTmG |
| SEQ ID NO: 75 | ACTCGGTCCATAGGTTAATACTCmA |
| SEQ ID NO: 76 | GAGTATTAACCTATGGACCGAGTmC |
| SEQ ID NO: 77 | TCATATTTTACATCTAAACGTTCmG |
| SEQ ID NO: 78 | GAACGTTTAGATGTAAAATATGAmG |
| SEQ ID NO: 79 | TGGAAGCAAACACCCCCTTAGACmG |
| SEQ ID NO: 80 | GTCTAAGGGGTGTTTGCTTCCAmC |
| SEQ ID NO: 81 | CCACCTCTTGTCGACCATTTGTAmG |
| SEQ ID NO: 82 | TACAAATGGTCGACAAGAGGTGGmU |
| SEQ ID NO: 83 | CATGTTCCGTTCTGCCGACTGATmG |
| SEQ ID NO: 84 | ATCAGTCGGCAGAACGGAACATGmA |
| SEQ ID NO: 85 | CCTGCAGCTGCAGCTGCAGTGCGmU |
| SEQ ID NO: 86 | CGCACTGCAGCTGCAGCTGCAGGmA |
| SEQ ID NO: 87 | ACTCCATCGTCTATTAATGGCTCmG |
| SEQ ID NO: 88 | GAGCCATTAATAGACGATGGAGTmA |
| SEQ ID NO: 89 | CCAGCGCTCGGCTTAGACAAGCCmU |
| SEQ ID NO: 90 | GGCTTGTCTAAGCCGAGCGCTGGmA |
| SEQ ID NO: 91 | ATGAAGGTCAGTCAGTAGTCCCAmC |
| SEQ ID NO: 92 | TGGGACTACTGACTGACCTTCATmG |
| SEQ ID NO: 93 | AGCTTTTAGTCTAGCTCGACAGTmC |
| SEQ ID NO: 94 | ACTGTCGAGCTAGACTAAAAGCTmG |
| SEQ ID NO: 95 | TTCTTTCTAATCCACCTATTTTCmU |
| SEQ ID NO: 96 | GAAAATAGGTGGATTAGAAAGAAmC |
| SEQ ID NO: 97 | GCGACTCACTCTCGTAGTTGGTGmU |
| SEQ ID NO: 98 | CACCAACTACGAGAGTGAGTCGCmC |
| SEQ ID NO: 99 | TCATGACCTCCTCCTCAAGCTCGmG |
| SEQ ID NO: 100 | CGAGCTTGAGGAGGAGGTCATGmA |
| SEQ ID NO: 101 | CTCATATTTGAAGCCTCCTTGTTmC |
| SEQ ID NO: 102 | AACAAGGAGGCTTCAAATATGAGmA |
| SEQ ID NO: 103 | AGAAAGCATCGACCTTAGCAAGGmU |
| SEQ ID NO: 104 | CCTTGCTAAGGTCGATGCTTTCTmU |
| SEQ ID NO: 105 | TTGTCCATGCGCTTGGTGAGGTCmG |
| SEQ ID NO: 106 | GACCTCACCAAGCGCATGGACAAmG |
| SEQ ID NO: 107 | AATCTAACCTTTGAGTACCAAATmG |
| SEQ ID NO: 108 | ATTTGGTACTCAAAGGTTAGATTmG |
| SEQ ID NO: 109 | TGGAGACACATACACAGAAGAmA |
| SEQ ID NO: 110 | TCTTCTCTGTGTATGTGTCTCCAmU |
| SEQ ID NO: 111 | CTTGTTTGGATTGAAACCATTACmA |
| SEQ ID NO: 112 | GTAATGGTTTCAATCCAAACAAGmA |
| SEQ ID NO: 113 | ATATATTGGACTTGTATTCCAAGmC |
| SEQ ID NO: 114 | CTTGGAATACAAGTCCAATATATmA |
| SEQ ID NO: 115 | GTCCTTATAGATTTGGACACTTAmU |
| SEQ ID NO: 116 | TAAGTGTCCAAATCTATAAGGACmU |
| SEQ ID NO: 117 | CAAATCTTCTTGCCTAAGCAAATmU |
| SEQ ID NO: 118 | ATTTGCTTAGGCAAGAAGATTTGmU |
| SEQ ID NO: 119 | CTAAACTCTATTTTATACTCCCTmC |
| SEQ ID NO: 120 | AGGGAGTATAAAATAGAGTTTAGmU |
| SEQ ID NO: 121 | AGTGTTCATTTTGGCTCCTCATTmU |
| SEQ ID NO: 122 | AATGAGGAGCCAAAATGAACACTmA |
| SEQ ID NO: 123 | TCAGATGGATGAAAATGAATCTAmG |
| SEQ ID NO: 124 | TAGATTCATTTTCATCCATCTGAmA |
| SEQ ID NO: 125 | TGAATCCACTGATATGTTAAAACmG |
| SEQ ID NO: 126 | GTTTTAACATATCAGTGGATTCAmU |
| SEQ ID NO: 127 | GGGACGGAGAGAGTATATTCCAAmG |
| SEQ ID NO: 128 | TTGGAATATACTCTCTCCGTCCCmA |
| SEQ ID NO: 129 | CTATCTTTGGGTTTTCATCTTTTmU |
| SEQ ID NO: 130 | AAAAGATGAAAACCCAAAGATAGmC |
| SEQ ID NO: 131 | GACCAGGAGGGACTCTATTTATAmU |
| SEQ ID NO: 132 | TATAAATAGAGTCCCTCCTGGTCmA |
| SEQ ID NO: 133 | GATAATAAAGACTCTGACTAATAmG |
| SEQ ID NO: 134 | TATTAGTCAGAGTCTTTATTATCmG |
| SEQ ID NO: 135 | AGACTCTGACTAATAGGACCGAGmC |

-continued

| | Sequences |
|---|---|
| SEQ ID NO: 136 | CTCGGTCCTATTAGTCAGAGTCTmU |
| SEQ ID NO: 137 | ACTAATAGGACCGAGCAACTCGGmA |
| SEQ ID NO: 138 | CCGAGTTGCTCGGTCCTATTAGTmC |
| SEQ ID NO: 139 | GACCGAGCAACTCGGATTCGGTGmG |
| SEQ ID NO: 140 | CACCGAATCCGAGTTGCTCGGTCmC |
| SEQ ID NO: 141 | AACTCGGATTCGGTGGAGTGACTmC |
| SEQ ID NO: 142 | AGTCACTCCACCGAATCCGAGTTmG |
| SEQ ID NO: 143 | TTCGGTGGAGTGACTCGGACTTGmG |
| SEQ ID NO: 144 | CAAGTCCGAGTCACTCCACCGAAmU |
| SEQ ID NO: 145 | AGTGACTCGGACTTGGACTGTGCmA |
| SEQ ID NO: 146 | GCACAGTCCAAGTCCGAGTCACTmC |
| SEQ ID NO: 147 | GGACTTGGACTGTGCAACTCGGAmU |
| SEQ ID NO: 148 | TCCGAGTTGCACAGTCCAAGTCCmG |
| SEQ ID NO: 149 | ACTGTGCAACTCGGATTCAGCCGmG |
| SEQ ID NO: 150 | CGGCTGAATCCGAGTTGCACAGTmC |
| SEQ ID NO: 151 | ACTCGGATTCAGCCGGGATACTCmA |
| SEQ ID NO: 152 | GAGTATCCCGGCTGAATCCGAGTmU |
| SEQ ID NO: 153 | TCAGCCGGGATACTCAAAATCGAmA |
| SEQ ID NO: 154 | TCGATTTTGAGTATCCCGGCTGAmA |
| SEQ ID NO: 155 | GATACTCAAAATCGAAATCCAAGmG |
| SEQ ID NO: 156 | CTTGGATTTCGATTTTGAGTATCmC |
| SEQ ID NO: 157 | AAATCGAAATCCAAGGGACTCGGmU |
| SEQ ID NO: 158 | CCGAGTCCCTTGGATTTCGATTTmU |
| SEQ ID NO: 159 | ATCCAAGGGACTCGGTCCATAGGmU |
| SEQ ID NO: 160 | CCTATGGACCGAGTCCCTTGGATmU |
| SEQ ID NO: 161 | GACTCGGTCCATAGGTTAATACTmC |
| SEQ ID NO: 162 | AGTATTAACCTATGGACCGAGTCmC |
| SEQ ID NO: 163 | TCATATTTTACATCTAAACGTTCmG |
| SEQ ID NO: 164 | GAACGTTTAGATGTAAAATATGAmG |
| SEQ ID NO: 165 | TACATCTAAACGTTCGATGTGCGmU |
| SEQ ID NO: 166 | CGCACATCGAACGTTTAGATGTAmA |
| SEQ ID NO: 167 | AACGTTCGATGTGCGTGGAAGCAmA |
| SEQ ID NO: 168 | TGCTTCCACGCACATCGAACGTTmU |
| SEQ ID NO: 169 | ATGTGCGTGGAAGCAAACACCCCmC |
| SEQ ID NO: 170 | GGGGTGTTTGCTTCCACGCACATmC |
| SEQ ID NO: 171 | GGAAGCAAACACCCCCTTAGACGmU |
| SEQ ID NO: 172 | CGTCTAAGGGGGTGTTTGCTTCCmA |
| SEQ ID NO: 173 | ACACCCCCTTAGACGTGGGACACmC |

| | Sequences |
|---|---|
| SEQ ID NO: 174 | GTGTCCCACGTCTAAGGGGTGTmU |
| SEQ ID NO: 175 | TTAGACGTGGGACACCACCTCTTmG |
| SEQ ID NO: 176 | AAGAGGTGGTGTCCCACGTCTAAmG |
| SEQ ID NO: 177 | GGGACACCACCTCTTGTCGACCAmU |
| SEQ ID NO: 178 | TGGTCGACAAGAGGTGGTGTCCCmA |
| SEQ ID NO: 179 | ACCTCTTGTCGACCATTTGTAGCmC |
| SEQ ID NO: 180 | GCTACAAATGGTCGACAAGAGGTmG |
| SEQ ID NO: 181 | TCGACCATTTGTAGCCTTCTTCAmU |
| SEQ ID NO: 182 | TGAAGAAGGCTACAAATGGTCGAmC |
| SEQ ID NO: 183 | TTGTAGCCTTCTTCATGTTCCGTmU |
| SEQ ID NO: 184 | ACGGAACATGAAGAAGGCTACAAmA |
| SEQ ID NO: 185 | TTCTTCATGTTCCGTTCTGCCGAmC |
| SEQ ID NO: 186 | TCGGCAGAACGGAACATGAAGAAmG |
| SEQ ID NO: 187 | GTTCCGTTCTGCCGACTGATGGAmU |
| SEQ ID NO: 188 | TCCATCAGTCGGCAGAACGGAACmA |
| SEQ ID NO: 189 | CTGCCGACTGATGGATCACTCCTmG |
| SEQ ID NO: 190 | AGGAGTGATCCATCAGTCGGCAGmA |
| SEQ ID NO: 191 | TGATGGATCACTCCTGCAGCTGCmA |
| SEQ ID NO: 192 | GCAGCTGCAGGAGTGATCCATCAmG |
| SEQ ID NO: 193 | CACTCCTGCAGCTGCAGCTGCAGmU |
| SEQ ID NO: 194 | CTGCAGCTGCAGCTGCAGGAGTGmA |

CATS oligonucleotide sequences for silencing PPO gene (mC = 2'-O-methyl cytosine, mG = 2'-O-methyl guanine, mA = 2'-O-methyl adenine, mT = 2'-O-methyl thymine, mU = 2'-O-methyl uracil)

| | |
|---|---|
| SEQ ID NO: 195 | ATGAAGCAAAACTCTAAAGTTGAmC |
| SEQ ID NO: 196 | TCAACTTTAGAGTTTTGCTTCATmA |
| SEQ ID NO: 197 | AACCCAGTTTTTCAGCTCTCACTmA |
| SEQ ID NO: 198 | AGTGAGAGCTGAAAAACTGGGTTmG |
| SEQ ID NO: 199 | ATTACCAATTGATCATCATCTTGmC |
| SEQ ID NO: 200 | CAAGATGATGATCAATTGGTAATmU |
| SEQ ID NO: 201 | ATTACAACTTTCCAGCTATTTTGmC |
| SEQ ID NO: 202 | CAAAATAGCTGGAAAGTTGTAATmA |
| SEQ ID NO: 203 | CACTTTATAATCCTAATCCTACAmC |
| SEQ ID NO: 204 | TGTAGGATTAGGATTATAAAGTGmU |
| SEQ ID NO: 205 | AAGCTCATTCAACAACACAATTAmG |
| SEQ ID NO: 206 | TAATTGTGTTGTTGAATGAGCTTmU |
| SEQ ID NO: 207 | TCAAACACAAAATAGAGTTATGGmC |
| SEQ ID NO: 208 | CCATAACTCTATTTTGTGTTTGAmU |
| SEQ ID NO: 209 | TTAACTTCATGTACTACCATTTCmC |

| | |
|---|---|
| SEQ ID NO: 210 | GAAATGGTAGTACATGAAGTTAAmA |
| SEQ ID NO: 211 | CATCCAAAATTTTCGTCCGTCCAmA |
| SEQ ID NO: 212 | TGGACGGACGAAAATTTTGGATGmG |
| SEQ ID NO: 213 | CGATAACTTTAAGGTGAATTGTGmA |
| SEQ ID NO: 214 | CACAATTCACCTTAAAGTTATCGmA |
| SEQ ID NO: 215 | TAATGAAGGAAAATCTTTTCCAGmG |
| SEQ ID NO: 216 | CTGGAAAAGATTTTCCTTCATTAmU |
| SEQ ID NO: 217 | GATAGACGAAATGTCCTCCTTGGmU |
| SEQ ID NO: 218 | CCAAGGAGGACATTTCGTCTATCmA |
| SEQ ID NO: 219 | GGCTCTATGGAGCATCTAATCTTmA |
| SEQ ID NO: 220 | AAGATTAGATGCTCCATAGAGCCmC |
| SEQ ID NO: 221 | AACCAACGAGCCATTTGCCCTAGmG |
| SEQ ID NO: 222 | CTAGGGCAAATGGCTCGTTGGTTmA |
| SEQ ID NO: 223 | GTACCACCCCAGACTTCTCAACmA |
| SEQ ID NO: 224 | GTTGAGAAGTCTGGGGGTGGTACmC |
| SEQ ID NO: 225 | TCTGTCAACCGACCCAACCGACCmC |
| SEQ ID NO: 226 | GGTCGGTTGGGTCGGTTGACAGMA |
| SEQ ID NO: 227 | TCCAGACTGTAAGTTATTTTTCTmG |
| SEQ ID NO: 228 | AGAAAAATAACTTACAGTCTGGAmU |
| SEQ ID NO: 229 | CAGAGCTTCTAAGAACAAAAACTmU |
| SEQ ID NO: 230 | AGTTTTTGTTCTTAGAAGCTCTGmU |
| SEQ ID NO: 231 | GTATGGCTGCTATACAAAATTCCmC |
| SEQ ID NO: 232 | GGAATTTTGTATAGCAGCCATACmA |
| SEQ ID NO: 233 | CGCTTCCTGGAATAATTGATATGmG |
| SEQ ID NO: 234 | CATATCAATTATTCCAGGAAGCGmG |
| SEQ ID NO: 235 | TATTATATAAGGCAAGGTATAGCmC |
| SEQ ID NO: 236 | GCTATACCTTGCCTTATATAATAmA |
| SEQ ID NO: 237 | TCATTCAAAACCTAGCAATAATGmG |
| SEQ ID NO: 238 | CATTATTGCTAGGTTTTGAATGAmA |
| SEQ ID NO: 239 | GTAGTAATACATCTCTCAAAACTmC |
| SEQ ID NO: 240 | AGTTTTGAGAGATGTATTACTACmU |
| SEQ ID NO: 241 | TTCTTCCTCCACTTCTTTATCTTmC |
| SEQ ID NO: 242 | AAGATAAAGAAGTGGAGGAAGAAmG |
| SEQ ID NO: 243 | AAGCCCTCTTCAACTTTTCATCCmA |
| SEQ ID NO: 244 | GGATGAAAAGTTGAAGAGGGCTTmA |
| SEQ ID NO: 245 | CGTACCAAATGTTCAAAGTTTCmU |
| SEQ ID NO: 246 | TGAAACTTTGAACATTTGGTACGmU |
| SEQ ID NO: 247 | TACCAATAATAACGGTGACCAAmA |
| SEQ ID NO: 248 | TTTGGTCACCGTTATTATTGGTAmA |
| SEQ ID NO: 249 | GTTGAAACGAATTCTGTTGATCGmA |
| SEQ ID NO: 250 | CGATCAACAGAATTCGTTTCAACmG |
| SEQ ID NO: 251 | TTCTTCTTGGCTTAGGTGGTCTTmU |
| SEQ ID NO: 252 | AAGACCACCTAAGCCAAGAAGAAmC |
| SEQ ID NO: 253 | TGCTAATGCTATACCATTAGCTGmC |
| SEQ ID NO: 254 | CAGCTAATGGTATAGCATTAGCmA |
| SEQ ID NO: 255 | AATTATCAATGCTTGTGAATCTCmG |
| SEQ ID NO: 256 | GAGATTCACAAGCATTGATAATTmU |
| SEQ ID NO: 257 | TGTTAAAAATTTCCTCACCTACmC |
| SEQ ID NO: 258 | GTAGGTGAGGAAATTTTTAACAmA |
| SEQ ID NO: 259 | GAATTGTTCGATATGAGATCGAGmC |
| SEQ ID NO: 260 | CTCGATCTCATATCGAACAATTCmG |
| SEQ ID NO: 261 | TGGAGTAATATTTTATTTGGCTCmC |
| SEQ ID NO: 262 | GAGCCAAATAAAATATTACTCCAmU |
| SEQ ID NO: 263 | TATATAAGGCAATGTATAGCCCTmA |
| SEQ ID NO: 264 | AGGGCTATACATTGCCTTATATAmA |
| SEQ ID NO: 265 | TCATCCAAAAACTAGCAATGGCmA |
| SEQ ID NO: 266 | TGCCATTGCTAGTTTTTGGATGAmA |
| SEQ ID NO: 267 | TAATAGTAGTAGTACCACTCTCAmA |
| SEQ ID NO: 268 | TGAGAGTGGTACTACTACTATTAmC |
| SEQ ID NO: 269 | TTTACTTCTTCCTCCACTTCTTTmA |
| SEQ ID NO: 270 | AAAGAAGTGGAGGAAGAAGTAAmA |
| SEQ ID NO: 271 | CTCCTAAGCCCTCTCAACTTTTCmC |
| SEQ ID NO: 272 | GAAAAGTTGAGAGGGCTTAGGAGmU |
| SEQ ID NO: 273 | ACGTAACAAAACGTTCAAAGTTTmC |
| SEQ ID NO: 274 | AAACTTTGAACGTTTTGTTACGTmU |
| SEQ ID NO: 275 | GTTACCAATAATAACGGTGACCAmA |
| SEQ ID NO: 276 | TGGTCACCGTTATTATTGGTAACmC |
| SEQ ID NO: 277 | ACGTTGAAACGAATTCTGTTGATmC |
| SEQ ID NO: 278 | ATCAACAGAATTCGTTTCAACGTmU |
| SEQ ID NO: 279 | TGTTCTTCTTGGTTTAGGAGGTCmU |
| SEQ ID NO: 280 | GACCTCCTAAACCAAGAAGAACAmU |
| SEQ ID NO: 281 | GTTGCTAATGCTATACCATTAGCmU |
| SEQ ID NO: 282 | GCTAATGGTATAGCATTAGCAACmA |
| SEQ ID NO: 283 | CTTCTCCAACTCCACCTCCTGATmC |
| SEQ ID NO: 284 | ATCAGGAGGTGGAGTTGGAGAAGmC |
| SEQ ID NO: 285 | CCAAACAATCTGTTCAGCTATTCmA |
| SEQ ID NO: 286 | GAATAGCTGAACAGATTGTTTGGmU |

| | |
|---|---|
| SEQ ID NO: 287 | AAATGTGTAAAAGATTTCCCACAmC |
| SEQ ID NO: 288 | TGTGGGAAATCTTTTACACATTTmU |
| SEQ ID NO: 289 | TCAAAAACCTCCCACCTACCGCGmU |
| SEQ ID NO: 290 | CGCGGTAGGTGGGAGGTTTTTGAmA |
| SEQ ID NO: 291 | TGTTGGAGTGGTAGGTGAGCCTCmU |
| SEQ ID NO: 292 | GAGGCTCACCTACCACTCCAACAmU |
| SEQ ID NO: 293 | AGCAACATACTATATAATGCAAGmG |
| SEQ ID NO: 294 | CTTGCATTATATAGTATGTTGCTmA |
| SEQ ID NO: 295 | TATGAATCTTCATCAACCAAAGmC |
| SEQ ID NO: 296 | CTTTTGGTTGATGAAGATTCATAmU |
| SEQ ID NO: 297 | AATGGCAAGTGTGTGCAATAGTAmG |
| SEQ ID NO: 298 | TACTATTGCACACACTTGCCATTmG |
| SEQ ID NO: 299 | ACTACAACTCTCAAAACTCCTTTmC |
| SEQ ID NO: 300 | AAAGGAGTTTTGAGAGTTGTAGTmA |
| SEQ ID NO: 301 | CCAATACTTCTTTATCTTCAACTmC |
| SEQ ID NO: 302 | AGTTGAAGATAAAGAAGTATTGGmA |
| SEQ ID NO: 303 | CTCTCAACTTTTCCTCCATGGAAmA |
| SEQ ID NO: 304 | TTCCATGGAGGAAAAGTTGAGAGmG |
| SEQ ID NO: 305 | CAAATGTTCAAAGTTTCATGCAAmG |
| SEQ ID NO: 306 | TTGCATGAAACTTTGAACATTTGmG |
| SEQ ID NO: 307 | ATAATAACGGTGACCAAAACGTTmG |
| SEQ ID NO: 308 | AACGTTTTGGTCACCGTTATTATmU |
| SEQ ID NO: 309 | TTCTGTTGATCGAAGAAATGTTCmU |
| SEQ ID NO: 310 | GAACATTTCTTCGATCAACAGAAmU |
| SEQ ID NO: 311 | TTAGGAGGTCTATATGGTGTTGCmU |
| SEQ ID NO: 312 | GCAACACCATATAGACCTCCTAAmA |
| SEQ ID NO: 313 | TACCATTAGCTGCATCCGCTGCTmC |
| SEQ ID NO: 314 | AGCAGCGGATGCAGCTAATGGTAmU |
| SEQ ID NO: 315 | GATCAAAGGATGGCTAAATTTTTmC |
| SEQ ID NO: 316 | AAAAATTTAGCCATCCTTTGATCmA |
| SEQ ID NO: 317 | TTGAACTTGAGGATCAATATTTCmC |
| SEQ ID NO: 318 | GAAATATTGATCCTCAAGTTCAAmA |
| SEQ ID NO: 319 | GAGAGTGAGTAATTACTCCAAGAmU |
| SEQ ID NO: 320 | TCTTGGAGTAATTACTCACTCTCmU |
| SEQ ID NO: 321 | ACAATTATCACCAACGTGTTACAmC |
| SEQ ID NO: 322 | TGTAACACGTTGGTGATAATTGTmA |
| SEQ ID NO: 323 | GCTACATATACCTTCACCATTTTmG |
| SEQ ID NO: 324 | AAAATGGTGAAGGTATATGTAGCmA |
| SEQ ID NO: 325 | GCAACTCTTCTAACAAAAAATCAmC |
| SEQ ID NO: 326 | TGATTTTTGTTAGAAGAGTTGCmA |
| SEQ ID NO: 327 | AACACAATGTCTTCTTCTAGTACmU |
| SEQ ID NO: 328 | GTACTAGAAGAAGACATTGTGTTmG |
| SEQ ID NO: 329 | TTCCATTATGCACCAACAAATCCmC |
| SEQ ID NO: 330 | GGATTTGTTGGTGCATAATGGAAmG |
| SEQ ID NO: 331 | TTCCTTCACCACCAACAACTCATmC |
| SEQ ID NO: 332 | ATGAGTTGTTGGTGGTGAAGGAAmG |
| SEQ ID NO: 333 | TCAAACCCTCTCAACTTTTCCTmC |
| SEQ ID NO: 334 | AGGAAAAGTTGAGAGGGTTTTGAmU |
| SEQ ID NO: 335 | GACGTAATCAAAGTTTCAAGGTTmU |
| SEQ ID NO: 336 | AACCTTGAAACTTTGATTACGTCmU |
| SEQ ID NO: 337 | CGTCAACAATAATGTTGGCGAGCmA |
| SEQ ID NO: 338 | GCTCGCCAACATTATTGTTGACGmU |
| SEQ ID NO: 339 | AACCTTGACGCTGTTGATAGGCmA |
| SEQ ID NO: 340 | CGCCTATCAACAGCGTCAAGGTTmU |
| SEQ ID NO: 341 | TTTTAGGGTTAGGAGGTCTTTATmG |
| SEQ ID NO: 342 | ATAAAGACCTCCTAACCCTAAAAmG |
| SEQ ID NO: 343 | TAATCTTGCACCATTAGCCTCTGmC |
| SEQ ID NO: 344 | CAGAGGCTAATGGTGCAAGATTAmG |
| SEQ ID NO: 345 | TGCAAAAGAAAATAGGATCTGCAmU |
| SEQ ID NO: 346 | TGCAGATCCTATTTTCTTTTGCAmU |
| SEQ ID NO: 347 | ATACAAAACCATTTCAAAACTGCmG |
| SEQ ID NO: 348 | GCAGTTTTGAAATGGTTTTGTATmU |
| SEQ ID NO: 349 | CGTTTGTACTAGGTACATGAATTmU |
| SEQ ID NO: 350 | AATTCATGTACCTAGTACAAACGmU |
| SEQ ID NO: 351 | AAATACTGATGAAACGCTGCAAAmG |
| SEQ ID NO: 352 | TTTGCAGCGTTTCATCAGTATTTmA |
| SEQ ID NO: 353 | ACTCATCCCAGCAATGGCTTCTTmC |
| SEQ ID NO: 354 | AAGAAGCCATTGCTGGGATGAGTmG |
| SEQ ID NO: 355 | CCTTTGTGCACTACCAATATTCCmC |
| SEQ ID NO: 356 | GGAATATTGGTAGTGCACAAAGGmU |
| SEQ ID NO: 357 | TCTCCAATAATACCAACTCATCTmU |
| SEQ ID NO: 358 | AGATGAGTTGGTATTATTGGAGAmA |
| SEQ ID NO: 359 | AAAACCCTCTCAGCTTTTCCTCCmA |
| SEQ ID NO: 360 | GGAGGAAAAGCTGAGAGGGTTTTmG |
| SEQ ID NO: 361 | CGTAGTCAAAGTTTCAAGGTTTCmA |
| SEQ ID NO: 362 | GAAACCTTGAAACTTTGACTACGmC |
| SEQ ID NO: 363 | ATAGCGAGCATGACAAAAATAACmC |

| | |
|---|---|
| SEQ ID NO: 364 | GTTATTTTTGTCATGCTCGCTATmA |
| SEQ ID NO: 365 | CGATGCTGTTGATAGGAGAAATGmU |
| SEQ ID NO: 366 | CATTTCTCCTATCAACAGCATCGmU |
| SEQ ID NO: 367 | GGGTTAGGAGGTCTTTATGGTGCmU |
| SEQ ID NO: 368 | GCACCATAAAGACCTCCTAACCCmU |
| SEQ ID NO: 369 | TTGCACCATTAGCCACTGCTGCTmC |
| SEQ ID NO: 370 | AGCAGCAGTGGCTAATGGTGCAAmG |
| SEQ ID NO: 371 | ACCACCTGATTTGAAAACTTGTAmG |
| SEQ ID NO: 372 | TACAAGTTTTCAAATCAGGTGGTmG |
| SEQ ID NO: 373 | ACTGTAACTCCTGGTGGTCCAGCmA |
| SEQ ID NO: 374 | GCTGGACCACCAGGAGTTACAGTmG |
| SEQ ID NO: 375 | TATGTGCTCACGTGGACACATTAmC |
| SEQ ID NO: 376 | TAATGTGTCCACGTGAGCACATAmG |
| SEQ ID NO: 377 | GATGCAATATTTATGATGTTCACmG |
| SEQ ID NO: 378 | GTGAACATCATAAATATTGCATCmA |
| SEQ ID NO: 379 | ATTATATTCTCGACAAGTTGAACmG |
| SEQ ID NO: 380 | GTTCAACTTGTCGAGAATATAATmU |
| SEQ ID NO: 381 | GGAAATGATGGAGATTATTATGGmU |
| SEQ ID NO: 382 | CCATAATAATCTCCATCATTTCCmA |
| SEQ ID NO: 383 | TCTTCCTCACAAGGTAATTACAAmA |
| SEQ ID NO: 384 | TTGTAATTACCTTGTGAGGAAGAmA |
| SEQ ID NO: 385 | CCTTAGCTTGCTCCATATTATTCmU |
| SEQ ID NO: 386 | GAATAATATGGAGCAAGCTAAGGmA |
| SEQ ID NO: 387 | TGCTAGCCCTAGATGTTCATGAAmU |
| SEQ ID NO: 388 | TTCATGAACATCTAGGGCTAGCAmU |
| SEQ ID NO: 389 | CAAGCAAAAAATGTCTTCCATTmC |
| SEQ ID NO: 390 | AATGGAAGACATTTTTTTGCTTGmU |
| SEQ ID NO: 391 | CACTACCAATACTCTCTCTTCTTmC |
| SEQ ID NO: 392 | AAGAAGAGAGTATTGGTAGTGmG |
| SEQ ID NO: 393 | ACCACTTTTTCCAACTTGCATTCmU |
| SEQ ID NO: 394 | GAATGCAAGTTGGAAAAAGTGGTmG |
| SEQ ID NO: 395 | GCAAAAACATCAAAAATTTCCTCmC |
| SEQ ID NO: 396 | GAGGAAATTTTTGATGTTTTTGCmA |
| SEQ ID NO: 397 | AGCATAATGTCCATCGTAATTTCmC |
| SEQ ID NO: 398 | GAAATTACGATGGACATTATGCTmU |
| SEQ ID NO: 399 | GCAAAACCATAGATGATAATAGTmC |
| SEQ ID NO: 400 | ACTATTATCATCTATGGTTTTGCmA |
| SEQ ID NO: 401 | CAATAACTCACCCATCGACATTTmC |
| SEQ ID NO: 402 | AAATGTCGATGGGTGAGTTATTGmU |
| SEQ ID NO: 403 | ACAATATGATCGATAGAAGAAACmG |
| SEQ ID NO: 404 | GTTTCTTCTATCGATCATATTGTmU |

CATS oligonucleotide sequences for silencing DWF1 and BR2 genes (mC = 2'-O-methyl cytosine, mG = 2'-O-methyl guanine, mA = 2'-O-methyl adenine, mT = 2'-O-methyl thymine, mU = 2'-O-methyl uracil)

| | |
|---|---|
| SEQ ID NO: 405 | TCGGCCTGCCGAGCCTAGACAATmA |
| SEQ ID NO: 406 | ATTGTCTAGGCTCGGCAGGCCGAmC |
| SEQ ID NO: 407 | TCTCCTCTCGATGGGTCTCTCCmC |
| SEQ ID NO: 408 | GGAGAGACCCCATCGAGAGGAGAmG |
| SEQ ID NO: 409 | ATCCAGGCGCCGCCGGTGACCTTmC |
| SEQ ID NO: 410 | AAGGTCACCGGCGGCGCCTGGATmC |
| SEQ ID NO: 411 | GCGCACGCGCGGATCATTCGTCCmC |
| SEQ ID NO: 412 | GGACGAATGATCCGCGCGTGCGCmA |
| SEQ ID NO: 413 | ACAGTCTGACACGTTAGATAGAGmA |
| SEQ ID NO: 414 | CTCTATCTAACGTGTCAGACTGTmC |
| SEQ ID NO: 415 | ATGCGCCAGGTCGTGGACCGTCCmC |
| SEQ ID NO: 416 | GGACGGTCCACGACCTGGCGCATmG |
| SEQ ID NO: 417 | AGAGAACACTGCCGTCGGTTTTmA |
| SEQ ID NO: 418 | AAAAACCGACGGCAGTGTTCTCTmG |
| SEQ ID NO: 419 | TTGACGTTCGAAAAGATGTCAACmA |
| SEQ ID NO: 420 | GTTGACATCTTTTCGAACGTCAAmU |
| SEQ ID NO: 421 | AGTTTTTTTATACAACTGAGAGAmG |
| SEQ ID NO: 422 | TCTCTCAGTTGTATAAAAAAACTmC |
| SEQ ID NO: 423 | GAGTGAGTTAAATGGCAACAAACmA |
| SEQ ID NO: 424 | GTTTGTTGCCATTTAACTCACTCmG |
| SEQ ID NO: 425 | GGAAAAAAACTATGAGATGTCATmC |
| SEQ ID NO: 426 | ATGACATCTCTAGTTTTTTTCCmU |
| SEQ ID NO: 427 | ATGACGGTAAATAAATATGGATGmG |
| SEQ ID NO: 428 | CATCCATATTTATTTACCGTCATmA |
| SEQ ID NO: 429 | CTAAAACGAAAGTGGCAAAACCmU |
| SEQ ID NO: 430 | GGTTTTGCCACTTTTCGTTTTAGmU |
| SEQ ID NO: 431 | GACGGGTGTCGCCGAGTGCAGCCmG |
| SEQ ID NO: 432 | GGCTGCACTCGGCGACACCCGTCmC |
| SEQ ID NO: 433 | ACCCCCACCGATGTCCTGAGATTmG |
| SEQ ID NO: 434 | AATCTCAGGACATCGGTGGGGGTmU |
| SEQ ID NO: 435 | AAGCCGCAGGCAGCATCTGCATCmU |
| SEQ ID NO: 436 | GATGCAGATGCTGCCTGCGGCTTmC |
| SEQ ID NO: 437 | CTCCGCTCCGCCTACTGCTGCTGmG |

| | |
|---|---|
| SEQ ID NO: 438 | CAGCAGCAGTAGGCGGAGCGGAGmG |
| SEQ ID NO: 439 | GGCGGAGAAGGAGGCCCTTGCGCmC |
| SEQ ID NO: 440 | GCGCAAGGGCCTCCTTCTCCGCCmU |
| SEQ ID NO: 441 | GCCGGATCAGAGCCGGTAAGACCmA |
| SEQ ID NO: 442 | GGTCTTACCGGCTCTGATCCGGCmC |
| SEQ ID NO: 443 | CGCTCCTCCTCGCTGGTTGCTTTmC |
| SEQ ID NO: 444 | AAAGCAACCAGCGAGGAGGAGCGmU |
| SEQ ID NO: 445 | CGCCGGTATTCCCAGTCCGTGTGmC |
| SEQ ID NO: 446 | CACACGGACTGGGAATACCGGCGmG |
| SEQ ID NO: 447 | GTCTGCTCCCGTCGCTGCCTAGAmU |
| SEQ ID NO: 448 | TCTAGGCAGCGACGGGAGCAGACmA |
| SEQ ID NO: 449 | GGATCTTTCGTGCATGGCGGCAGmA |
| SEQ ID NO: 450 | CTGCCGCCATGCACGAAAGATCCmU |
| SEQ ID NO: 451 | CCCCCCCCCCCCCCCCCCCCCCCmC |
| SEQ ID NO: 452 | GGGGGGGGGGGGGGGGGGGGGGGmG |
| SEQ ID NO: 453 | CGTGTATACGAGTTTTCTCTAGGmC |
| SEQ ID NO: 454 | CCTAGAGAAAACTCGTATACACGmG |
| SEQ ID NO: 455 | CATGTTGGATTGGATTGCGCTAGmU |
| SEQ ID NO: 456 | CTAGCGCAATCCAATCCAACATGmC |
| SEQ ID NO: 457 | GAGGTGCCGGCCGTACCCATCCTmC |
| SEQ ID NO: 458 | AGGATGGGTACGGCCGGCACCTCmU |
| SEQ ID NO: 459 | AGAAAAAAGGCCCAGTCATTTTTmG |
| SEQ ID NO: 460 | AAAAATGACTGGGCCTTTTTTCTmG |
| SEQ ID NO: 461 | ATTTATTTTTACAGCTGCCACATmG |
| SEQ ID NO: 462 | ATGTGGCAGCTGTAAAAATAAATmA |
| SEQ ID NO: 463 | TTTTTGTTGGGGTTTTACTACTAmC |
| SEQ ID NO: 464 | TAGTAGTAAAACCCCAACAAAAAmC |
| SEQ ID NO: 465 | AACTGTTTTGTCAAATACTGTAAmC |
| SEQ ID NO: 466 | TTACAGTATTTGACAAAACAGTTmC |
| SEQ ID NO: 467 | AAAGCTGTTTGTAGGAGTGAAGCmU |
| SEQ ID NO: 468 | GCTTCACTCCTACAAACAGCTTTmA |
| SEQ ID NO: 469 | AAACAGAACTTCATATTGTTCCAmG |
| SEQ ID NO: 470 | TGGAACAATATGAAGTTCTGTTTmA |
| SEQ ID NO: 471 | TTCCAACAAAAAAATTGCAATTCmG |
| SEQ ID NO: 472 | GAATTGCAATTTTTTTGTTGGAAmC |
| SEQ ID NO: 473 | GCTACCAGTACAGCGCTAGATGGmA |
| SEQ ID NO: 474 | CCATCTAGCGCTGTACTGGTAGCmC |
| SEQ ID NO: 475 | CGAACATGAAACGTTTACTTTTmC |
| SEQ ID NO: 476 | AAAAAGTAAACGTTTCATGTTCGmC |
| SEQ ID NO: 477 | TGTTTGATGGATCACATTTATCTmC |
| SEQ ID NO: 478 | AGATAAATGTGATCCATCAAACAmU |
| SEQ ID NO: 479 | TGTTGGATACCGGTACTTTTTACmG |
| SEQ ID NO: 480 | GTAAAAGTACCGGTATCCAACAmC |
| SEQ ID NO: 481 | GTACAGGGGCCACTGGCTATATAmU |
| SEQ ID NO: 482 | TATATAGCCAGTGGCCCCTGTACmA |
| SEQ ID NO: 483 | CACTCCATTAATTTCCAGGGATGmC |
| SEQ ID NO: 484 | CATCCCTGGAAATTAATGGAGTmA |
| SEQ ID NO: 485 | CTCTCTCTGCTACATACATCCATmU |
| SEQ ID NO: 486 | ATGGATGTATGTAGCAGAGAGAGmA |
| SEQ ID NO: 487 | TTTTTTGTGGAATTTTGCACTTGmG |
| SEQ ID NO: 488 | CAAGTGCAAAATTCCACAAAAAAmA |
| SEQ ID NO: 489 | TCTCAGTTTAATTTGGAGGATCAmA |
| SEQ ID NO: 490 | TGATCCTCCAAATTAAACTGAGAmA |
| SEQ ID NO: 491 | AGACATACATGGCGGATCCTCTGmG |
| SEQ ID NO: 492 | CAGAGGATCCGCCATGTATGTCTmC |
| SEQ ID NO: 493 | AAGGTCTTAGCGGACTACTTGGTmG |
| SEQ ID NO: 494 | ACCAAGTAGTCCGCTAAGACCTTmC |
| SEQ ID NO: 495 | CTTCGTGGCCCTTCCAATATCTGmC |
| SEQ ID NO: 496 | CAGATATTGGAAGGGCCACGAAGmA |
| SEQ ID NO: 497 | TGGTGAACACGTGGTCCGCCATGmA |
| SEQ ID NO: 498 | CATGGCGGACCACGTGTTCACCAmG |
| SEQ ID NO: 499 | GAACACCAGGAGAACGTAGAGGGmU |
| SEQ ID NO: 500 | CCCTCTACGTTCTCCTGGTGTTCmC |
| SEQ ID NO: 501 | ATCCGAAGAGGGACGGCCTCGTCmU |
| SEQ ID NO: 502 | GACGAGGCCGTCCCTCTTCGGATmC |
| SEQ ID NO: 503 | GTCGTGGGCATGCGCAACGTGGAmC |
| SEQ ID NO: 504 | TCCACGTTGCGCATGCCCACGACmC |
| SEQ ID NO: 505 | GGTCGACCTCTCCGCGTTGAGGAmA |
| SEQ ID NO: 506 | TCCTCAACGCGGAGAGGTCGACCmU |
| SEQ ID NO: 507 | GGATGGTCGCCAGGGTGGAGCCTmC |
| SEQ ID NO: 508 | AGGCTCCACCCTGGCGACCATCCmU |
| SEQ ID NO: 509 | AAGGCTACCTGCCCCATGAACCTmC |
| SEQ ID NO: 510 | AGGTTCATGGGCAGGTAGCCTTmG |
| SEQ ID NO: 511 | GGACGACCTTACCGTCGGTGGTCmU |
| SEQ ID NO: 512 | GACCACCGACGGTAAGGTCGTCCmA |
| SEQ ID NO: 513 | GGAGCTCTCACGTCTACGGCCTCmU |
| SEQ ID NO: 514 | GAGGCCGTAGACGTGAGAGCTCCmC |

| | |
|---|---|
| SEQ ID NO: 515 | GAGGTCGTTCTTGCGGATGGGCAmG |
| SEQ ID NO: 516 | TGCCCATCCGCAAGAACGACCTCmC |
| SEQ ID NO: 517 | CGAGCACTCCGACCTCTTCTATGmG |
| SEQ ID NO: 518 | CATAGAAGAGGTCGGAGTGCTCGmU |
| SEQ ID NO: 519 | TCGGGCTCCTGGTTTCGGCTGAGmA |
| SEQ ID NO: 520 | CTCAGCCGAAACCAGGAGCCCGAmU |
| SEQ ID NO: 521 | TACATGAGGCTCACGTACACTCCmU |
| SEQ ID NO: 522 | GGAGTGTACGTGAGCCTCATGTAmC |
| SEQ ID NO: 523 | CGCGGAGGCTTATGCTGATTCGmU |
| SEQ ID NO: 524 | ACGAATCAGCATAAGCCTCCGCGmA |
| SEQ ID NO: 525 | CACATGAACCCGTATCGCGAGATmG |
| SEQ ID NO: 526 | ATCTCGCGATACGGGTTCATGTGmU |
| SEQ ID NO: 527 | TCTTTATCACAGTGGATGCATATmG |
| SEQ ID NO: 528 | ATATGCATCCACTGTGATAAAGAmA |
| SEQ ID NO: 529 | ACAGATGGTTAGCGAGTGACAGTmA |
| SEQ ID NO: 530 | ACTGTCACTCGCTAACCATCTGTmU |
| SEQ ID NO: 531 | AGTTGTCCGACACTTCATCGGTAmA |
| SEQ ID NO: 532 | TACCGATGAAGTGTCGGACAACTmU |
| SEQ ID NO: 533 | ACCGAGTGAATGGAAGAAAAACGmA |
| SEQ ID NO: 534 | CGTTTTTCTTCCATTCACTCGGTmU |
| SEQ ID NO: 535 | ACAGCAGGTTTTCTTAAAAAACGmU |
| SEQ ID NO: 536 | CGTTTTTTAAGAAAACCTGCTGTmG |
| SEQ ID NO: 537 | TTAAGAAGAGACCAAAATATGGTmC |
| SEQ ID NO: 538 | ACCATATTTTGGTCTCTTCTTAAmU |
| SEQ ID NO: 539 | TTCTAAACATTAGTTCTCATCACmC |
| SEQ ID NO: 540 | GTGATGAGAACTAATGTTTAGAAmA |
| SEQ ID NO: 541 | CATCTAGTTTGCAACGGTCCAGTmU |
| SEQ ID NO: 542 | ACTGGACCGTTGCAAACTAGATmG |
| SEQ ID NO: 543 | GACTCGCAGCGAGAGAATTTTTmU |
| SEQ ID NO: 544 | AAAAAATTCTCTCGCTGCGAGTCmC |
| SEQ ID NO: 545 | ATTCACTTTCGGACAAATCGAACmU |
| SEQ ID NO: 546 | GTTCGATTTGTCCGAAAGTGAATmU |
| SEQ ID NO: 547 | AACCATGAGACCTTTTCGCCGCAmG |
| SEQ ID NO: 548 | TGCGGCGAAAAGGTCTCATGGTTmA |
| SEQ ID NO: 549 | GGCCGTTAGATTTTAGTGACGATmG |
| SEQ ID NO: 550 | ATCGTCACTAAAATCTAACGGCCmG |
| SEQ ID NO: 551 | GCAACGTGCCGCATGCATCCATTmC |
| SEQ ID NO: 552 | AATGGATGCATGCGGCACGTTGCmG |
| SEQ ID NO: 553 | ACAGTACATGTAGGAGTACTGTGmC |
| SEQ ID NO: 554 | CACAGTACTCCTACATGTACTGTmG |
| SEQ ID NO: 555 | ACATTCAGTCTCTCTCACTAGTTmG |
| SEQ ID NO: 556 | AACTAGTGAGAGAGACTGAATGTmA |
| SEQ ID NO: 557 | CTACAAAGACATGAGCTGCCGGGmA |
| SEQ ID NO: 558 | CCCGGCAGCTCATGTCTTTGTAGmC |
| SEQ ID NO: 559 | GAGCGAGCGAGCCTGACGGTCTCmA |
| SEQ ID NO: 560 | GAGACCGTCAGGCTCGCTCGCTCmC |
| SEQ ID NO: 561 | ACTCCCAAGCCAATTATTATAAGmA |
| SEQ ID NO: 562 | CTTATAATAATTGGCTTGGGAGTmG |
| SEQ ID NO: 563 | ACTCCAGCTCTTAACCAATCCACmU |
| SEQ ID NO: 564 | GTGGATTGGTTAAGAGCTGGAGTmU |
| SEQ ID NO: 565 | CACCTCCTCTGCTTTGCTCTGCCmA |
| SEQ ID NO: 566 | GGCAGAGCAAAGCAGAGGAGGTGmG |
| SEQ ID NO: 567 | GGGGGCAGAGGAGCTCCCCCTCCmC |
| SEQ ID NO: 568 | GGAGGGGGAGCTCCTCTGCCCCCmC |
| SEQ ID NO: 569 | TCGCCATGTCTAGCAGCGACCCGmG |
| SEQ ID NO: 570 | CGGGTCGCTGCTAGACATGGCGAmG |
| SEQ ID NO: 571 | GCGCGTCGTCGTTCTCGGTTCGCmC |
| SEQ ID NO: 572 | GCGAACCGAGAACGACGACGCGCmG |
| SEQ ID NO: 573 | GGCGACGAGTGGGCCCGGCCCGAmG |
| SEQ ID NO: 574 | TCGGGCCGGGCCCACTCGTCGCCmG |
| SEQ ID NO: 575 | ATCTGCCGTCTCCCGCCCACCAGmC |
| SEQ ID NO: 576 | CTGGTGGGCGGGAGACGGCAGATmG |
| SEQ ID NO: 577 | AGCCGGGCAACCGGAAGCAGCAGmA |
| SEQ ID NO: 578 | CTGCTGCTTCCGGTTGCCCGGCTmA |
| SEQ ID NO: 579 | CCTGCTCCTGCTGGCCGCAGCAGmC |
| SEQ ID NO: 580 | CTGCTGCGGCCAGCAGGAGCAGGmG |
| SEQ ID NO: 581 | CGCCTACTACATCTGCCGGTGGCmG |
| SEQ ID NO: 582 | GCCACCGGCAGATGTAGTAGGCGmU |
| SEQ ID NO: 583 | TCCTCCTTCTTCGCCTCCCCCTCmC |
| SEQ ID NO: 584 | GAGGGGGAGGCGAAGAAGGAGGAmG |

CATS oligonucleotide sequences for silencing Old Gold gene (mC = 2'-O-methyl cytosine, mG = 2'-O-methyl guanine, mA = 2'-O-methyl adenine, mT = 2'-O-methyl thymine, mU = 2'-O-methyl uracil)

| | |
|---|---|
| SEQ ID NO: 585 | GGTTTAAAAAAGATTTCTTTTTTmU |
| SEQ ID NO: 586 | AAAAAAGAAATCTTTTTTAAACCmU |
| SEQ ID NO: 587 | GTAATCGACACACTAATGCAAAGmA |
| SEQ ID NO: 588 | CTTTGCATTAGTGTGTCGATTACmU |

| | |
|---|---|
| SEQ ID NO: 589 | AACATCTTGGACCTAAATAATTGmU |
| SEQ ID NO: 590 | CAATTATTTAGGTCCAAGATGTTmU |
| SEQ ID NO: 591 | CTTTCCATTTTCATCTTTAAATAmU |
| SEQ ID NO: 592 | TATTTAAAGATGAAAATGGAAAGmG |
| SEQ ID NO: 593 | ACAATTTTTTTTGGGCTAAAATmG |
| SEQ ID NO: 594 | ATTTTAGCCCAAAAAAAAATTGTmG |
| SEQ ID NO: 595 | TGGTGGAGTTATGACCACATATTmG |
| SEQ ID NO: 596 | AATATGTGGTCATAACTCCACCAmU |
| SEQ ID NO: 597 | AGTGCTCAAAAGGAGAGTCTACTmG |
| SEQ ID NO: 598 | AGTAGACTCTCCTTTTGAGCACTmU |
| SEQ ID NO: 599 | CCACCACAAGTACTATGCAACAmA |
| SEQ ID NO: 600 | TTGTTGCATAGTACTTGTGGTGGmA |
| SEQ ID NO: 601 | AAGAAAATGGAAACTTTTCTCTCmU |
| SEQ ID NO: 602 | GAGAGAAAAGTTTCCATTTTCTTmG |
| SEQ ID NO: 603 | CACTAGCTGTTTACATGGTGAGCmA |
| SEQ ID NO: 604 | GCTCACCATGTAAACAGCTAGTGmA |
| SEQ ID NO: 605 | AGAAATACTTAGTATATATCTATmA |
| SEQ ID NO: 606 | ATAGATATATACTAAGTATTTCTmA |
| SEQ ID NO: 607 | ACTTTTCATTCTGTAATTCTTTAmA |
| SEQ ID NO: 608 | TAAAGAATTACAGAATGAAAAGTmG |
| SEQ ID NO: 609 | CTGTTTAAAGCTTGATTTTTTTmA |
| SEQ ID NO: 610 | AAAAAAAATCAAGCTTTAAACAGmU |
| SEQ ID NO: 611 | ATGTTCTGCTTCATTTGTGTTGAmA |
| SEQ ID NO: 612 | TCAACACAAATGAAGCAGAACATmG |
| SEQ ID NO: 613 | ATTGGGAACTTTCTTGAATCCAmG |
| SEQ ID NO: 614 | TGGATTCAAGAAAGTTCCCCAATmU |
| SEQ ID NO: 615 | CATTTGAAGTTTTCTTGAAACAmA |
| SEQ ID NO: 616 | TTGTTTCAAGAAAACTTCAAATGmG |
| SEQ ID NO: 617 | CATTACCCTGTTGGAAAAGATGmG |
| SEQ ID NO: 618 | CATCTTTTCCAACAGGGTAATGmA |
| SEQ ID NO: 619 | TACTTTGTTGAAAACCCCAAATAmA |
| SEQ ID NO: 620 | TATTTGGGGTTTTCAACAAAGTAmU |
| SEQ ID NO: 621 | CTTGAATTTCTGAACCCACATCmU |
| SEQ ID NO: 622 | TGATGTGGGTTCAGAAATTCAAGmG |
| SEQ ID NO: 623 | GTTTTGCTGTTAAAGCTAGTACCmU |
| SEQ ID NO: 624 | GGTACTAGCTTTAACAGCAAAACmC |
| SEQ ID NO: 625 | GGTTCTAGGAAGTTTTGTGAAACmU |
| SEQ ID NO: 626 | GTTTCACAAAACTTCCTAGAACCmA |
| SEQ ID NO: 627 | TGGGTAGAAGTGTTTGTGTTAAGmG |
| SEQ ID NO: 628 | CTTAACACAAACACTTCTACCCAmA |
| SEQ ID NO: 629 | TAGTAGTAGTGCTCTTTTAGAGCmU |
| SEQ ID NO: 630 | GCTCTAAAAGAGCACTACTACTAmC |
| SEQ ID NO: 631 | GTACCTGAGACCAAAAAGGAGAAmU |
| SEQ ID NO: 632 | TTCTCCTTTTTGGTCTCAGGTACmA |
| SEQ ID NO: 633 | TTGATTTTGAGCTTCCTATGTATmG |
| SEQ ID NO: 634 | ATACATAGGAAGCTCAAAATCAAmG |
| SEQ ID NO: 635 | CTTGCTGTGGTTGGTGGTGGCCCmU |
| SEQ ID NO: 636 | GGGCCACCACCAACCACAGCAAGmA |
| SEQ ID NO: 637 | CAGGACTTGCTGTTGCACAGCAAmG |
| SEQ ID NO: 638 | TTGCTGTGCAACAGCAAGTCCTGmC |
| SEQ ID NO: 639 | TTCTGAAGCAGGACTCTCTGTTTmG |
| SEQ ID NO: 640 | AAACAGAGAGTCCTGCTTCAGAAmA |
| SEQ ID NO: 641 | TCAATTGATCCGAATCCTAAATTmG |
| SEQ ID NO: 642 | AATTTAGGATTCGGATCAATTGAmA |
| SEQ ID NO: 643 | TATGGCCTAATAACTATGGTGTTmU |
| SEQ ID NO: 644 | AACACCATAGTTATTAGGCCATAmU |
| SEQ ID NO: 645 | TTGTTAGATTGTCTAGATGCTACmC |
| SEQ ID NO: 646 | GTAGCATCTAGACAATCTAACAAmG |
| SEQ ID NO: 647 | GGTCTGGTGCAGCAGTGTACATTmG |
| SEQ ID NO: 648 | AATGTACACTGCTGCACCAGACCmA |
| SEQ ID NO: 649 | TGATAATACGGCTAAAGATCTTCmA |
| SEQ ID NO: 650 | GAAGATCTTTAGCCGTATTATCAmU |
| SEQ ID NO: 651 | AGACCTTATGGAAGGGTTAACCGmG |
| SEQ ID NO: 652 | CGGTTAACCCTTCCATAAGGTCTmA |
| SEQ ID NO: 653 | AACAGCTGAAATCGAAATGATGmC |
| SEQ ID NO: 654 | CATCATTTCGATTTCAGCTGTTmU |
| SEQ ID NO: 655 | TTCCACCAAGCCAAAGTTATAAAmG |
| SEQ ID NO: 656 | TTTATAACTTTGGCTTGGTGGAAmU |
| SEQ ID NO: 657 | TGATTCATGAGGAATCGAAATCCmA |
| SEQ ID NO: 658 | GGATTTCGATTCCTCATGAATCAmC |
| SEQ ID NO: 659 | GTTGATATGCAATGATGGTATTAmC |
| SEQ ID NO: 660 | TAATACCATCATTGCATATCAACmA |
| SEQ ID NO: 661 | ATTCAGGCAACGGTGGTGCTCGAmU |
| SEQ ID NO: 662 | TCGAGCACCACCGTTGCCTGAATmA |
| SEQ ID NO: 663 | CAACTGGCTTCTCTAGATCTCTTmG |
| SEQ ID NO: 664 | AAGAGATCTAGAGAAGCCAGTTGmC |

What is claimed is:

1. A method of inducing an epigenetic modification in a plant organism, comprising applying a formulation to an agricultural object, the formulation comprising an excipient and a double stranded artificial nucleic acid construct consisting of (a) a first strand and a second strand each having a length of 20 to 30 nucleotides or nucleosides or a combination thereof; and (b) a terminal overhang at each of the 3' end of the first strand and second strand; wherein: both of the 3' terminal end overhangs comprise a ribose unit having a methoxy group (—O-Me) at a 2' position;
wherein every sugar in the double stranded artificial nucleic acid construct is a deoxyribose except for the terminal 3' sugar of the first strand and the second strand,
wherein the agricultural object is a seed, a plant, a constituent of a plant, or any combination thereof,
wherein the applying causes methylation of at least one base of a nucleotide or nucleoside in a nucleic acid sequence of a gene of the agricultural object, and
wherein the applying causes methylation via an interaction between the double stranded artificial nucleic acid construct and an endogenous DNA methyltransferase.

2. The method of claim 1, wherein one strand of the double stranded nucleic acid construct comprises at least 80% sequence identity to a portion of a transcription regulatory region of the gene.

3. The method of claim 2, wherein the transcription regulatory region is a transcription start site, a TATA box, or an upstream activating sequence.

4. The method of claim 2, wherein the portion of the transcription regulatory region comprises at least 30% guanine cytosine (GC) content.

5. The method of claim 1, wherein the formulation comprises an excipient and a plurality of double stranded artificial nucleic acid constructs.

6. The method of claim 1, wherein the at least one base is a cytosine.

7. The method of claim 1, wherein the system comprises at least a portion of at least one component of an RNA directed DNA methylation pathway.

8. The method of claim 1, wherein each terminal end overhang is one nucleotide long.

9. The method of claim 1, wherein the agricultural object comprises a plant, a seed, a fruit, a leaf, a stalk, a root, a flower, a plant embryo, or any combination thereof.

10. The method of claim 1, wherein the method results in at least partial silencing of the gene in the agricultural object for at least one reproduction cycle of the agricultural object.

11. The method of claim 1, wherein the applying results in one or more of: (a) preventing or reducing or delaying an enzymatic browning of the agricultural object; (b) increasing a growth rate, a yield, or a lifespan of the agricultural object; (c) decreasing a growth rate, a yield, or a lifespan of the agricultural object; (d) increasing a pest resistance, a salt tolerance, a heat tolerance, a heavy metal tolerance, a disease tolerance, or a drought resistance of the agricultural object; (e) increasing or at least partially decreasing an amount or a production of a molecule made by the agricultural object; (f) altering a color of at least a portion of the agricultural object; (g) increasing or at least partially decreasing a flowering rate of the agricultural object; (h) increasing a volume or a weight of the agricultural object; (i) improving a flavor or a texture of an edible product of the agricultural object; (j) increasing a shelf life of the agriculture object; (k) decreasing the number and size of seeds of the agriculture object; and (l) increasing a nutritional content of the agricultural object; when the agricultural object is compared to a comparable agricultural object without application of the formulation comprising the double stranded artificial nucleic acid construct.

12. The method of claim 1, wherein the plant organism is soybean, corn, rice, tomato, alfalfa, wheat, potato, or pea.

13. The method of claim 12, wherein the plant organism is soybean or corn.

14. The method of claim 1, wherein the formulation is a powder, granule, pellet, bead, or liquid.

15. The method of claim 1, wherein the excipient is water.

\* \* \* \* \*

SEQUENCE LISTING

<160> NUMBER OF SEQ ID NOS: 674

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tggctactat gtattgatgt taac                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttaacatcaa tacatagtag ccag                                              24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccattaagat gtactcgctc tgta                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acagagcgag tacatcttaa tgga                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
taatcatttt tgtctgttat tttu                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaataacag acaaaaatga ttac                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
gtctatattc agacagatga taau                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttatcatctg tctgaatata gaca                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctagacacat ataccaagta atga                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cattacttgg tatatgtgtc taga                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggatataggg agtatgaaca actg                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic

```
    oligonucleotide
<220> FEATURE:
<223> OTHER INFORMATION: Description of Combined DNA/RNA Molecule:
      Synthetic oligonucleotide

<400> SEQUENCE: 12
agttgttcat actccctata tccu                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
caattagttc cgtattgata atau                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
tattatcaat acggaactaa ttgu                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggatcgacgt atttataata atac                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tattattata aatacgtcga tcca                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 17
tgttctatat ctatatttaa ttau                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taattaaata tagatataga acag                                          24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
gcggaggtct ccactcttct ctcu                                          24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagagaagag tggagacctc cgca                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccatcttatc atcgcccacg taca                                          24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtacgtgggc gatgataaga tgga                                          24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 23
cccaattcct cgcaactggg ctcc                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
gagcccagtt gcgaggaatt gggu                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgcctccacg acactgcccc ccgc                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 cgggggcag tgtcgtggag gcgg                                               24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caagtccgcc gcctccattc ttca                                              24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gaagaatgga ggcggcggac ttga                                              24

<210> SEQ ID NO 29
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 29
gtgcgttggt gggtctgaaa caata                                               25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
attgtttcag acccaccaac gcaca                                               25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtctcaaaag gaggtgagct ggga                                                24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cccagctcac ctcctttga gacg                                                 24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tttagccgac taattttaga tgag                                                24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
tcatctaaaa ttagtcggct aaau                                                24

<210> SEQ ID NO 35
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
taatctttag ttccgtgccc ccgc                                              24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
cgggggcacg gaactaaaga ttau                                              24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgcaggctca ccccgacgtg cccc                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gggcacgtcg gggtgagcct gcac                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
gccctccgcg cgcgatgccc ccau                                              24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
```

```
tgggggcatc gcgcgcggag ggca                                          24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
caccgacgca gagctcgccc atgc                                          24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
catgggcgag ctctgcgtcg gtgu                                          24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
cacgtgcccc ggcggcgtcg cgau                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcgcgacgcc gccggggcac gtgc                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tatccccgcc gtcgcgcgcc tacg                                          24

<210> SEQ ID NO 46
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 46
gtaggcgcgc gacggcgggg atac                                              24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtacctggag cagaagcgat ttcg                                              24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gaaatcgctt ctgctccagg taca                                              24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tgccgaggag ctcaccgctg tgaa                                              24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcacagcggt gagctcctcg gcaa                                              24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tagtcccgtc ccctccaggt cctg                                              24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 52
aggacctgga ggggacggga ctaa                                              24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aattcacttg tgtattcccc cgaa                                              24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcgggggaat acacaagtga attg                                              24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gagacagtct gcacggctcc tatc                                              24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ataggagccg tgcagactgt ctcg                                              24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gcatgtaccc aatacctgt tttg                                               24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 58
aaaacagggt attgggtaca tgcu                                              24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgaccttggg tactattata gcac                                              24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgctataata gtacccaagg tcaa                                              24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tttcagttcg agtgttagac cctg                                              24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agggtctaac actcgaactg aaac                                              24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63 cttttggaa ttcttctgac cagg                                               24

<210> SEQ ID NO 64
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 64
ctggtcagaa gaattccaaa aaga                                           24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
caagaaaatt aaggatatat agcg                                           24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gctatatatc cttaattttc ttgg                                           24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
taaggcatgt cgataataaa gacu                                           24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gtctttatta tcgacatgcc ttag                                           24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ataggaccga gcaactcgga ttcg                                           24

<210> SEQ ID NO 70
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
gaatccgagt tgctcggtcc tatu                                            24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
gactcggact tggactgtgc aacu                                            24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gttgcacagt ccaagtccga gtca                                            24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
agccgggata ctcaaaatcg aaau                                            24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tttcgatttt gagtatcccg gctg                                            24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 75
actcggtcca taggttaata ctca                                           24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gagtattaac ctatggaccg agtc                                           24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcatatttta catctaaacg ttcg                                           24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gaacgtttag atgtaaaata tgag                                           24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tggaagcaaa caccccctta gacg                                           24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtctaagggg gtgtttgctt ccac                                           24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81

```
<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
tacaaatggt cgacaagagg tggu                                           24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
catgttccgt tctgccgact gatg                                           24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
atcagtcggc agaacggaac atga                                           24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
cctgcagctg cagctgcagt gcgu                                           24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cgcactgcag ctgcagctgc agga                                           24

<210> SEQ ID NO 87
<211> LENGTH: 24
<212> TYPE: DNA
<213> ORGANISM: Artificial Sequence
```
ccacctcttg tcgaccattt gtag                                           24

```
<220> FEATURE:
<223> OTHER INFORMATION: Description of Artificial Sequence: Synthetic
      oligonucleotide

<400> SEQUENCE: 87
actccatcgt ctattaatgg ctcg                                              24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gagccattaa tagacgatgg agta                                              24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
ccagcgctcg gcttagacaa gccu                                              24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggcttgtcta agccgagcgc tgga                                              24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
atgaaggtca gtcagtagtc ccac                                              24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tgggactact gactgacctt catg                                              24

<210> SEQ ID NO 93
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agcttttagt ctagctcgac agtc                                          24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
actgtcgagc tagactaaaa gctg                                          24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
ttctttctaa tccacctatt ttcu                                          24

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gaaaataggt ggattagaaa gaac                                          24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
gcgactcact ctcgtagttg gtgu                                          24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
```
caccaactac gagagtgagt cgcc                                              24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tcatgacctc ctcctcaagc tcgg                                              24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cgagcttgag gaggaggtca tgaa                                              24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ctcatatttg aagcctcctt gttc                                              24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aacaaggagg cttcaaatat gaga                                              24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
agaaagcatc gaccttagca aggu                                              24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 104
ccttgctaag gtcgatgctt tctu                                              24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ttgtccatgc gcttggtgag gtcg                                              24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gacctcacca agcgcatgga caag                                              24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aatctaacct ttgagtacca aatg                                              24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atttggtact caaaggttag attg                                              24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tggagacaca tacacagaga agaa                                              24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 110
tcttctctgt gtatgtgtct ccau                                            24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cttgtttgga ttgaaaccat taca                                            24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtaatggttt caatccaaac aaga                                            24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
atatattgga cttgtattcc aagc                                            24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cttggaatac aagtccaata tata                                            24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gtccttatag atttggacac ttau                                            24

<210> SEQ ID NO 116
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
taagtgtcca aatctataag gacu                                         24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
caaatcttct tgcctaagca aatu                                         24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
atttgcttag gcaagaagat ttgu                                         24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctaaactcta ttttatactc cctc                                         24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
agggagtata aaatagagtt tagu                                         24

<210> SEQ ID NO 121
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
agtgttcatt ttggctcctc attu                                         24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
aatgaggagc caaaatgaac acta                                         24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tcagatggat gaaatgaat ctag                                          24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tagattcatt ttcatccatc tgaa                                         24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgaatccact gatatgttaa aacg                                         24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
gttttaacat atcagtggat tcau                                         24
```

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gggacggaga gagtatattc caag                                            24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ttggaatata ctctctccgt ccca                                            24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ctatctttgg gttttcatct tttu                                            24

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
aaaagatgaa aacccaaaga tagc                                            24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gaccaggagg gactctattt atau                                            24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 132
tataaataga gtccctcctg gtca                                          24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gataataaag actctgacta atag                                          24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tattagtcag agtctttatt atcg                                          24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
agactctgac taataggacc gagc                                          24

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
ctcggtccta ttagtcagag tctu                                          24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
actaatagga ccgagcaact cgga                                          24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ccgagttgct cggtcctatt agtc                                          24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gaccgagcaa ctcggattcg gtgg                                          24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
caccgaatcc gagttgctcg gtcc                                          24

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
aactcggatt cggtggagtg actc                                          24

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
agtcactcca ccgaatccga gttg                                          24

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ttcggtggag tgactcggac ttgg                                          24

<210> SEQ ID NO 144
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
caagtccgag tcactccacc gaau                                          24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
agtgactcgg acttggactg tgca                                          24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gcacagtcca agtccgagtc actc                                          24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
ggacttggac tgtgcaactc ggau                                          24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tccgagttgc acagtccaag tccg                                          24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
actgtgcaac tcggattcag ccgg                                          24
```

```
<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cggctgaatc cgagttgcac agtc                                              24

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
actcggattc agccgggata ctca                                              24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
gagtatcccg gctgaatccg agtu                                              24

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tcagccggga tactcaaaat cgaa                                              24

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tcgattttga gtatcccggc tgaa                                              24

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gatactcaaa atcgaaatcc aagg                                              24
```

```
<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cttggatttc gattttgagt atcc                                          24

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
aaatcgaaat ccaagggact cggu                                          24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
ccgagtccct tggatttcga tttu                                          24

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
atccaaggga ctcggtccat aggu                                          24

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
cctatggacc gagtcccttg gatu                                          24
```

```
<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gactcggtcc ataggttaat actc                                              24

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
agtattaacc tatggaccga gtcc                                              24

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tcatatttta catctaaacg ttcg                                              24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gaacgtttag atgtaaaata tgag                                              24

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
tacatctaaa cgttcgatgt gcgu                                              24

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cgcacatcga acgtttagat gtaa                                              24
```

```
<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
aacgttcgat gtgcgtggaa gcaa                                              24

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
tgcttccacg cacatcgaac gttu                                              24

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
atgtgcgtgg aagcaaacac cccc                                              24

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggggtgtttg cttccacgca catc                                              24

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
ggaagcaaac accccttag acgu                                               24

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 172
cgtctaaggg ggtgtttgct tcca    24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 173
acaccccctt agacgtggga cacc    24

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 174
gtgtcccacg tctaaggggg tgtu    24

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 175
ttagacgtgg gacaccacct cttg    24

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 176
aagaggtggt gtcccacgtc taag    24

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 177
gggacaccac ctcttgtcga ccau    24

<210> SEQ ID NO 178

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tggtcgacaa gaggtggtgt ccca                                           24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
acctcttgtc gaccatttgt agcc                                           24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gctacaaatg gtcgacaaga ggtg                                           24

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
tcgaccattt gtagccttct tcau                                           24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgaagaaggc tacaaatggt cgac                                           24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
```
ttgtagcctt cttcatgttc cgtu                                              24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
acggaacatg aagaaggcta caaa                                              24

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttcttcatgt tccgttctgc cgac                                              24

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tcggcagaac ggaacatgaa gaag                                              24

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
gttccgttct gccgactgat ggau                                              24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tccatcagtc ggcagaacgg aaca                                              24

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ctgccgactg atggatcact cctg							24

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
aggagtgatc catcagtcgg caga							24

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgatggatca ctcctgcagc tgca							24

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gcagctgcag gagtgatcca tcag							24

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
cactcctgca gctgcagctg cagu							24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ctgcagctgc agctgcagga gtga							24

<210> SEQ ID NO 195
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 195
atgaagcaaa actctaaagt tgac                                               24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tcaactttag agttttgctt cata                                               24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aacccagttt ttcagctctc acta                                               24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
agtgagagct gaaaaactgg gttg                                               24

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
attaccaatt gatcatcatc ttgc                                               24

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
caagatgatg atcaattggt aatu                                               24

<210> SEQ ID NO 201
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 201
attacaactt tccagctatt ttgc                                            24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
caaaatagct ggaaagttgt aata                                            24

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cactttataa tcctaatcct acac                                            24

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
tgtaggatta ggattataaa gtgu                                            24

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
aagctcattc aacaacacaa ttag                                            24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
taattgtgtt gttgaatgag cttu                                            24
```

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tcaaacacaa aatagagtta tggc                                          24

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
ccataactct attttgtgtt tgau                                          24

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttaacttcat gtactaccat ttcc                                          24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gaaatggtag tacatgaagt taaa                                          24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
catccaaaat tttcgtccgt ccaa                                          24

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tggacggacg aaaatttttgg atgg                                24

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cgataacttt aaggtgaatt gtga                                 24

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cacaattcac cttaaagtta tcga                                 24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
taatgaagga aaatcttttc cagg                                 24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
ctggaaaaga ttttccttca ttau                                 24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
gatagacgaa atgtcctcct tggu                                 24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ccaaggagga catttcgtct atca                                            24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ggctctatgg agcatctaat ctta                                            24

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
aagattagat gctccataga gccc                                            24

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
aaccaacgag ccatttgccc tagg                                            24

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ctagggcaaa tggctcgttg gtta                                            24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gtaccacccc cagacttctc aaca                                            24

<210> SEQ ID NO 224
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 224
gttgagaagt ctgggggtgg tacc                                              24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tctgtcaacc gacccaaccg accc                                              24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ggtcggttgg gtcggttgac agaa                                              24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tccagactgt aagttatttt tctg                                              24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
agaaaaataa cttacagtct ggau                                              24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
cagagcttct aagaacaaaa actu                                              24
```

```
<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230 agttttttgtt cttagaagct ctgu                                         24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gtatggctgc tatacaaaat tccc                                          24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ggaattttgt atagcagcca taca                                          24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
cgcttcctgg aataattgat atgg                                          24

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
catatcaatt attccaggaa gcgg                                          24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tattatataa ggcaaggtat agcc                                          24
```

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gctatacctt gccttatata ataa                                          24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tcattcaaaa cctagcaata atgg                                          24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cattattgct aggttttgaa tgaa                                          24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gtagtaatac atctctcaaa actc                                          24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
agttttgaga gatgtattac tacu                                          24

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ttcttcctcc acttctttat cttc                                                24

<210> SEQ ID NO 242
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
aagataaaga agtggaggaa gaag                                                24

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
aagccctctt caacttttca tcca                                                24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggatgaaaag ttgaagaggg ctta                                                24

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
cgtaccaaat gttcaaagtt tcau                                                24

<210> SEQ ID NO 246
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
tgaaactttg aacatttggt acgu                                                24

<210> SEQ ID NO 247
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 247
taccaataat aacggtgacc aaaa                                              24

<210> SEQ ID NO 248
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tttggtcacc gttattattg gtaa                                              24

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gttgaaacga attctgttga tcga                                              24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cgatcaacag aattcgtttc aacg                                              24

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
ttcttcttgg cttaggtggt cttu                                              24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
aagaccacct aagccaagaa gaac                                              24

<210> SEQ ID NO 253
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tgctaatgct ataccattag ctgc                                           24

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
cagctaatgg tatagcatta gcaa                                           24

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
aattatcaat gcttgtgaat ctcg                                           24

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
gagattcaca agcattgata attu                                           24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tgttaaaaaa tttcctcacc tacc                                           24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gtaggtgagg aaattttta acaa                                            24
```

```
<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gaattgttcg atatgagatc gagc                                              24

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ctcgatctca tatcgaacaa ttcg                                              24

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tggagtaata ttttatttgg ctcc                                              24

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
gagccaaata aaatattact ccau                                              24

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tatataaggc aatgtatagc ccta                                              24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
agggctatac attgccttat ataa                                              24
```

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tcatccaaaa actagcaatg gcaa                                           24

<210> SEQ ID NO 266
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tgccattgct agtttttgga tgaa                                           24

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
taatagtagt agtaccactc tcaa                                           24

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
tgagagtggt actactacta ttac                                           24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tttacttctt cctccacttc ttta                                           24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
aaagaagtgg aggaagaagt aaaa                                           24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ctcctaagcc ctctcaactt ttcc                                            24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
gaaaagttga gagggcttag gagu                                            24

<210> SEQ ID NO 273
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
acgtaacaaa acgttcaaag tttc                                            24

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
aaactttgaa cgttttgtta cgtu                                            24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gttaccaata ataacggtga ccaa                                            24

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 276
tggtcaccgt tattattggt aacc                                              24

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
acgttgaaac gaattctgtt gatc                                              24

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
atcaacagaa ttcgtttcaa cgtu                                              24

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
tgttcttctt ggtttaggag gtcu                                              24

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
gacctcctaa accaagaaga acau                                              24

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
```
gttgctaatg ctataccatt agcu                                           24

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gctaatggta tagcattagc aaca                                           24

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
cttctccaac tccacctcct gatc                                           24

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
atcaggaggt ggagttggag aagc                                           24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccaaacaatc tgttcagcta ttca                                           24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
gaatagctga acagattgtt tggu                                           24

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
aaatgtgtaa aagatttccc acac                                          24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
tgtgggaaat cttttacaca tttu                                          24

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
tcaaaaacct cccacctacc gcgu                                          24

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
cgcggtaggt gggaggtttt tgaa                                          24

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
tgttggagtg gtaggtgagc ctcu                                          24

<210> SEQ ID NO 292
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292

```
gaggctcacc taccactcca acau                                           24
```

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293

```
agcaacatac tatataatgc aagg                                           24
```

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294

```
cttgcattat atagtatgtt gcta                                           24
```

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295

```
tatgaatctt catcaaccaa aagc                                           24
```

<210> SEQ ID NO 296
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296

```
cttttggttg atgaagattc atau                                           24
```

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297

```
aatggcaagt gtgtgcaata gtag                                           24
```

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide <210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
actacaactc tcaaaactcc tttc                                          24

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
aaaggagttt tgagagttgt agta                                          24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ccaatacttc tttatcttca actc                                          24

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
agttgaagat aaagaagtat tgga                                          24

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
ctctcaactt ttcctccatg gaaa                                          24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ttccatggag gaaaagttga gagg                                          24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
caaatgttca aagtttcatg caag                                          24

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
ttgcatgaaa ctttgaacat ttgg                                          24

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ataataacgg tgaccaaaac gttg                                          24

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
aacgttttgg tcaccgttat tatu                                          24

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
ttctgttgat cgaagaaatg ttcu                                          24

<210> SEQ ID NO 310
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
gaacatttct tcgatcaaca gaau                                           24

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
ttaggaggtc tatatggtgt tgcu                                           24

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gcaacaccat atagacctcc taaa                                           24

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
taccattagc tgcatccgct gctc                                           24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
agcagcggat gcagctaatg gtau                                           24

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 315
gatcaaagga tggctaaatt tttc                                         24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
aaaaatttag ccatcctttg atca                                         24

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ttgaacttga ggatcaatat ttcc                                         24

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gaaatattga tcctcaagtt caaa                                         24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
gagagtgagt aattactcca agau                                         24

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
tcttggagta attactcact ctcu                                         24

<210> SEQ ID NO 321
<211> LENGTH: 24
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 321
acaattatca ccaacgtgtt acac                                              24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tgtaacacgt tggtgataat tgta                                              24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gctacatata ccttcaccat tttg                                              24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
aaaatggtga aggtatatgt agca                                              24

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gcaactcttc taacaaaaaa tcac                                              24

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326 tgatttttg ttagaagagt tgca                                               24

<210> SEQ ID NO 327
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
aacacaatgt cttcttctag tacu                                          24

<210> SEQ ID NO 328
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gtactagaag aagacattgt gttg                                          24

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ttccattatg caccaacaaa tccc                                          24

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
ggatttgttg gtgcataatg gaag                                          24

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ttccttcacc accaacaact catc                                          24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
atgagttgtt ggtggtgaag gaag                                          24

<210> SEQ ID NO 333
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tcaaacccct ctcaactttt cctc                                              24

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
aggaaaagtt gagagggttt tgau                                              24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
gacgtaatca aagtttcaag gttu                                              24

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
aaccttgaaa ctttgattac gtcu                                              24

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
cgtcaacaat aatgttggcg agca                                              24

<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 338
gctcgccaac attattgttg acgu                                                24

<210> SEQ ID NO 339
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
aaccttgacg ctgttgatag gcga                                                24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
cgcctatcaa cagcgtcaag gttu                                                24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ttttagggtt aggaggtctt tatg                                                24

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
ataaagacct cctaacccta aaag                                                24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
taatcttgca ccattagcct ctgc                                                24

<210> SEQ ID NO 344
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
cagaggctaa tggtgcaaga ttag                                              24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
tgcaaaagaa aataggatct gcau                                              24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
tgcagatcct attttctttt gcau                                              24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
atacaaaacc atttcaaaac tgcg                                              24

<210> SEQ ID NO 348
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
gcagttttga aatggttttg tatu                                              24

<210> SEQ ID NO 349
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 349
cgtttgtact aggtacatga attu                                          24

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
aattcatgta cctagtacaa acgu                                          24

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
aaatactgat gaaacgctgc aaag                                          24

<210> SEQ ID NO 352
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
tttgcagcgt ttcatcagta ttta                                          24

<210> SEQ ID NO 353
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
actcatccca gcaatggctt cttc                                          24

<210> SEQ ID NO 354
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
aagaagccat tgctgggatg agtg                                          24

<210> SEQ ID NO 355
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cctttgtgca ctaccaatat tccc                                              24

<210> SEQ ID NO 356
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
ggaatattgg tagtgcacaa aggu                                              24

<210> SEQ ID NO 357
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
tctccaataa taccaactca tctu                                              24

<210> SEQ ID NO 358
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
agatgagttg gtattattgg agaa                                              24

<210> SEQ ID NO 359
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
aaaaccctct cagcttttcc tcca                                              24

<210> SEQ ID NO 360
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
```
ggaggaaaag ctgagagggt tttg                                              24

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
cgtagtcaaa gtttcaaggt ttca                                              24

<210> SEQ ID NO 362
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gaaaccttga aactttgact acgc                                              24

<210> SEQ ID NO 363
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
atagcgagca tgacaaaaat aacc                                              24

<210> SEQ ID NO 364
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gttatttttg tcatgctcgc tata                                              24

<210> SEQ ID NO 365
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
cgatgctgtt gataggagaa atgu                                              24

<210> SEQ ID NO 366
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 366
catttctcct atcaacagca tcgu                                          24

<210> SEQ ID NO 367
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 367
gggttaggag gtctttatgg tgcu                                          24

<210> SEQ ID NO 368
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
gcaccataaa gacctcctaa cccu                                          24

<210> SEQ ID NO 369
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
ttgcaccatt agccactgct gctc                                          24

<210> SEQ ID NO 370
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
agcagcagtg gctaatggtg caag                                          24

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
accacctgat ttgaaaactt gtag                                          24

```
<210> SEQ ID NO 372
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
tacaagtttt caaatcaggt ggtg                                            24

<210> SEQ ID NO 373
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
actgtaactc ctggtggtcc agca                                            24

<210> SEQ ID NO 374
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gctggaccac caggagttac agtg                                            24

<210> SEQ ID NO 375
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tatgtgctca cgtggacaca ttac                                            24

<210> SEQ ID NO 376
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
taatgtgtcc acgtgagcac atag                                            24

<210> SEQ ID NO 377
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gatgcaatat ttatgatgtt cacg                                            24

<210> SEQ ID NO 378
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gtgaacatca taaatattgc atca                                           24

<210> SEQ ID NO 379
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
attatattct cgacaagttg aacg                                           24

<210> SEQ ID NO 380
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
gttcaacttg tcgagaatat aatu                                           24

<210> SEQ ID NO 381
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 381
ggaaatgatg gagattatta tggu                                           24

<210> SEQ ID NO 382
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
ccataataat ctccatcatt tcca                                           24

<210> SEQ ID NO 383
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
```
tcttcctcac aaggtaatta caaa                                          24

<210> SEQ ID NO 384
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
ttgtaattac cttgtgagga agaa                                          24

<210> SEQ ID NO 385
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
ccttagcttg ctccatatta ttcu                                          24

<210> SEQ ID NO 386
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gaataatatg gagcaagcta agga                                          24

<210> SEQ ID NO 387
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
tgctagccct agatgttcat gaau                                          24

<210> SEQ ID NO 388
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 388
ttcatgaaca tctagggcta gcau                                          24

<210> SEQ ID NO 389

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
caagcaaaaa aatgtcttcc attc                                              24

<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 390
aatggaagac atttttttgc ttgu                                              24

<210> SEQ ID NO 391
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
cactaccaat actctctctt cttc                                              24

<210> SEQ ID NO 392
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
aagaagagag agtattggta gtgg                                              24

<210> SEQ ID NO 393
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 393
accacttttt ccaacttgca ttcu                                              24

<210> SEQ ID NO 394
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
```
gaatgcaagt tggaaaaagt ggtg                                          24

<210> SEQ ID NO 395
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gcaaaaacat caaaaatttc ctcc                                          24

<210> SEQ ID NO 396
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gaggaaattt ttgatgtttt tgca                                          24

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
agcataatgt ccatcgtaat ttcc                                          24

<210> SEQ ID NO 398
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
gaaattacga tggacattat gctu                                          24

<210> SEQ ID NO 399
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gcaaaaccat agatgataat agtc                                          24

<210> SEQ ID NO 400
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 400
actattatca tctatggttt tgca                                        24

<210> SEQ ID NO 401
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
caataactca cccatcgaca tttc                                        24

<210> SEQ ID NO 402
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 402
aaatgtcgat gggtgagtta ttgu                                        24

<210> SEQ ID NO 403
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
acaatatgat cgatagaaga aacg                                        24

<210> SEQ ID NO 404
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 404
gtttcttcta tcgatcatat tgtu                                        24

<210> SEQ ID NO 405
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
tcggcctgcc gagcctagac aata                                        24

<210> SEQ ID NO 406
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
attgtctagg ctcggcaggc cgac                                         24

<210> SEQ ID NO 407
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
tctcctctcg atgggtctc tccc                                          24

<210> SEQ ID NO 408
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ggagagaccc catcgagagg agag                                         24

<210> SEQ ID NO 409
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
atccaggcgc cgccggtgac cttc                                         24

<210> SEQ ID NO 410
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
aaggtcaccg gcggcgcctg gatc                                         24

<210> SEQ ID NO 411
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
gcgcacgcgc ggatcattcg tccc                                         24

<210> SEQ ID NO 412
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 412
ggacgaatga tccgcgcgtg cgca                                          24

<210> SEQ ID NO 413
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
acagtctgac acgttagata gaga                                          24

<210> SEQ ID NO 414
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ctctatctaa cgtgtcagac tgtc                                          24

<210> SEQ ID NO 415
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
atgcgccagg tcgtggaccg tccc                                          24

<210> SEQ ID NO 416
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
ggacggtcca cgacctggcg catg                                          24

<210> SEQ ID NO 417
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
agagaacact gccgtcggtt ttta                                          24

<210> SEQ ID NO 418
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 418
aaaaaccgac ggcagtgttc tctg                                          24

<210> SEQ ID NO 419
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ttgacgttcg aaaagatgtc aaca                                          24

<210> SEQ ID NO 420
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 420
gttgacatct tttcgaacgt caau                                          24

<210> SEQ ID NO 421
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
agttttttta tacaactgag agag                                          24

<210> SEQ ID NO 422
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
tctctcagtt gtataaaaaa actc                                          24

<210> SEQ ID NO 423
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
gagtgagtta aatggcaaca aaca                                          24

<210> SEQ ID NO 424
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gtttgttgcc atttaactca ctcg                                              24

<210> SEQ ID NO 425
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
ggaaaaaaac tatgagatgt catc                                              24

<210> SEQ ID NO 426
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
atgacatctc atagtttttt tccu                                              24

<210> SEQ ID NO 427
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
atgacggtaa ataaatatgg atgg                                              24

<210> SEQ ID NO 428
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
catccatatt tatttaccgt cata                                              24

<210> SEQ ID NO 429
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
```
ctaaaacgaa aagtggcaaa accu                                          24

<210> SEQ ID NO 430
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
ggttttgcca cttttcgttt tagu                                          24

<210> SEQ ID NO 431
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
gacgggtgtc gccgagtgca gccg                                          24

<210> SEQ ID NO 432
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ggctgcactc ggcgacaccc gtcc                                          24

<210> SEQ ID NO 433
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433 accccaccg atgtcctgag attg                                           24

<210> SEQ ID NO 434
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 434
aatctcagga catcggtggg ggtu                                          24

<210> SEQ ID NO 435
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 435
aagccgcagg cagcatctgc atcu                                           24

<210> SEQ ID NO 436
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
gatgcagatg ctgcctgcgg cttc                                           24

<210> SEQ ID NO 437
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ctccgctccg cctactgctg ctgg                                           24

<210> SEQ ID NO 438
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
cagcagcagt aggcggagcg gagg                                           24

<210> SEQ ID NO 439
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
ggcggagaag gaggcccttg cgcc                                           24

<210> SEQ ID NO 440
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
gcgcaagggc ctccttctcc gccu                                           24
```

<210> SEQ ID NO 441
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
gccggatcag agccggtaag acca                                              24

<210> SEQ ID NO 442
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ggtcttaccg gctctgatcc ggcc                                              24

<210> SEQ ID NO 443
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
cgctcctcct cgctggttgc tttc                                              24

<210> SEQ ID NO 444
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
aaagcaacca gcgaggagga gcgu                                              24

<210> SEQ ID NO 445
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
cgccggtatt cccagtccgt gtgc                                              24

<210> SEQ ID NO 446
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
cacacggact gggaataccg gcgg                                              24

```
<210> SEQ ID NO 447
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
gtctgctccc gtcgctgcct agau                                           24

<210> SEQ ID NO 448
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tctaggcagc gacgggagca gaca                                           24

<210> SEQ ID NO 449
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ggatctttcg tgcatggcgg caga                                           24

<210> SEQ ID NO 450
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
ctgccgccat gcacgaaaga tccu                                           24

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
cccccccccc cccccccccc cccc                                           24

<210> SEQ ID NO 452
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 452
gggggggggg gggggggggg gggg                                24

<210> SEQ ID NO 453
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
cgtgtatacg agttttctct aggc                                24

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
cctagagaaa actcgtatac acgg                                24

<210> SEQ ID NO 455
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
catgttggat tggattgcgc tagu                                24

<210> SEQ ID NO 456
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
ctagcgcaat ccaatccaac atgc                                24

<210> SEQ ID NO 457
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gaggtgccgg ccgtacccat cctc                                24

<210> SEQ ID NO 458
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
aggatgggta cggccggcac ctcu                                              24

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
agaaaaaagg cccagtcatt tttg                                              24

<210> SEQ ID NO 460
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
aaaaatgact gggccttttt tctg                                              24

<210> SEQ ID NO 461
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
atttattttt acagctgcca catg                                              24

<210> SEQ ID NO 462
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
atgtggcagc tgtaaaaata aata                                              24

<210> SEQ ID NO 463
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tttttgttgg ggttttacta ctac                                              24

<210> SEQ ID NO 464
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
tagtagtaaa accccaacaa aaac                                              24

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
aactgttttg tcaaatactg taac                                              24

<210> SEQ ID NO 466
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ttacagtatt tgacaaaaca gttc                                              24

<210> SEQ ID NO 467
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
aaagctgttt gtaggagtga agcu                                              24

<210> SEQ ID NO 468
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
gcttcactcc tacaaacagc ttta                                              24

<210> SEQ ID NO 469
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
aaacagaact tcatattgtt ccag                                              24
```

```
<210> SEQ ID NO 470
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tggaacaata tgaagttctg ttta                                              24

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
ttccaacaaa aaaattgcaa ttcg                                              24

<210> SEQ ID NO 472
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gaattgcaat tttttgttg gaac                                               24

<210> SEQ ID NO 473
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gctaccagta cagcgctaga tgga                                              24

<210> SEQ ID NO 474
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
ccatctagcg ctgtactggt agcc                                              24

<210> SEQ ID NO 475
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
cgaacatgaa acgtttactt tttc                                              24

<210> SEQ ID NO 476
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
aaaaagtaaa cgtttcatgt tcgc                                              24

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
tgtttgatgg atcacattta tctc                                              24

<210> SEQ ID NO 478
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
agataaatgt gatccatcaa acau                                              24

<210> SEQ ID NO 479
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
tgttggatac cggtactttt tacg                                              24

<210> SEQ ID NO 480
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
gtaaaaagta ccggtatcca acac                                              24

<210> SEQ ID NO 481
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
```
gtacaggggc cactggctat atau                                     24

<210> SEQ ID NO 482
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
tatatagcca gtggccctg taca                                      24

<210> SEQ ID NO 483
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
cactccatta atttccaggg atgc                                     24

<210> SEQ ID NO 484
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
catccctgga aattaatgga gtga                                     24

<210> SEQ ID NO 485
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
ctctctctgc tacatacatc catu                                     24

<210> SEQ ID NO 486
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
atggatgtat gtagcagaga gaga                                     24

<210> SEQ ID NO 487
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487 tttttttgtgg aattttgcac ttgg                                          24

<210> SEQ ID NO 488
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
caagtgcaaa attccacaaa aaaa                                           24

<210> SEQ ID NO 489
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tctcagttta atttggagga tcaa                                           24

<210> SEQ ID NO 490
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
tgatcctcca aattaaactg agaa                                           24

<210> SEQ ID NO 491
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
agacatacat ggcggatcct ctgg                                           24

<210> SEQ ID NO 492
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
cagaggatcc gccatgtatg tctc                                           24

<210> SEQ ID NO 493
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
aaggtcttag cggactactt ggtg                                          24

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
accaagtagt ccgctaagac cttc                                          24

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
cttcgtggcc cttccaatat ctgc                                          24

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
cagatattgg aagggccacg aaga                                          24

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
tggtgaacac gtggtccgcc atga                                          24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
catggcggac cacgtgttca ccag                                          24

<210> SEQ ID NO 499
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 499
gaacaccagg agaacgtaga gggu                                          24

<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
ccctctacgt tctcctggtg ttcc                                          24

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
atccgaagag ggacggcctc gtcu                                          24

<210> SEQ ID NO 502
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
gacgaggccg tccctcttcg gatc                                          24

<210> SEQ ID NO 503
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gtcgtgggca tgcgcaacgt ggac                                          24

<210> SEQ ID NO 504
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
tccacgttgc gcatgcccac gacc                                          24

<210> SEQ ID NO 505
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 505
ggtcgacctc tccgcgttga ggaa                                                24

<210> SEQ ID NO 506
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
tcctcaacgc ggagaggtcg accu                                                24

<210> SEQ ID NO 507
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ggatggtcgc cagggtggag cctc                                                24

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
aggctccacc ctggcgacca tccu                                                24

<210> SEQ ID NO 509
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
aaggctacct gccccatgaa cctc                                                24

<210> SEQ ID NO 510
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
aggttcatgg ggcaggtagc cttg                                                24
```

```
<210> SEQ ID NO 511
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
ggacgacctt accgtcggtg gtcu                                              24

<210> SEQ ID NO 512
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
gaccaccgac ggtaaggtcg tcca                                              24

<210> SEQ ID NO 513
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
ggagctctca cgtctacggc ctcu                                              24

<210> SEQ ID NO 514
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gaggccgtag acgtgagagc tccc                                              24

<210> SEQ ID NO 515
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
gaggtcgttc ttgcggatgg gcag                                              24

<210> SEQ ID NO 516
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 516
tgcccatccg caagaacgac ctcc                                              24

<210> SEQ ID NO 517
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
cgagcactcc gacctcttct atgg                                              24

<210> SEQ ID NO 518
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
catagaagag gtcggagtgc tcgu                                              24

<210> SEQ ID NO 519
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
tcgggctcct ggtttcggct gaga                                              24

<210> SEQ ID NO 520
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
ctcagccgaa accaggagcc cgau                                              24

<210> SEQ ID NO 521
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
tacatgaggc tcacgtacac tccu                                              24

<210> SEQ ID NO 522
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ggagtgtacg tgagcctcat gtac                                            24

<210> SEQ ID NO 523
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
cgcggaggct tatgctgatt cgtu                                            24

<210> SEQ ID NO 524
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
acgaatcagc ataagcctcc gcga                                            24

<210> SEQ ID NO 525
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
cacatgaacc cgtatcgcga gatg                                            24

<210> SEQ ID NO 526
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
atctcgcgat acgggttcat gtgu                                            24

<210> SEQ ID NO 527
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tctttatcac agtggatgca tatg                                              24

<210> SEQ ID NO 528
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
atatgcatcc actgtgataa agaa                                              24

<210> SEQ ID NO 529
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
acagatggtt agcgagtgac agta                                              24

<210> SEQ ID NO 530
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
actgtcactc gctaaccatc tgtu                                              24

<210> SEQ ID NO 531
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
agttgtccga cacttcatcg gtaa                                              24

<210> SEQ ID NO 532
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
taccgatgaa gtgtcggaca actu                                              24

<210> SEQ ID NO 533
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
accgagtgaa tggaagaaaa acga                                            24

<210> SEQ ID NO 534
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534 cgttttctt ccattcactc ggtu                                             24

<210> SEQ ID NO 535
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
acagcaggtt ttcttaaaaa acgu                                            24

<210> SEQ ID NO 536
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536 cgtttttaa gaaaacctgc tgtg                                             24

<210> SEQ ID NO 537
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
ttaagaagag accaaaatat ggtc                                            24

<210> SEQ ID NO 538
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 538
accatatttt ggtctcttct taau                                              24

<210> SEQ ID NO 539
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ttctaaacat tagttctcat cacc                                              24

<210> SEQ ID NO 540
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
gtgatgagaa ctaatgttta gaaa                                              24

<210> SEQ ID NO 541
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
catctagttt gcaacggtcc agtu                                              24

<210> SEQ ID NO 542
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
actggaccgt tgcaaactag atgg                                              24

<210> SEQ ID NO 543
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
gactcgcagc gagagaattt tttu                                              24

<210> SEQ ID NO 544
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
aaaaaattct ctcgctgcga gtcc                                           24

<210> SEQ ID NO 545
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
attcactttc ggacaaatcg aacu                                           24

<210> SEQ ID NO 546
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
gttcgatttg tccgaaagtg aatu                                           24

<210> SEQ ID NO 547
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
aaccatgaga cctttcgcc gcag                                            24

<210> SEQ ID NO 548
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
tgcggcgaaa aggtctcatg gtta                                           24

<210> SEQ ID NO 549
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
```

```
ggccgttaga ttttagtgac gatg                                         24
```

<210> SEQ ID NO 550
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550

```
atcgtcacta aaatctaacg gccg                                         24
```

<210> SEQ ID NO 551
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551

```
gcaacgtgcc gcatgcatcc attc                                         24
```

<210> SEQ ID NO 552
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552

```
aatggatgca tgcggcacgt tgcg                                         24
```

<210> SEQ ID NO 553
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553

```
acagtacatg taggagtact gtgc                                         24
```

<210> SEQ ID NO 554
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554

```
cacagtactc ctacatgtac tgtg                                         24
```

<210> SEQ ID NO 555
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555

```
acattcagtc tctctcacta gttg                                         24
```

<210> SEQ ID NO 556
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
aactagtgag agagactgaa tgta                                          24

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
ctacaaagac atgagctgcc ggga                                          24

<210> SEQ ID NO 558
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
cccggcagct catgtctttg tagc                                          24

<210> SEQ ID NO 559
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gagcgagcga gcctgacggt ctca                                          24

<210> SEQ ID NO 560
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
gagaccgtca ggctcgctcg ctcc                                          24

<210> SEQ ID NO 561
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
actcccaagc caattattat aaga                                          24

<210> SEQ ID NO 562
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
cttataataa ttggcttggg agtg                                              24

<210> SEQ ID NO 563
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
actccagctc ttaaccaatc cacu                                              24

<210> SEQ ID NO 564
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 564
gtggattggt taagagctgg agtu                                              24

<210> SEQ ID NO 565
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
cacctcctct gctttgctct gcca                                              24

<210> SEQ ID NO 566
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
ggcagagcaa agcagaggag gtgg                                              24

<210> SEQ ID NO 567
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 567
gggggcagag gagctccccc tccc                                          24

<210> SEQ ID NO 568
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568 ggaggggggag ctcctctgcc cccc                                         24

<210> SEQ ID NO 569
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
tcgccatgtc tagcagcgac ccgg                                          24

<210> SEQ ID NO 570
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
cgggtcgctg ctagacatgg cgag                                          24

<210> SEQ ID NO 571
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
gcgcgtcgtc gttctcggtt cgcc                                          24

<210> SEQ ID NO 572
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
gcgaaccgag aacgacgacg cgcg                                          24

<210> SEQ ID NO 573
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 573
ggcgacgagt gggcccggcc cgag                                          24

<210> SEQ ID NO 574
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
tcgggccggg cccactcgtc gccg                                          24

<210> SEQ ID NO 575
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
atctgccgtc tcccgcccac cagc                                          24

<210> SEQ ID NO 576
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
ctggtgggcg ggagacggca gatg                                          24

<210> SEQ ID NO 577
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
agccgggcaa ccggaagcag caga                                          24

<210> SEQ ID NO 578
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
ctgctgcttc cggttgcccg gcta                                          24

<210> SEQ ID NO 579
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
```
cctgctcctg ctggccgcag cagc                                          24

<210> SEQ ID NO 580
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
ctgctgcggc cagcaggagc aggg                                          24

<210> SEQ ID NO 581
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
cgcctactac atctgccggt ggcg                                          24

<210> SEQ ID NO 582
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
gccaccggca gatgtagtag gcgu                                          24

<210> SEQ ID NO 583
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
tcctccttct tcgcctcccc ctcc                                          24

<210> SEQ ID NO 584
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584 gaggggagg cgaagaagga ggag                                           24

<210> SEQ ID NO 585
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 585
ggtttaaaaa agatttcttt tttu                                          24

<210> SEQ ID NO 586
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
aaaaaagaaa tcttttttaa accu                                          24

<210> SEQ ID NO 587
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
gtaatcgaca cactaatgca aaga                                          24

<210> SEQ ID NO 588
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
ctttgcatta gtgtgtcgat tacu                                          24

<210> SEQ ID NO 589
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
aacatcttgg acctaaataa ttgu                                          24

<210> SEQ ID NO 590
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 590
caattattta ggtccaagat gttu                                              24

<210> SEQ ID NO 591
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
ctttccattt tcatctttaa atau                                              24

<210> SEQ ID NO 592
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
tatttaaaga tgaaaatgga aagg                                              24

<210> SEQ ID NO 593
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593 acaattttttt tttgggctaa aatg                                             24

<210> SEQ ID NO 594
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
attttagccc aaaaaaaaat tgtg                                              24

<210> SEQ ID NO 595
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
tggtggagtt atgaccacat attg                                              24

<210> SEQ ID NO 596
<211> LENGTH: 24
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
aatatgtggt cataactcca ccau                                        24

<210> SEQ ID NO 597
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
agtgctcaaa aggagagtct actg                                        24

<210> SEQ ID NO 598
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
agtagactct cctttgagc actu                                         24

<210> SEQ ID NO 599
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
ccaccacaag tactatgcaa caaa                                        24

<210> SEQ ID NO 600
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
ttgttgcata gtacttgtgg tgga                                        24

<210> SEQ ID NO 601
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
```
aagaaaatgg aaactttct ctcu                                          24

<210> SEQ ID NO 602
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
gagagaaaag tttccatttt cttg                                         24

<210> SEQ ID NO 603
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
cactagctgt ttacatggtg agca                                         24

<210> SEQ ID NO 604
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
gctcaccatg taaacagcta gtga                                         24

<210> SEQ ID NO 605
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
agaaatactt agtatatatc tata                                         24

<210> SEQ ID NO 606
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
atagatatat actaagtatt tcta                                         24

<210> SEQ ID NO 607
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607

```
actttcatt ctgtaattct ttaa                                              24

<210> SEQ ID NO 608
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
taaagaatta cagaatgaaa agtg                                             24

<210> SEQ ID NO 609
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
ctgtttaaag cttgattttt ttta                                             24

<210> SEQ ID NO 610
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
aaaaaaaatc aagctttaaa cagu                                             24

<210> SEQ ID NO 611
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
atgttctgct tcatttgtgt tgaa                                             24

<210> SEQ ID NO 612
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
tcaacacaaa tgaagcagaa catg                                             24

<210> SEQ ID NO 613
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 613
attggggaac tttcttgaat ccag                                              24

<210> SEQ ID NO 614
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
tggattcaag aaagttcccc aatu                                              24

<210> SEQ ID NO 615
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
catttgaagt tttcttgaaa caaa                                              24

<210> SEQ ID NO 616
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
ttgtttcaag aaaacttcaa atgg                                              24

<210> SEQ ID NO 617
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
cattaccctg ttggaaaaag atgg                                              24

<210> SEQ ID NO 618
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618 catcttttc caacagggta atga                                               24

<210> SEQ ID NO 619
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 619
tactttgttg aaaaccccaa ataa                                              24

<210> SEQ ID NO 620
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
tatttggggt tttcaacaaa gtau                                              24

<210> SEQ ID NO 621
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
cttgaatttc tgaacccaca tcau                                              24

<210> SEQ ID NO 622
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
tgatgtgggt tcagaaattc aagg                                              24

<210> SEQ ID NO 623
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
gttttgctgt taaagctagt accu                                              24

<210> SEQ ID NO 624
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
ggtactagct ttaacagcaa aacc                                              24

<210> SEQ ID NO 625
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 625
ggttctagga agttttgtga aacu                                          24

<210> SEQ ID NO 626
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
gtttcacaaa acttcctaga acca                                          24

<210> SEQ ID NO 627
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
tgggtagaag tgtttgtgtt aagg                                          24

<210> SEQ ID NO 628
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
cttaacacaa acacttctac ccaa                                          24

<210> SEQ ID NO 629
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
tagtagtagt gctcttttag agcu                                          24

<210> SEQ ID NO 630
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 630
gctctaaaag agcactacta ctac        24

<210> SEQ ID NO 631
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 631
gtacctgaga ccaaaaagga gaau        24

<210> SEQ ID NO 632
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
ttctcctttt tggtctcagg taca        24

<210> SEQ ID NO 633
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
ttgattttga gcttcctatg tatg        24

<210> SEQ ID NO 634
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
atacatagga agctcaaaat caag        24

<210> SEQ ID NO 635
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 635
cttgctgtgg ttggtggtgg cccu        24

<210> SEQ ID NO 636

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
gggccaccac caaccacagc aaga                                            24

<210> SEQ ID NO 637
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
caggacttgc tgttgcacag caag                                            24

<210> SEQ ID NO 638
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
ttgctgtgca acagcaagtc ctgc                                            24

<210> SEQ ID NO 639
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
ttctgaagca ggactctctg tttg                                            24

<210> SEQ ID NO 640
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
aaacagagag tcctgcttca gaaa                                            24

<210> SEQ ID NO 641
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
tcaattgatc cgaatcctaa attg                                            24

<210> SEQ ID NO 642
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
aatttaggat tcggatcaat tgaa                                           24

<210> SEQ ID NO 643
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 643
tatggcctaa taactatggt gttu                                           24

<210> SEQ ID NO 644
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
aacaccatag ttattaggcc atau                                           24

<210> SEQ ID NO 645
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ttgttagatt gtctagatgc tacc                                           24

<210> SEQ ID NO 646
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
gtagcatcta gacaatctaa caag                                           24

<210> SEQ ID NO 647
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
```

```
ggtctggtgc agcagtgtac attg                                          24

<210> SEQ ID NO 648
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
aatgtacact gctgcaccag acca                                          24

<210> SEQ ID NO 649
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
tgataatacg gctaaagatc ttca                                          24

<210> SEQ ID NO 650
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650
gaagatcttt agccgtatta tcau                                          24

<210> SEQ ID NO 651
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
agaccttatg gaagggttaa ccgg                                          24

<210> SEQ ID NO 652
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
cggttaaccc ttccataagg tcta                                          24

<210> SEQ ID NO 653
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 653
aacagctgaa atcgaaaatg atgc                                              24

<210> SEQ ID NO 654
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
catcattttc gatttcagct gttu                                              24

<210> SEQ ID NO 655
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
ttccaccaag ccaaagttat aaag                                              24

<210> SEQ ID NO 656
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
tttataactt tggcttggtg gaau                                              24

<210> SEQ ID NO 657
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
tgattcatga ggaatcgaaa tcca                                              24

<210> SEQ ID NO 658
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ggatttcgat tcctcatgaa tcac                                              24

<210> SEQ ID NO 659
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 659
gttgatatgc aatgatggta ttac                                              24

<210> SEQ ID NO 660
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
taataccatc attgcatatc aaca                                              24

<210> SEQ ID NO 661
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
attcaggcaa cggtggtgct cgau                                              24

<210> SEQ ID NO 662
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
tcgagcacca ccgttgcctg aata                                              24

<210> SEQ ID NO 663
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
caactggctt ctctagatct cttg                                              24

<210> SEQ ID NO 664
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
aagagatcta gagaagccag ttgc                                              24

<210> SEQ ID NO 665
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
tcaaaaacct cccacctacc gcgu                                            24

<210> SEQ ID NO 666
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
cgcggtaggt gggaggtttt tgaa                                            24

<210> SEQ ID NO 667
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
ucaaaaaccu cccaccuacc gcgu                                            24

<210> SEQ ID NO 668
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
cgcgguaggu gggagguuuu ugaa                                            24

<210> SEQ ID NO 669
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
tcaaaaacct cccacctacc gcgu                                            24

<210> SEQ ID NO 670
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
```

```
cgcggtaggt gggaggtttt tgaa                                              24

<210> SEQ ID NO 671
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
tcaaaaacct cccacctacc gcgu                                              24

<210> SEQ ID NO 672
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
cgcggtaggt gggaggtttt tgaa                                              24

<210> SEQ ID NO 673
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
tcaaaaacct cccacctacc gcgu                                              24

<210> SEQ ID NO 674
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
cgcggtaggt gggaggtttt tgaa                                              24
```